(12) United States Patent
Silvestre et al.

(10) Patent No.: US 8,735,349 B2
(45) Date of Patent: May 27, 2014

(54) METHOD FOR IMPROVING GLUCOSE TOLERANCE IN A DIABETES TYPE 2 PATIENT OF YOUNGER THAN 50 YEARS AND HAVING POSTPRANDIAL PLASMA GLUCOSE CONCENTRATION OF AT LEAST 14 MMOL/L

(75) Inventors: Louise Silvestre, Paris (FR); Gabor Boka, Paris (FR); Patrick Miossec, Paris (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/467,757

(22) Filed: May 9, 2012

(65) Prior Publication Data

US 2013/0023467 A1    Jan. 24, 2013

(30) Foreign Application Priority Data

May 13, 2011 (EP) .................................. 11166058

(51) Int. Cl.
*A61P 3/10* (2006.01)
*A61K 38/26* (2006.01)

(52) U.S. Cl.
USPC .............................. 514/6.8; 514/6.7; 514/7.2

(58) Field of Classification Search
None
See application file for complete search history.

(56) References Cited

U.S. PATENT DOCUMENTS

| 2002/0177151 A1 | 11/2002 | Gimeno |
| 2004/0092590 A1 | 5/2004 | Arterburn et al. |

FOREIGN PATENT DOCUMENTS

| EP | 2324853 A1 | 5/2011 |

OTHER PUBLICATIONS

Ratner, R. E. et al., "Dose-dependent effects of the once-daily GLP-1 receptor agonist lixisenatide in patients with Type 2 diabetes inadequately controlled with metformin: a randomized, double-blind, placebo-controlled trial," Diabetic Medicine (2010), vol. 27, pp. 1024-1032.
Rosenstock, J. et al., "Dose range effects of the new once daily GLP-1 receptor agonist AVE0010 added to metformin in type 2 diabetes," Diabetologia (2008), vol. 51, p. S66.
Christensen, Mikkel et al., "Lixisenatide, a novel GLP-1 receptor agonist for the treatment of type 2 diabetes mellitus," I Drugs (2009), vol. 12, No. 8, pp. 503-513.
ClinicalTrials.gov, "24-week Study Comparing Lixisenatide (AVE0010) to Sitagliptin as add-on to Metformin in Obese Type 2 Diabetic Patients Younger Than 50," May 6, 2011, http://clinicaltrials.gov/show/NCT00976937, Retrieved Nov. 7, 2011.
ClinicalTrials.gov, "Dose Ranging Study of the GLP-1 Agonist AVE0010 in Metformin-Treated Subjects With Type 2 Diabetes Mellitus," Jun. 22, 2010, http://clinicaltrials.gov/ct2/show/NCT00299871?term=nct00299871&rank=1, Retrieved Nov. 7, 2011.
International Search Report dated Jul. 12, 2012 issued in PCT/EP2012/058745.
Gavin III, J. R., et al., "Report of the expert committee on the diagnosis and classification of diabetes mellitus" Diabetes Care (Jul. 1997) pp. 1183-1197, vol. 20, No. 7.
Gerich, J.E. et al., Poster Presentation Abstract 830 "Monotherapy with GLP-1 receptor agonist, Lixisenatide, significantly improves glycaemis control in type 2 diabetic patients" 46th Annual Meeting of EASD, Stockholm, Sweden (Sep. 2010) 5 pages.
Ratner, R.E. et al., Abstract 433-P "A Dose-Finding Study of the New GLP-1 Agonist AVE0010 in Type 2 Diabetes insufficiently Controlled with Metformin" 68th American Diabetes Association Meeting, San Fransisco, California (Jun. 2008), 1 page.
Sanofi-Aventis Press Release "Once Daily Lixisenatide (AVE 0010) Given as Monotherapy Successfully Meets Phase III Study Endpoints in Diabetes" (Apr. 15, 2010) in Paris, France, pp. 1-2.
Sharplin, P. et al., "Improved glycaemic control by switching from insulin NPH to insulin glargine: a retrospective observational study" Cardiovascular Diabetology (Jan. 2009) pp. 1-8, vol. 8, No. 3.
Fonseca, V.A. et al., "Efficacy and Safety of the Once-Daily GLP-1 Receptor Agonist Lixisenatide in Monotherapy" Diabetes Care (Jun. 2012) pp. 1225-1231, vol. 35.
U.S. Office Action dated Jul. 15, 2013, received in U.S. Appl. No. 13/467,707.
Office Action dated Apr. 8, 2013 from related application U.S. Appl. No. 13/432,811.

*Primary Examiner* — Gyan Chandra
(74) *Attorney, Agent, or Firm* — Scully, Scott, Murphy & Presser, P.C.

(57) ABSTRACT

The present invention refers to a pharmaceutical combination for use in inducing weight loss in diabetes type 2 patients or/and for preventing weight gain in diabetes type 2 patients.

9 Claims, 16 Drawing Sheets

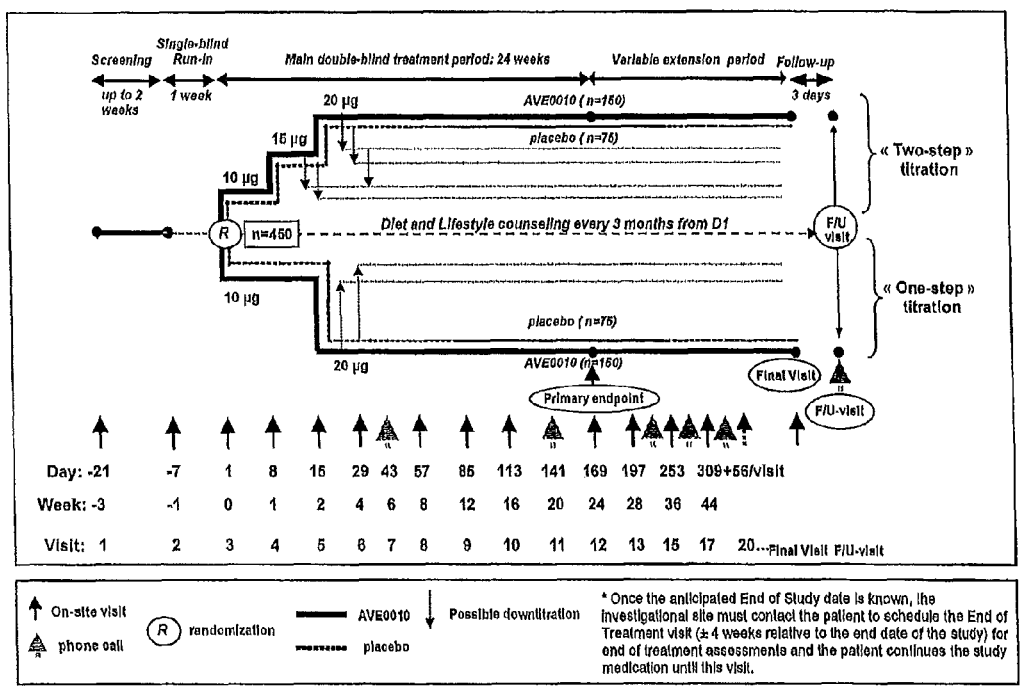
Figure 1 Study design

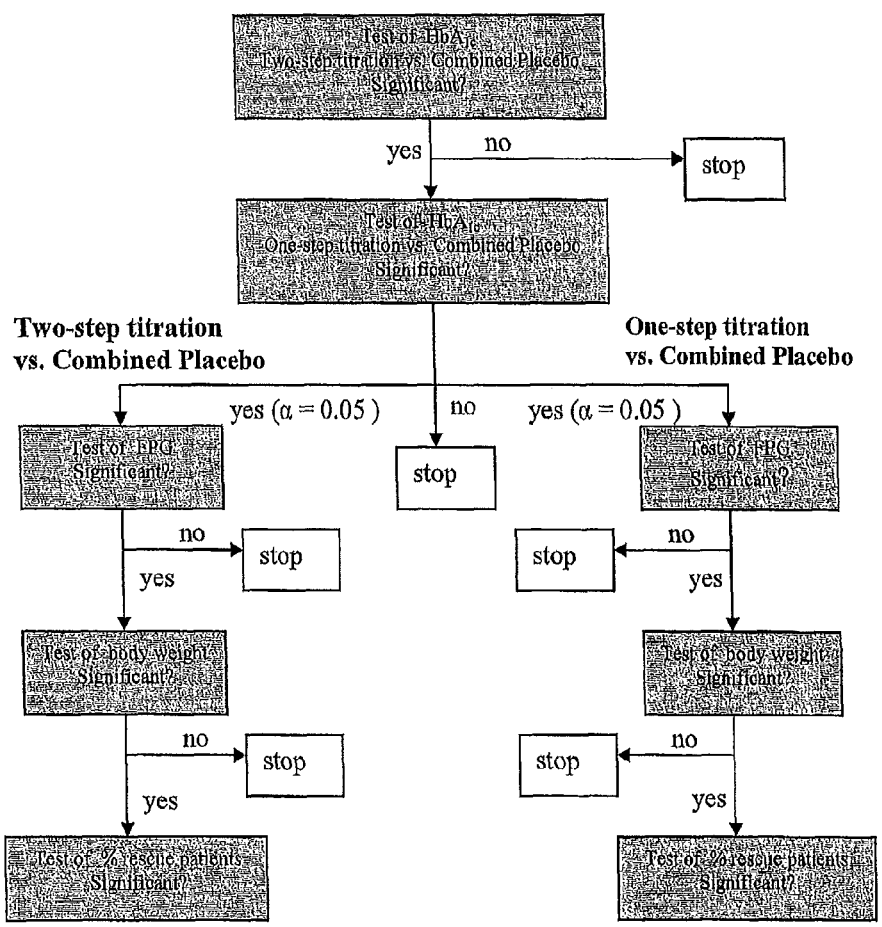
Figure 2 The overall step-down testing procedure

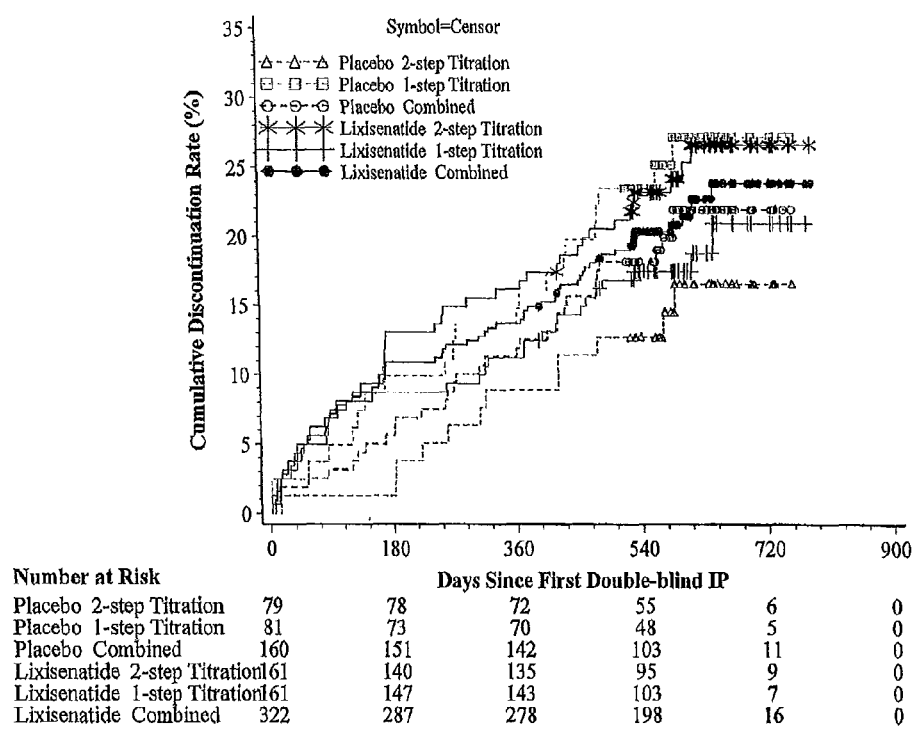
Figure 3 Kaplan-Meier plot of time to treatment discontinuation due to any reason – Randomized population Figure 4 illustrates the mean (±SE) change from baseline in HbA$_{1c}$ over time during the main 24-week double-blind treatment period. Figure 7 in the appendix illustrates the mean (±SE) change from baseline in HbA$_{1c}$ over time up to Week 76. The HbA$_{1c}$ reduction was relatively maintained over time beyond 24 weeks.

Figure 4 Plot of mean change in HbA$_{1c}$ (%) from baseline by visit during the main 24-week treatment period– mITT population

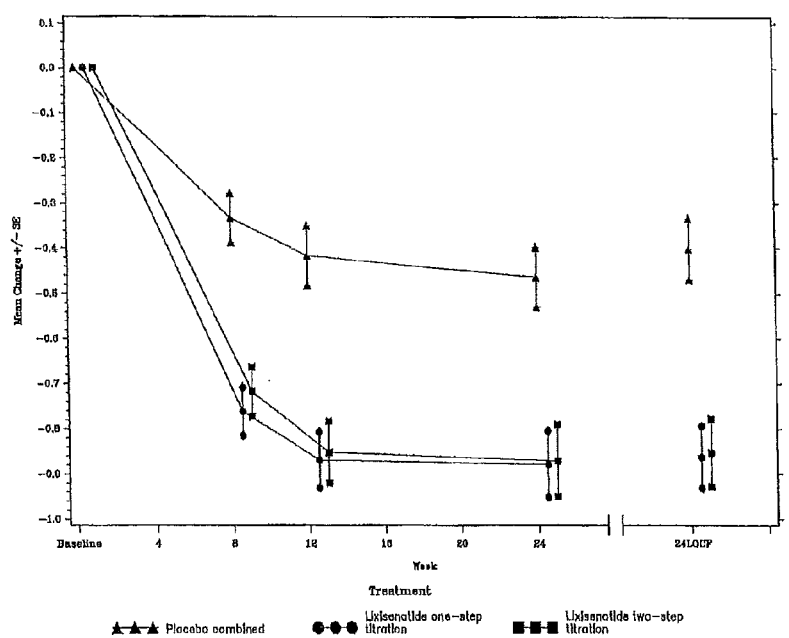

LOCF = Last observation carried forward.
Note: The plot included measurements obtained before the introduction of rescue medication and up to 3 days after the last dose of the double-blind investigational product injection on or before Visit 12 (Week24), or Day 169 if Visit 12 (Week24) is not available.

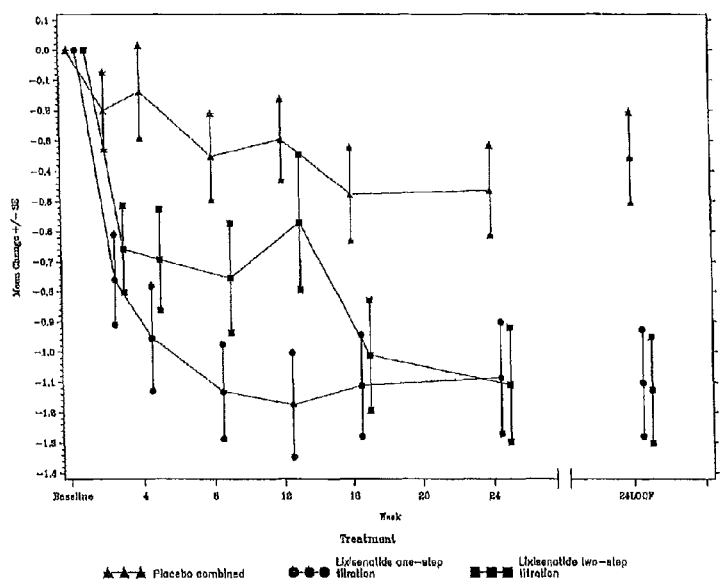

Figure 5 Plot of mean change in fasting plasma glucose (mmol/L) from baseline by visit during the main 24-week treatment period – mITT population LOCF = Last observation carried forward.
Note: The plot included measurements obtained before the introduction of rescue medication and up to 1 day after the last dose of the double-blind investigational product injection on or before Visit 12 (Week24), or Day 169 if Visit 12 (Week24) is not available.

Figure 6 Plot of mean change in body weight (kg) from baseline by visit during the main 24-week treatment period – mITT population

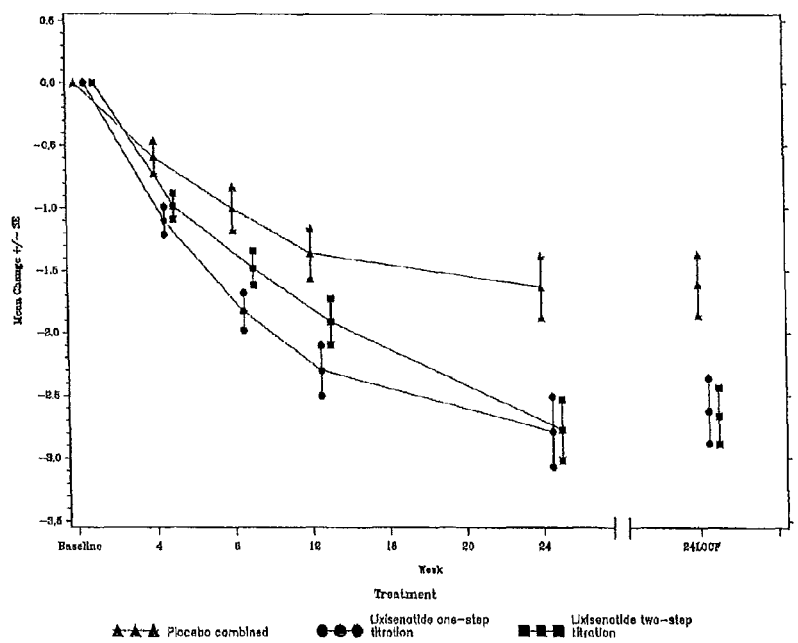

LOCF = Last observation carried forward.
Note: The plot included measurements obtained before the introduction of rescue medication and up to 3 days after the last dose of the double-blind investigational product injection on or before Visit 12 (Week24), or Day 169 if Visit 12 (Week 24) is not available.

Figure 7 Plot of mean change in HbA$_{1c}$ (%) from baseline by visit and at endpoint–mITT population

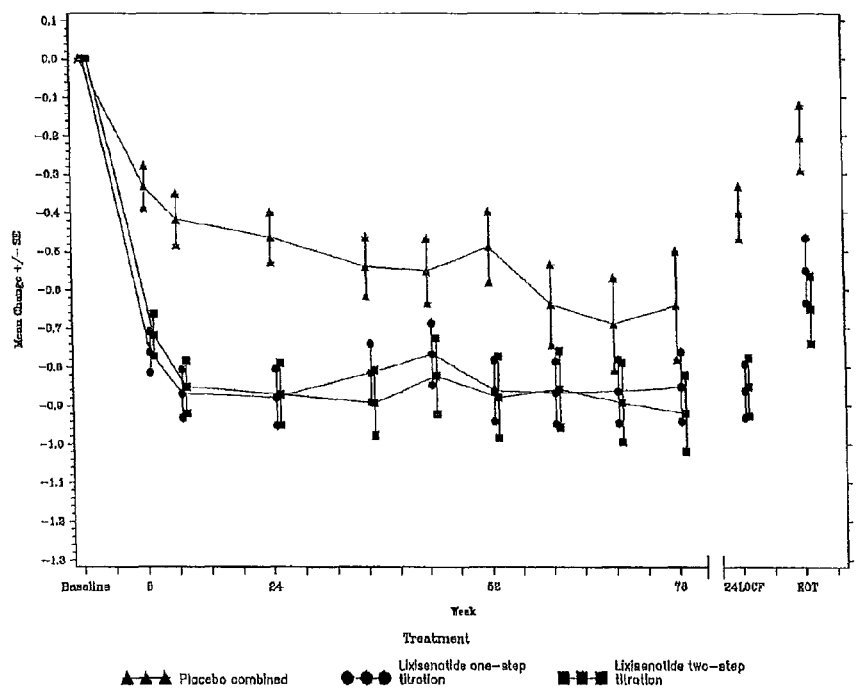

LOCF = Last observation carried forward, EOT = Last on-treatment value.
Note: The analysis excluded measurements obtained after the introduction of rescue medication and/or after the treatment cessation plus 3 days.
For Week 24 (LOCF), the analysis included measurements obtained up to 3 days after the last dose of the double-blind investigational product injection on or before Visit 12 (Week24), or Day 169 if Visit 12 (Week 24) is not available.

Figure 8 Plot of mean change in fasting plasma glucose (mmol/L) from baseline by visit and at endpoint – mITT population

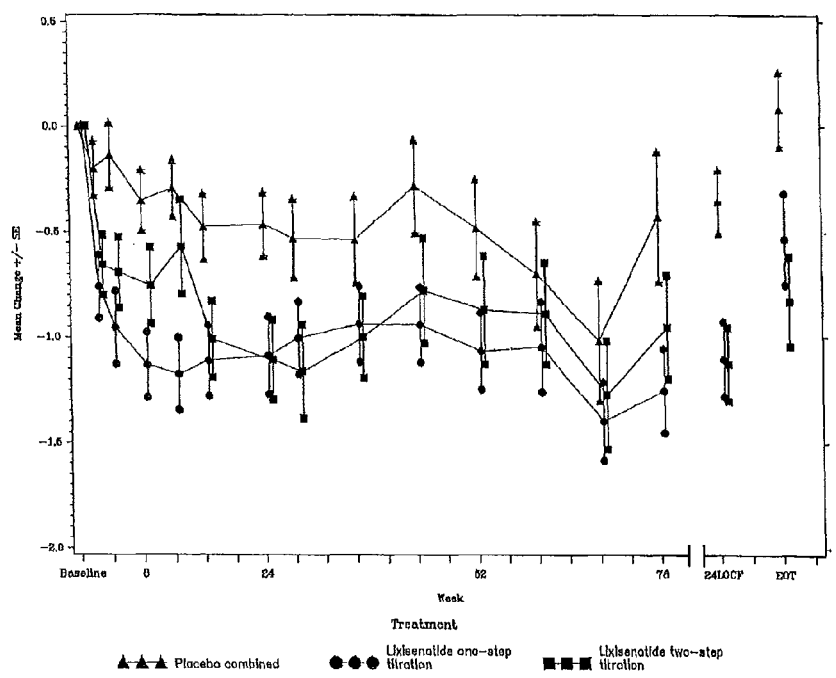

LOCF = Last observation carried forward, EOT = Last on-treatment value.
Note: The analysis excluded measurements obtained after the introduction of rescue medication and/or after the treatment cessation plus 1 day.
For Week 24 (LOCF), the analysis included measurements obtained up to 1 day after the last dose of the double-blind investigational product injection on or before Visit 12 (Week24), or Day 169 if Visit 12 (Week 24) is not available.

Figure 9 Plot of mean change in body weight (kg) from baseline by visit and at endpoint – mITT population

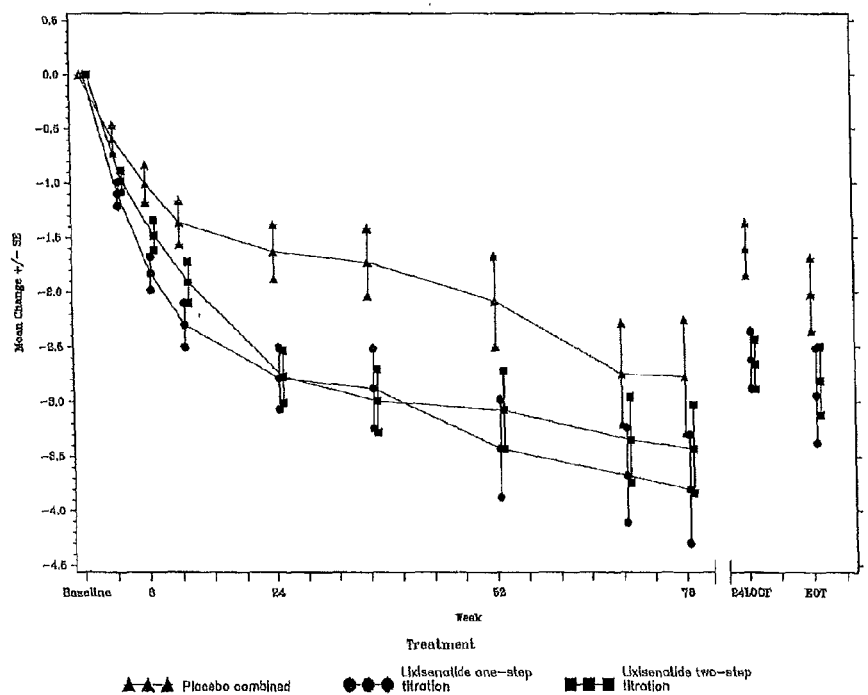

LOCF = Last observation carried forward, EOT = Last on-treatment value.
Note: The analysis excluded measurements obtained after the introduction of rescue medication and/or after the treatment cessation plus 3 days.
For Week 24 (LOCF), the analysis included measurements obtained up to 3 days after the last dose of the double-blind investigational product injection on or before Visit 12 (Week24), or Day 169 if Visit 12 (Week 24) is not available.

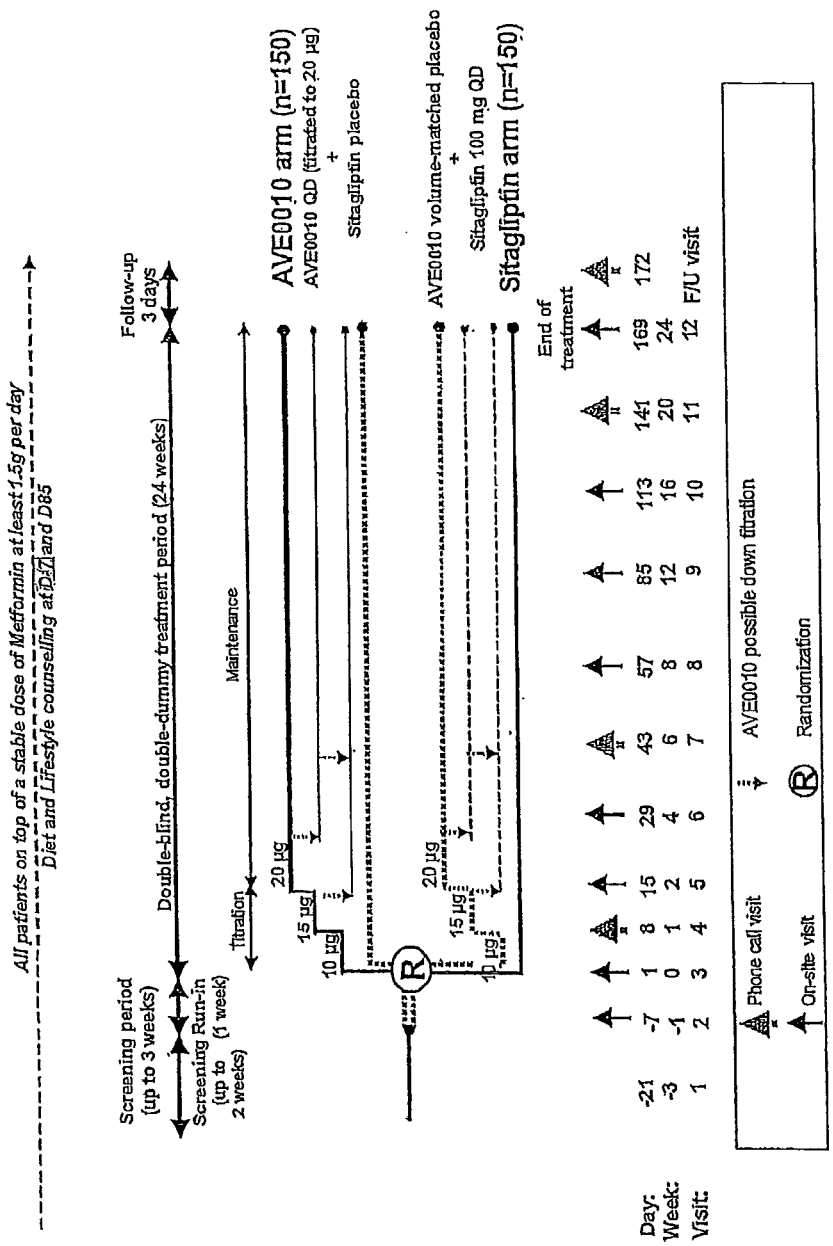
FIGURE 10 - STUDY DESIGN

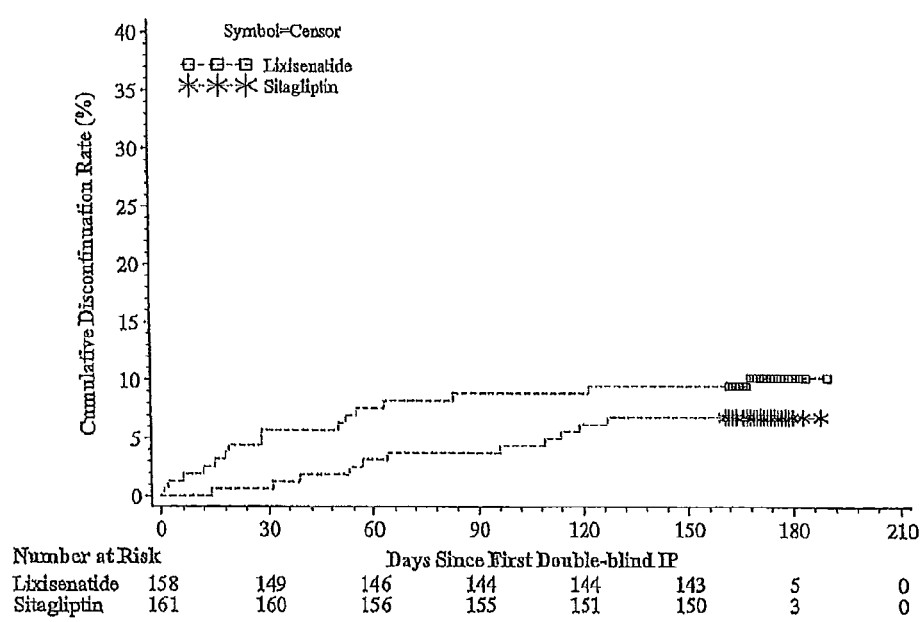
Figure 11 - Kaplan-Meier plot of time to treatment discontinuation due to any reason - Randomized population Figure 12 - Plot of responders (patients with HbA1c<7% and weight loss of
≥ 5% of baseline body weight) by visits and at endpoint - mITT population

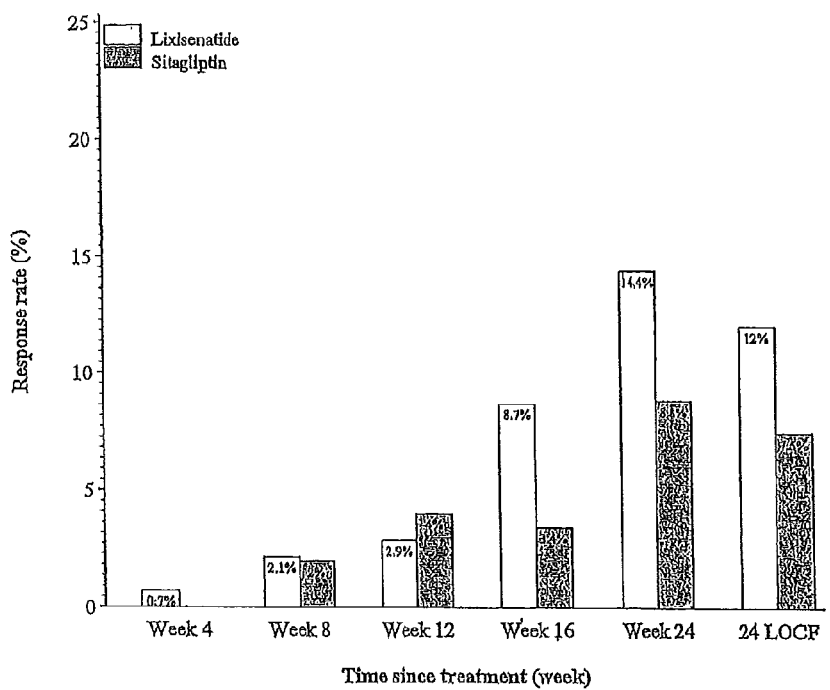

LOCF = Last observation carried forward.
Note: The analysis excluded measurements obtained after the introduction of rescue medication and/or after the treatment cessation plus 3 days.
For week 24 (LOCF), patients who do not have post-baseline on-treatment values (HbA1c and body weight) that are no more than 30 days apart are counted as non-responders.

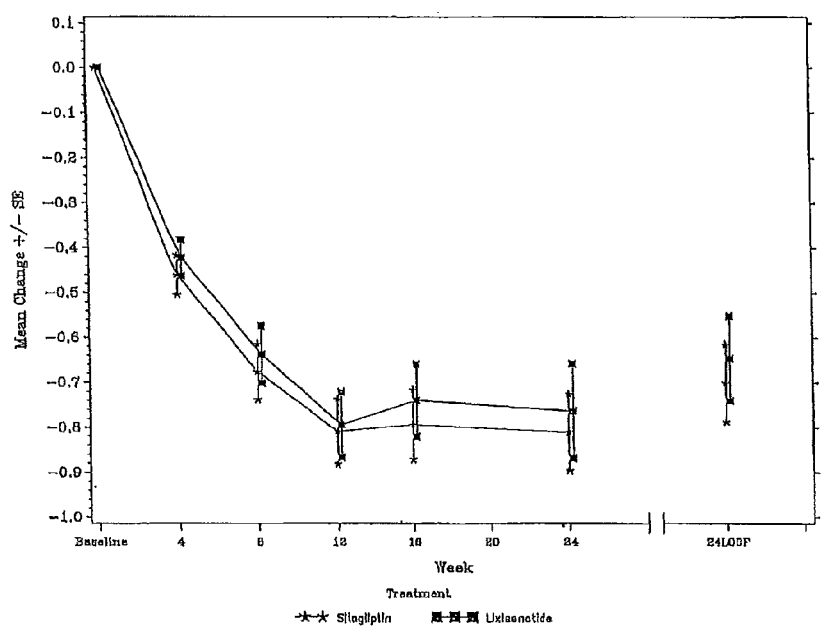
Figure 13 - Plot of mean change in HbA1c (%) from baseline by visit and at endpoint - mITT population
LOCF = Last observation carried forward.
Note: The analysis excluded measurements obtained after the introduction of rescue medication and/or after the treatment cessation plus 3 days.

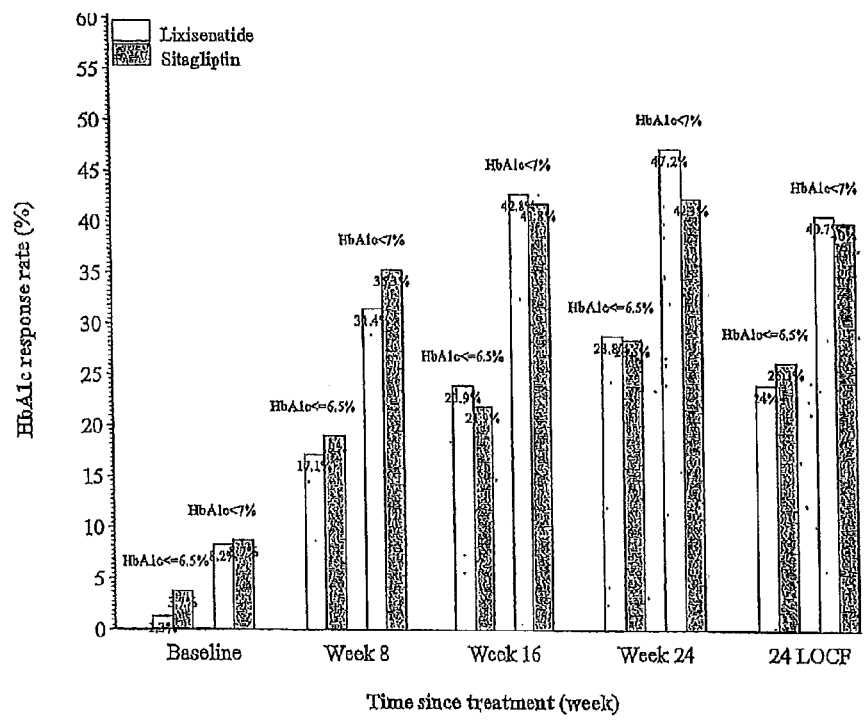
Figure 14 - Plot of HbA1c responders (≥ 6.5% or <7% respectively) at selected visits and at endpoint - mITT population
LOCF = Last observation carried forward.
Note: The analysis excluded measurements obtained after the introduction of rescue medication and/or after t] treatment cessation plus 3 days.

Figure 15 - Plot of mean change in body weight (kg) from baseline by visit and at endpoint - mITT population
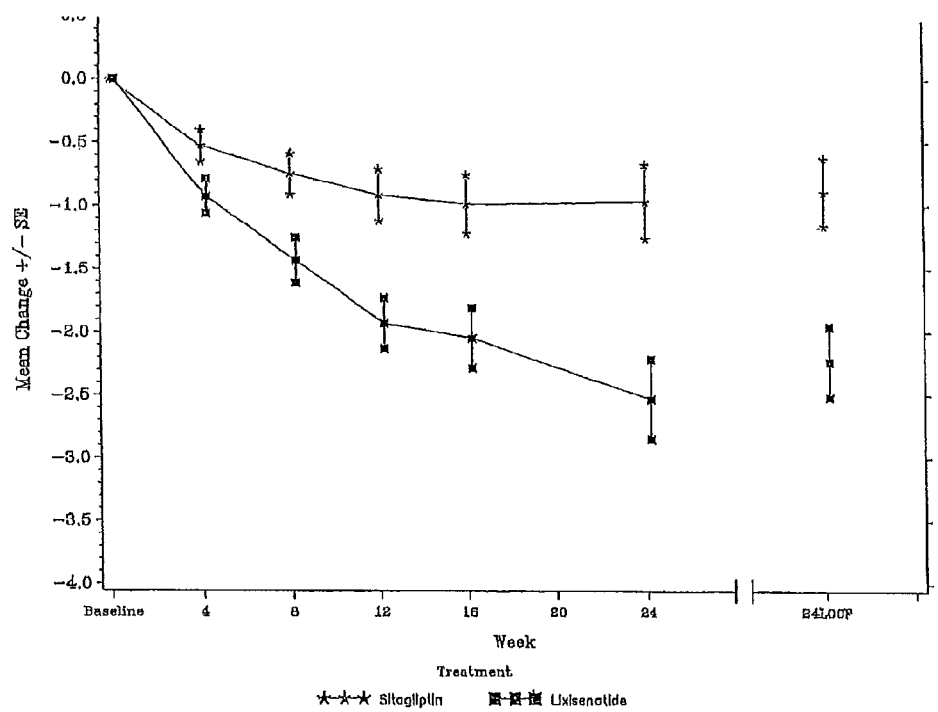
LOCF = Last observation carried forward.
Note: The analysis excluded measurements obtained after the introduction of rescue medication and/or after the treatment cessation plus 3 days.

Table 16 - Plot of mean change in fasting plasma glucose (mmol/L) from baseline by visit and at endpoint - mITT population
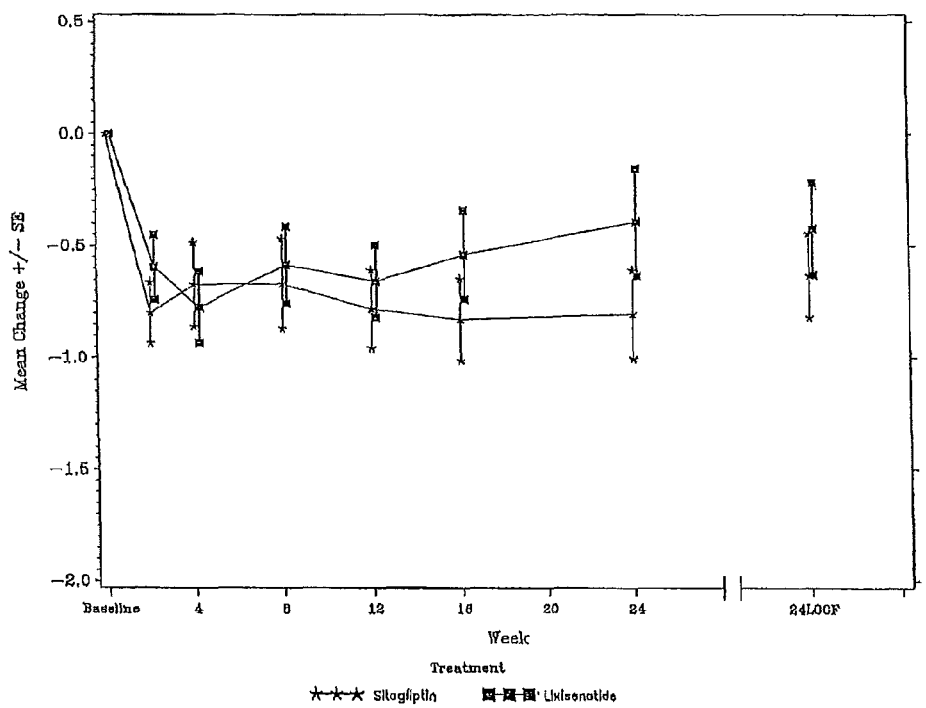
LOCF = Last observation carried forward.
Note: The analysis excluded measurements obtained after the introduction of rescue medication and/or after the treatment cessation plus 1 day.

SEQUENCE LISTING

```
<160> NUMBER OF SEQ ID NOS: 2

<210> SEQ ID NO 1
<211> LENGTH: 44
<212> TYPE: PRT
<213> ORGANISM: Artificial Sequence
<220> FEATURE:
<221> NAME/KEY: SOURCE
<222> LOCATION: 1..44
<223> OTHER INFORMATION: /mol_type="protein"
      /note="desPro36Exendin-4(1-39)-Lys6-NH2"
      /organism="Artificial Sequence"

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Artificial Sequence
<220> FEATURE:
<221> NAME/KEY: SOURCE
<222> LOCATION: 1..39
<223> OTHER INFORMATION: /mol_type="protein"
      /note="native Exendin-4 sequence"
      /organism="Artificial Sequence"

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

METHOD FOR IMPROVING GLUCOSE TOLERANCE IN A DIABETES TYPE 2 PATIENT OF YOUNGER THAN 50 YEARS AND HAVING POSTPRANDIAL PLASMA GLUCOSE CONCENTRATION OF AT LEAST 14 MMOL/L

Subject of the present invention is a pharmaceutical combination for use in inducing weight loss in diabetes type 2 patients or/and for preventing weight gain in diabetes type 2 patients, said combination comprising (a) desPro$^{36}$Exendin-4(1-39)-Lys$_6$-NH$_2$ (AVE0010, lixisenatide) or/and a pharmaceutically acceptable salt thereof, and (b) metformin or/and a pharmaceutically acceptable salt thereof. Yet another aspect is a method for inducing weight loss in diabetes type 2 patients or/and for preventing weight gain in diabetes type 2 patients, comprising administering the combination of the present invention to a subject in need thereof.

In a healthy person the release of insulin by the pancreas is strictly coupled to the concentration of blood glucose. An increased level of blood glucose, as appears after meals, is rapidly counterbalanced by a respective increase in insulin secretion. In fasting condition the plasma insulin level drops to a basal value which is sufficient to ensure the continuous supply of glucose to insulin-sensitive organs and tissues and to keep the hepatic glucose production at a low level at night.

In contrast to diabetes type 1, there is not generally a lack of insulin in diabetes type 2 but in many cases, particularly in progressive cases, the treatment with insulin is regarded as the most suitable therapy, if required in combination with orally administered anti-diabetic drugs.

An increased glucose level in the blood over several years without initial symptoms represents a significant health risk. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications. Examples for diabetes complications are micro and macrovascular damages that possibly manifest themselves in retinopathies, nephropathies or neuropathies and lead to blindness, renal failure and the loss of extremities and are accompanied by an increased risk of cardiovascular diseases. It can thus be concluded that an improved therapy of diabetes primarily has to aim keeping blood glucose in the physiological range as closely as possible.

A particular risk exists for overweight patients suffering from diabetes type 2, e.g. patients with a body mass index (BMI) ≥30. In these patients the risks of diabetes overlap with the risks of overweight, leading e.g. to an increase of cardiovascular diseases compared to diabetes type 2 patients being of a normal weight. Thus, it is particularly necessary to treat diabetes in these patients while reducing the overweight.

Metformin is a biguanide hypoglycemic agent used in the treatment of non-insulin-dependent diabetes mellitus (diabetes mellitus type 2) not responding to dietary modification. Metformin improves glycemic control by improving insulin sensitivity and decreasing intestinal absorption of glucose. Metformin is usually administered orally. However, control diabetes mellitus type 2 in obese patients by metformin may be insufficient. Thus, in these patients, additional measures for controlling diabetes mellitus type 2 may be required.

The compound desPro$^{36}$Exendin-4(1-39)-Lys$_6$-NH$_2$ (AVE0010, lixisenatide) is a derivative of Exendin-4. AVE0010 is disclosed as SEQ ID NO:93 in WO 01/04156:

```
SEQ ID NO: 1: AVE0010 (44 AS)
H-G-E-G-T-F-T-S-D-L-S-K-Q-M-E-E-E-A-V-R-L-F-I-E-
W-L-K-N-G-G-P-S-S-G-A-P-P-S-K-K-K-K-K-K-NH₂

SEQ ID NO: 2: Exendin-4 (39 AS)
H-G-E-G-T-F-T-S-D-L-S-K-Q-M-E-E-E-A-V-R-L-F-I-E-
W-L-K-N-G-G-P-S-S-G-A-P-P-P-S-NH₂
```

Exendins are a group of peptides which can lower blood glucose concentration. The Exendin analogue AVE0010 is characterised by C-terminal truncation of the native Exendin-4 sequence. AVE0010 comprises six C-terminal lysine residues not present in Exendin-4.

In the context of the present invention, AVE0010 includes pharmaceutically acceptable salts thereof. The person skilled in the art knows pharmaceutically acceptable salts of AVE0010. A preferred pharmaceutically acceptable salt of AVE0010 employed in the present invention is acetate.

In Example 1 of the present invention, it has been demonstrated in diabetes type 2 patients that AVE0010 (Lixisenatide) in an add-on therapy to metformin significantly improved glycemic control and decreased weight:

HbA1c was significantly decreased in both groups
    2-step titration: LS mean difference of −0.41% in HbA1c vs placebo (p<0.0001)
    1-step titration: LS mean difference of −0.49% in HbA1c vs placebo (p<0.0001)
Significantly more lixisenatide patients achieved HbA1c targets (≤6.5% & <7.0%)
Fasting plasma glucose (FPG) was significantly improved with lixisenatide
Significant weight loss was induced
    2-step: LS mean difference of −1.05 kg vs placebo (p=0.0025)
    1-step: LS mean difference of −1.00 kg vs placebo (p=0.0042)

A sustained efficacy throughout the entire treatment period was observed.

In Example 2 of the present invention, in obese type 2 diabetic patients younger than 50 years not adequately controlled by metformin, Lixisenatide (AVE0010) demonstrated to significantly reduce HbA1c and weight in young obese patients with type 2 diabetes over a period of 24 weeks,
Lixisenatide (AVE0010) demonstrated significant advantage over sitagliptin in terms of weight loss and similar magnitude of HbA1c reduction,
Lixisenatide (AVE0010) demonstrated a very favorable safety and tolerability profile over sitagliptin and specifically no difference in the incidence of hypoglycemia,
Lixisenatide (AVE0010) efficacy is supported by its dual efficacy in reducing both PPG and FPG,
wherein Lixisenatide was administered in an add-on therapy to metformin.

A first aspect of the present invention is a pharmaceutical combination for use in inducing weight loss in diabetes type 2 patients or/and for preventing weight gain in diabetes type 2 patients, said combination comprising
(a) desPro$^{36}$Exendin-4(1-39)-Lys$_6$-NH$_2$ or/and a pharmaceutically acceptable salt thereof, and
(b) metformin or/and a pharmaceutically acceptable salt thereof.

Metformin is the international nonproprietary name of 1,1-dimethylbiguanide (CAS Number 657-24-9). In the present invention, the term "metformin" includes any pharmaceutically acceptable salt thereof.

In the present invention, metformin may be administered orally. The skilled person knows formulations of metformin suitable for treatment of diabetes type 2 by oral administration. Metformin may be administered to a subject in need thereof, in an amount sufficient to induce a therapeutic effect. Metformin may be administered in a dose of at least 1.0 g/day or at least 1.5 g/day. For oral administration, metformin may be formulated in a solid dosage form, such as a tablet or pill. Metformin may be formulated with suitable pharmaceutically acceptable carriers, adjuvants, or/and auxiliary substances.

In the present invention, desPro$^{36}$Exendin-4(1-39)-Lys$_6$-NH$_2$ or/and a pharmaceutically acceptable salt may be administered in an add-on therapy to administration of metformin.

In the present invention, the terms "add-on", "add-on treatment" and "add-on therapy" relate to treatment of diabetes mellitus type 2 with metformin and AVE0010. Metformin and AVE0010 may be administered within a time interval of 24 h. Metformin and AVE0010 each may be administered in a once-a-day-dosage. Metformin and AVE0010 may be administered by different administration routes. Metformin may be administered orally, and AVE0010 may be administered parenterally.

The subject to be treated by the medicament of the present invention suffering from diabetes type 2 may be a subject suffering from diabetes type 2. Example 1 demonstrates in these patients, that administration of AVE0010 in combination with metformin provides an advantageous therapy.

The subject to be treated by the medicament of the present invention suffering from diabetes type 2 may be a subject suffering from diabetes type 2, wherein diabetes type 2 is not adequately controlled by treatment with metformin alone, for instance with a dose of at least 1.0 g/day metformin or at least 1.5 g/day metformin for 3 months. In the present invention, a subject the diabetes type 2 of which is not adequately controlled may have a HbA1c value in the range of 7% to 10%.

The subject to be treated by the medicament of the present invention suffering from diabetes type 2 may be an obese subject. In the present invention, an obese subject may have a body mass index of at least 30 kg/m$^2$.

The subject to be treated by the medicament of the present invention suffering from diabetes type 2 may be an obese subject, as described herein, and may be younger than 50 years, for example at least 18 years old and younger than 50 years, wherein the subject is not adequately controlled with metformin. Example 2 demonstrates in these patients, that administration of AVE0010 in combination with metformin provides an advantageous therapy.

The subject to be treated by the medicament of the present invention suffering from diabetes type 2 may have a normal body weight. In the present invention, a subject having normal body weight may have a body mass index in the range of 17 kg/m$^2$ to 25 kg/m$^2$, or 17 kg/m$^2$ to <30 kg/m$^2$.

The subject to be treated by the medicament of the present invention may be an adult subject. The subject may have an age of at least 18 years of may have an age in the range of 18 to 80 years, of 18 to 50 years, or 40 to 80 years, or 50 to 60 years. The subject may be younger than 50 years.

The subject to be treated by the medicament of the present invention preferably does not receive an antidiabetic treatment, for instance by insulin or/and related compounds.

The subject to be treated by the medicament of the present invention may suffer from diabetes mellitus type 2 for at least 1 year or at least 2 years. In particular, in the subject to be treated, diabetes mellitus type 2 has been diagnosed at least 1 year or at least 2 years before onset of therapy by the medicament of the present invention.

The subject to be treated may have a HbA$_{1c}$ value of at least about 8% or at least about 7.5%. The subject may also have a HbA$_{1c}$ value of about 7 to about 10%. The example of the present invention demonstrates that treatment by AVE0010 results in a reduction of the HbA$_{1c}$ value in diabetes type 2 patients.

In yet another aspect of the present invention, the combination as described herein can be used for improving glycemic control. In the present invention, improvement of glycemic control in particular refers to improvement of postprandial plasma glucose concentration, improvement of fasting plasma glucose concentration, or/and improvement of the HbA$_{1c}$ value.

In yet another aspect of the present invention, the combination as described herein can be used for improving the HbA$_{1c}$ value in a patient suffering from diabetes type 2. Improving the HbA$_{1c}$ value means that the HbA$_{1c}$ value is reduced below 6.5% or 7%, for example after treatment for at least one month, at least two months, or at least three months.

In yet another aspect of the present invention, the combination as described herein can be used for improving glucose tolerance in a patient suffering from diabetes type 2. Improving glucose tolerance means that the postprandial plasma glucose concentration is reduced by the active agent of the present invention. Reduction means in particular that the plasma glucose concentration reaches normoglycemic values or at least approaches these values.

In the present invention, normoglycemic values are blood glucose concentrations of in particular 60-140 mg/dl (corresponding to 3,3 bis 7.8 mM/L). This range refers in particular to blood glucose concentrations under fasting conditions and postprandial conditions.

The subject to be treated may have a 2 hours postprandial plasma glucose concentration of at least 10 mmol/L, at least 12 mmol/L, or at least 14 mmol/L. These plasma glucose concentrations exceed normoglycemic concentrations.

The subject to be treated may have a glucose excursion of at least 2 mmol/L, at least 3 mmol/L, at least 4 mmol/L or at least 5 mmol/L. In the present invention, the glucose excursion is in particular the difference of the 2 hours postprandial plasma glucose concentration and the plasma glucose concentration 30 minutes prior to a meal test.

"Postprandial" is a term that is well known to a person skilled in the art of diabetology. The term "postprandial" describes in particular the phase after a meal or/and exposure to glucose under experimental conditions. In a healthy person this phase is characterised by an increase and subsequent decrease in blood glucose concentration. The term "postprandial" or "postprandial phase" typically ends up to 2 h after a meal or/and exposure to glucose.

The subject to be treated as disclosed herein may have a fasting plasma glucose concentration of at least 8 mmol/L, at least 8.5 mmol/L or at least 9 mmol/L. These plasma glucose concentrations exceed normoglycemic concentrations.

In another aspect of the present invention, the combination as described herein can be used for improving (i.e. reducing) fasting plasma glucose in a patient suffering from diabetes type 2. Reduction means in particular that the plasma glucose concentration reaches normoglycemic values or at least approaches these values.

The combination of the present invention can be used in the treatment of one or more of the medical indications described herein, for example in treatment of diabetes type 2 patients, or for conditions associated with diabetes type 2, such as improvement of glycemic control, reduction of the fasting plasma glucose concentration, for the improvement of glucose excursion, reduction of the postprandial plasma glucose concentration, improvement of glucose tolerance, improving the $HbA_{1c}$ value, weight loss or/and prevention of weight gain.

In the present invention, desPro$^{36}$Exendin-4(1-39)-Lys$_6$-NH$_2$ or/and the pharmaceutically acceptable salt thereof may be administered to a subject in need thereof, in an amount sufficient to induce a therapeutic effect.

In the present invention, desPro$^{36}$Exendin-4(1-39)-Lys$_6$-NH$_2$ or/and the pharmaceutically acceptable salt thereof may be formulated with suitable pharmaceutically acceptable carriers, adjuvants, or/and auxiliary substances.

The compound desPro$^{36}$Exendin-4(1-39)-Lys$_6$-NH$_2$ or/and a pharmaceutically acceptable salt thereof may be administered parenterally, e.g. by injection (such as by intramuscular or by subcutaneous injection). Suitable injection devices, for instance the so-called "pens" comprising a cartridge comprising the active ingredient, and an injection needle, are known. The compound desPro$^{36}$Exendin-4(1-39)-Lys$_6$-NH$_2$ or/and a pharmaceutically acceptable salt thereof may be administered in a suitable amount, for instance in an amount in the range of 10 to 15 µg per dose or 15 to 20 µg per dose.

In the present invention, desPro$^{36}$Exendin-4(1-39)-Lys$_6$-NH$_2$ or/and a pharmaceutically acceptable salt thereof may be administered in a daily dose in the range of 10 to 20 µg, in the range of 10 to 15 µg, or in the range of 15 to 20 µg. DesPro$^{36}$Exendin-4(1-39)-Lys$_6$-NH$_2$ or/and a pharmaceutically acceptable salt thereof may be administered by one injection per day.

In the present invention, desPro$^{36}$Exendin-4(1-39)-Lys$_6$-NH$_2$ or/and a pharmaceutically acceptable salt thereof may be provided in a liquid composition. The skilled person knows liquid compositions of AVE0010 suitable for parenteral administration. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition comprising desPro$^{36}$Exendin-4(1-39)-Lys$_6$-NH$_2$ or/and a pharmaceutically acceptable salt thereof may comprise a suitable preservative. A suitable preservative may be selected from phenol, m-cresol, benzyl alcohol and p-hydroxybenzoic acid ester. A preferred preservative is m-cresol.

The liquid composition comprising desPro$^{36}$Exendin-4(1-39)-Lys$_6$-NH$_2$ or/and a pharmaceutically acceptable salt thereof may comprise a tonicity agent. A suitable tonicity agent may be selected from glycerol, lactose, sorbitol, mannitol, glucose, NaCl, calcium or magnesium containing compounds such as CaCl$_2$. The concentration of glycerol, lactose, sorbitol, mannitol and glucose may be in the range of 100-250 mM. The concentration of NaCl may be up to 150 mM. A preferred tonicity agent is glycerol.

The liquid composition comprising desPro$^{36}$Exendin-4(1-39)-Lys$_6$-NH$_2$ or/and a pharmaceutically acceptable salt thereof may comprise methionine from 0.5 µg/mL to 20 µg/mL, preferably from 1 µg/ml to 5 µg/ml. Preferably, the liquid composition comprises L-methionine.

A further aspect of the present invention is a method for inducing weight loss in diabetes type 2 patients or/and for preventing weight gain in diabetes type 2 patients, said method comprising administering desPro$^{36}$Exendin-4(1-39)-Lys$_6$-NH$_2$ or/and a pharmaceutically acceptable salt thereof, in combination with metformin to a subject in need thereof. In particular, the combination as described herein may be administered. In the method of the present invention, the subject may be the subject defined herein.

Yet another aspect of the present invention refers to the use of the combination as described herein for the manufacture of a medicament for the treatment of a medical indication, as described herein. For example, the combination as described herein can be used for the manufacture of a medicament for inducing weight loss in diabetes type 2 patients or/and for preventing weight gain in diabetes type 2 patients. The combination of the present invention can also be used for the manufacture of a medicament for the treatment of diabetes type 2 patients, or for the treatment of conditions associated with diabetes type 2, such as improvement of glycemic control, reduction of the fasting plasma glucose concentration, for the improvement of glucose excursion, reduction of the postprandial plasma glucose concentration, improving the $HbA_{1c}$ value, or/and improvement of glucose tolerance. The medicament can be formulated as described herein. For example the medicament can comprise a parenteral formulation of AVE0010 or/and a pharmaceutically acceptable salt thereof, and an oral formulation of metformin or/and a pharmaceutically acceptable salt thereof.

The invention is further illustrated by the following example and figures.

FIGURE LEGENDS

Example 1

FIG. 1: Study design

FIG. 2: The overall step-down testing procedure

FIG. 3: Kaplan-Meier plot of time to treatment discontinuation due to any reason—Randomized population FIG. 4: Plot of mean change in HbA1c (%) from baseline by visit during the main 24-week treatment period—mITT population FIG. 5: Plot of mean change in fasting plasma glucose (mmol/L) from baseline by visit during the main 24-week treatment period—mITT population FIG. 6: Plot of mean change in body weight (kg) from baseline by visit during the main 24-week treatment period—mITT population FIG. 7: Plot of mean change in HbA1c (%) from baseline by visit and at endpoint—mITT population FIG. 8: Plot of mean change in fasting plasma glucose (mmol/L) from baseline by visit and at endpoint—mITT population FIG. 9: Plot of mean change in body weight (kg) from baseline by visit and at endpoint—mITT population Example 2

FIG. 10—Study Design

FIG. 11—Kaplan-Meier plot of time to treatment discontinuation due to any reason—Randomized population FIG. 12—Plot of responders (patients with HbA1c<7% and weight loss of >5% of baseline body weight) by visits at endpoint—mITT population FIG. 13—Plot of mean change in HbA1C (%) from baseline by visit at endpoint—mITT population FIG. 14—Plot of HbA1c responders (<6.5% or <7% respectively) at selected visits and at endpoint—mITT population FIG. 15—Plot of mean change in body weight (kg) from baseline by visit and at endpoint—mITT population FIG. 16—Plot of mean change in fasting plasma glucose (mmol/L) from baseline by visit and at endpoint—mITT population

EXAMPLE 1

A Randomized, Double-Blind, Placebo-Controlled, Parallel-Group, Multicenter, Multinational Study Assessing the Efficacy and Safety of Lixisenatide in Comparison to Placebo as an Add-on Treatment to Metformin in Patients with Type 2 Diabetes Summary The Example refers to a randomized, double-blind, placebo-controlled, parallel-group, multicenter, multinational study assessing the efficacy and safety of lixisenatide in comparison to placebo as an add-on treatment to metformin in patients with type 2 diabetes: The approximate minimum study duration per patient was 79 weeks (up to 3 weeks screening+24-week main treatment+variable extension+3 days follow-up). The study was conducted in 75 centers in 15 countries. The primary objective of this study was to assess the effects of lixisenatide as an add-on treatment to metformin on glycemic control using a two-step dose titration regimen in comparison to placebo in terms of $HbA_{1c}$ reduction (absolute change) over a period of 24 weeks.

A total of 484 patients were randomized to one of the four treatment groups (161 in the lixisenatide two-step titration group, 161 in the lixisenatide one-step titration group, 80 in the placebo two-step titration group, and 82 in the placebo one-step titration group). Of the 484 randomized patients, 482 patients were exposed to the study treatment. Two patients (1 in each placebo group) were randomized by mistake and were not exposed to any study treatment. Both patients were excluded from both the efficacy and safety analyses. The placebo one-step and two-step titration groups were combined in the analyses. Demographics and baseline characteristics were generally similar across treatment groups, except that the placebo-treated patients are slightly older than the lixisenatide-treated patients. Out of the 482 randomized and treated patients, 5 patients (1 patient in the lixisenatide two-step titration group, 3 patients in the lixisenatide one-step titration group, and 1 patient in the placebo one-step titration group) were excluded from the mITT population for efficacy analyses due to lack of post-baseline efficacy data During the overall study treatment period, 103 (21.3%) patients prematurely discontinued the study treatment. The percentage of patients who discontinued the study treatment was higher in the lixisenatide two-step titration group (24.8%) than in the lixisenatide one-step titration group (18.6%) and in the combined placebo group (20.4%). For the lixisenatide-treated groups, the main reason for treatment discontinuation was "adverse events" (11.8% for lixisenatide two-step titration and 8.7% for lixisenatide one-step titration, versus 6.2% for combined placebo), followed by "other reasons" (9.9% and 7.5%, versus 9.9% for combined placebo).

The least squared (LS) mean changes from baseline to Week 24 in $HbA_{1c}$ were −0.83% for the lixisenatide two-step titration group (LS mean difference vs. combined placebo=−0.41%; p-value <0.0001), −0.92% for the lixisenatide one-step titration group (LS mean difference vs. combined placebo=−0.49%; p-value <0.0001), compared to −0.42% for the combined placebo group. The percentage of patients reaching $HbA_{1c} \leq 6.5$ or <7% at week 24 was significantly higher in both lixisenatide-treated groups than in the placebo-treated group (for $HbA_{1c} \leq 6.5\%$, 20.4% for lixisenatide two-step titration and 25.6% for lixisenatide one-step titration, versus 7.6% for the combined placebo; for $HbA_{1c} < 7\%$, 42.1% for lixisenatide two-step titration and 47.4% for lixisenatide one-step titration, versus 24.1% for the combined placebo). Both lixisenatide-treated groups demonstrated a statistically significant decrease in fasting plasma glucose compared with the combined placebo group (for the lixisenatide two-step titration group, LS mean difference=−0.67 mmol/L and p-value=0.0004; for the lixisenatide one-step titration group, LS mean difference=−0.65 mmol/L and p-value=0.0007). A statistically significant decrease in body weight from baseline to Week 24 was also demonstrated in both lixisenatide-treated groups, compared with the combined placebo group (for lixisenatide two-step titration, LS mean difference=−1.05 kg and p-value 0.0025; for lixisenatide one-step titration, LS mean difference=−1.00 kg and p-value 0.0042). Both lixisenatide-treated groups showed slightly lower percentages of patients requiring rescue therapy during the main 24-week double-blind treatment period (3.1% for two-step titration and 1.3% for one-step titration), compared with the combined placebo group (4.4%). There was no evidence for significant difference between each lixisenatide group and the combined placebo group due to the low incidence of rescued patients.

Lixisenatide was well tolerated. The incidence of treatment emergent adverse events (TEAEs) was comparable across treatment groups (87.6% in the lixisenatide two-step titration group, 85.7% in the lixisenatide one-step titration group, and 86.3% in the combined placebo group). Five patients (1 patient in the lixisenatide two-step titration group, 2 patients in the lixisenatide one-step titration group, and 2 patients in the combined placebo group) had TEAEs during the on-treatment period leading to death. Fifty nine patients had at least one serious TEAEs occurring during the on-treatment period for the whole study with a similar incidence rate between the lixisenatide two-step titration group (13.0%) and the combined placebo group (13.8%), but a slightly lower incidence rate in the lixisenatide one-step titration group (9.9%). The most commonly reported TEAE for lixisenatide-treated patients was nausea (62 [38.5%] patients for two-step titration and 47 [29.2%] for one-step titration, versus 13 [8.1%] for the combined placebo) followed by vomiting (29 [18.0%] patients for two-step titration and 21 [13.0%] for one-step titration, versus 1 [0.6%] for the combined placebo). Twelve (7.5%) patients in the lixisenatide two-step titration group and 6 (3.7%) patients in the lixisenatide one-step titration group had symptomatic hypoglycemia events per protocol definition during the on-treatment period for the whole study, compared with 12 (7.5%) placebo-treated patients who had symptomatic hypoglycemia events during the same period. None of the symptomatic hypoglycemia events was severe in intensity. A total of 15 patients (6 [3.7%] for lixisenatide two-step titration, 3 [1.9%] for lixisenatide one-step titration, and 6 [3.8%] for combined placebo) had reported allergic events that were adjudicated as an allergic reaction by the Allergic Reaction Assessment Committee (ARAC) but only 2 of the allergic events (1 in each lixisenatide group) were adjudicated as possibly related to the investigational product. No case of acute pancreatitis was observed in the study. There was no relevant difference in terms of safety and tolerability between the 2 titration regimens (one-step and two-step) for lixisenatide.

Objectives

Primary Objective

The primary objective of this study was to assess the effects of lixisenatide as an add-on treatment to metformin on glycemic control using a two-step dose titration regimen in comparison to placebo in terms of HbA1c reduction (absolute change) over a period of 24 weeks in patients with type 2 diabetes.

Secondary Objective(s)

The secondary objectives of this study were:

To assess the effects of AVE0010 on:
Glycemic control in comparison to placebo in terms of $HbA_{1c}$ reduction when it is used in a one-step dose titration regimen,
Percentage of patients reaching $HbA_{1c} < 7\%$ or $HbA_{1c} \leq 6.5\%$,
Body weight,
Fasting plasma glucose,
To assess AVE0010 safety and tolerability,
To assess AVE0010 PK and anti-AVE0010 antibody development.

Trial Design

This was a randomized, double-blind, placebo-controlled, 4-arm, unbalanced design, parallel-group, multicenter, multinational study: two-step titration (150 lixisenatide treated and 75 placebo treated patients) and one-step titration (150 lixisenatide treated and 75 placebo treated patients). The study was double-blind with regard to active and placebo treatments. The study drug volume (i.e. dose of active drug or matching placebo) and the titration regimens (i.e. one-step and two-step) were not blinded.

The patients were stratified by screening values of HbA1c (<8%, ≥8%) and Body Mass Index (BMI <30 kg/m², ≥30 kg/m²). After a screening period, patients were centrally randomized via interactive voice response system (IVRS) in a 2:1:2:1 ratio to one of the four arms (lixisenatide two-step titration, placebo two-step titration, lixisenatide one-step titration, and placebo one-step titration).

Per the protocol amendment 4 (dated on 19 Jan. 2010), the approximate minimum study duration per patient was 79 weeks (up to 3 weeks screening+24 weeks main double-blind treatment+variable double-blind treatment extension+3 days follow-up). Patients who completed the 24-week main double-blind period underwent a variable double-blind treatment extension period, which ended for all patients approximately at the scheduled date of week 76 visit (V24) for the last randomized patient.

Patients who prematurely discontinued the study treatment were continued in the study up to the scheduled date of study completion according to the protocol amendment 3 (dated on 3 Jul. 2009). They were followed up according to the study procedures as specified in the protocol amendment (except 3-day safety post-treatment follow-up, pharmacokinetics assessment, and meal challenge test).

Primary and Key Secondary Endpoints

Primary Endpoint

The primary efficacy variable was the absolute change in $HbA_{1c}$ from baseline to week 24, which was defined as: $HbA_{1c}$ at week 24—$HbA_{1c}$ at baseline.

If a patient discontinued the treatment prematurely or received rescue therapy during the main 24-week double-blind treatment period or did not have $HbA_{1c}$ value at week 24 visit, the last post-baseline $HbA_{1c}$ measurement during the main 24-week double-blind on-treatment period was used as $HbA_{1c}$ value at week 24 (Last Observation Carried Forward [LOCF] procedure).

Secondary Endpoints

Efficacy Endpoints

For secondary efficacy variables, the same procedure for handling missing assessment/early discontinuation was applied as for the primary variable.

Continuous Variables

Change in PPG (mmol/L) from baseline to Week 24
Change in body weight (kg) from baseline to Week 24

Categorical Variables

Percentage of patients with $HbA_{1c} < 7\%$ at Week 24
Percentage of patients with $HbA_{1c} < 6.5\%$ at Week 24
Percentage of patients requiring rescue therapy during the main 24-week double-blind treatment period
Percentage of patients with ≥5% weight loss (kg) from baseline to Week 24

Safety Endpoints

The safety analysis was based on the reported TEAEs and other safety information including symptomatic hypoglycemia and severe symptomatic hypoglycemia, local tolerability at injection site, allergic events (as adjudicated by ARAC), suspected pancreatitis, increased calcitonin, vital signs, 12-lead ECG and laboratory tests. Major cardiovascular events were also collected and adjudicated by a Cardiovascular Adjudication Committee (CAC). The adjudicated and confirmed events by CAC from this study and other lixisenatide phase 2-3 studies will be pooled for analyses and summarized in a separate report based on the statistical analysis plan for the overall cardiovascular assessment of lixisenatide. The KRM/CSR will not present the summary of the adjudicated and confirmed CV events from this study.

Sample Size Calculation Assumptions

The sample size/power calculations were performed based on the primary efficacy variable, absolute change from baseline to week 24 in $HbA_{1c}$.

150 patients for one lixisenatide arm and 2×75 patients for combined placebo group provided a powers of 91% (or 75%) to detect a difference of 0.5% (or 0.4%) in the absolute change from baseline to week 24 in HbA1c between lixisenatide and placebo, assuming the common standard deviation is 1.3% with a 2-sided test at the 5% significance level. The sample size calculations were based upon the 2-sample t-test and made using nQuery® Advisor 5.0. Standard deviation was estimated in a conservative manner from previously conducted diabetes studies (based on published data of similarly designed study and on internal data, not published), taking into account early dropout.

Statistical Methods

Analysis Populations

The modified intent-to-treat (mITT) population consisted of all randomized patients who received at least one dose of double-blind investigational product (IP), and had both a baseline assessment and at least one post-baseline assessment of efficacy variables.

The safety population was defined as all randomized patients who took at least one dose of the double-blind W.

Primary Efficacy Analysis

The primary endpoint (change in $HbA_{1c}$ from baseline to week 24) was analyzed using an analysis of covariance (ANCOVA) model with treatment groups (lixisenatide two-step titration and placebo arms, lixisenatide one-step titration and placebo arms), randomization strata of screening $HbA_{1c}$ (<8.0, ≥8.0%), randomization strata of screening BMI (<30, ≥30 kg/m²), and country as fixed effects and using the baseline $HbA_{1G}$ value as a covariate. Difference between each lixisenatide arm and placebo combined group and two-sided 95% confidence interval as wells as p-value were estimated within the framework of ANCOVA. In the ANCOVA model, the two titration placebo arms were included as separate treatment levels, but they were combined as one group when making comparisons using appropriate contrast (eg, to compare lixisenatide two-step titration with placebo combined [−0.5, −0.5, 0, 1] in the order of placebo one-step titration, placebo two-step titration, lixisenatide one-step titration and lixisenatide two-step titration).

A stepwise testing procedure was applied in order to ensure type I error control. First, lixisenatide two-step titration arm was compared with the placebo combined group (primary objective). If the test was statistically significant, then lixisenatide one-step titration arm was compared with the placebo combined group (secondary objective).

The primary analysis of the primary efficacy variable was performed based on the mITT population and the measurements obtained during the main 24-week double-blind on-treatment period for efficacy variables. The main 24-week double-blind on-treatment period for efficacy variables was defined as the time from the first dose of the double-blind IP up to 3 days (except for FPG by central laboratory, which was up to 1 day) after the last dose of the double-blind IP injection on or before V12/Week 24 visit (or D169 if V12/Week 24 visit was missing), or up to the introduction of the rescue therapy, whichever was the earliest. The LOCF procedure was used by taking this last available post-baseline on-treatment $HbA_{1c}$ measurement (before the initiation of the new medication in the event of rescue therapy) as the $HbA_{1c}$ value at week 24.

Secondary Efficacy Analysis

Once the primary variable was statistically significant at α=0.05 for both comparisons, the testing procedure was performed to test the following secondary efficacy variables by the following prioritized order:

Change in fasting plasma glucose (FPG) (mmol/L) from baseline to Week 24,

Change in body weight (kg) from baseline to Week 24,

Percentage of patients requiring rescue therapy during the main 24-week double-blind treatment period.

A diagram that provides a detailed description of this overall step-down testing procedure is shown in FIG. 2.

All continuous secondary efficacy variables at week 24 as described in Section 3.2.1 were analyzed using the similar approach and ANCOVA model as described in Section 5.2 for the primary analysis of the primary efficacy variable. The adjusted estimates of the treatment mean difference between each lixisenatide arm and the placebo combined group and two-sided 95% confidence intervals were provided.

The following categorical secondary efficacy variables at Week 24 were analyzed using a Cochran-Mantel-Haenszel (CMH) method stratified on randomization strata (screening $HbA_{1c}$ [<8.0, ≥8%] and screening BMI (<30 kg/m$^2$, ≥30 kg/m$^2$) values):

Percentage of patients with $HbA_{1c}$<7.0% at Week 24,

Percentage of patients with $HbA_{1c}$≥6.5% at Week 24,

Percentage of patients requiring rescue therapy during the main 24-week double-blind treatment period.

Number and percentage of patients with ≥5% weight loss from baseline at week 24 were presented by treatment groups.

All secondary endpoints at the end of treatment were only evaluated by descriptive statistics (mean, standard deviation, median and ranges provided in CSR).

Safety Analysis

The safety analyses were primarily based on the on-treatment period for the whole study. The on-treatment period for the whole study was defined as the time from the first dose of double-blind IP up to 3 days after the last dose of IP administration during the whole study period regardless of rescue status. The 3-day interval was chosen based on the half-life of the IP (approximately 5 times the half-life).

In addition, the safety analyses for the 24-week double-blind treatment period will be summarized in the CSR.

The summary of safety results (descriptive statistics or frequency tables) is presented by treatment groups.

Results

Study Patients

Patient Accountability

The study was conducted in 75 centers in 15 countries (Brazil, Chile, Colombia, Estonia, Germany, Italy, Lithuania, Malaysia, Mexico, Philippines, Poland, Romania, Slovakia, Ukraine and United States). A total of 884 patients were screened and 484 were randomized to one of the four treatment arms (161 in the lixisenatide two-step titration group, 161 in the lixisenatide one-step titration group, 80 in the placebo two-step titration group, and 82 in the placebo one-step titration group,). The main reason for screening failure was $HbA_{1c}$ value at the screening visit out of the defined protocol ranges (257 [29.1%] out of 884 screened patients).

Of the 484 randomized patients, 482 patients were exposed to the study treatment and included in the analysis. Two patients (1 in each placebo group) were randomized by mistake and were not exposed to any study treatment. Both patients were excluded from both the efficacy and safety analyses. Out of the 482 randomized and treated patients, 5 patients (1 patient in the lixisenatide two-step titration group, 3 patients in the lixisenatide one-step titration group, and 1 patient in the placebo one-step titration group) were excluded from mITT population for efficacy analyses due to lack of post-baseline efficacy data. Table 1 provides the number of patients included in each analysis population.

TABLE 1

Analysis populations - Randomized population

| | Placebo | | | Lixisenatide | | | |
|---|---|---|---|---|---|---|---|
| | Two-step Titration | One-step Titration | Combined | Two-step Titration | One-step Titration | Combined | All |
| Randomized population | 80 (100%) | 82 (100%) | 162 (100%) | 161 (100%) | 161 (100%) | 322 (100%) | 484 (100%) |
| Efficacy population Modified Intent-to-Treat (mITT) | 79 (98.8%) | 80 (97.6%) | 159 (98.1%) | 160 (99.4%) | 158 (98.1%) | 318 (98.8%) | 477 (98.6%) |
| Safety population | 79 | 81 | 160 | 161 | 161 | 322 | 482 |

PK = pharmacokinetics.
Note:
The safety and PK population patients are tabulated according to treatment actually received (as treated). For the efficacy population, patients are tabulated according to their randomized treatment (as randomized).

Study Disposition

Table 2 provides the summary of patient disposition for each treatment group. During the overall treatment period, 103 (21.3%) patients prematurely discontinued the study treatment. The percentage of patients who discontinued the study treatment was higher in the lixisenatide two-step titration group (24.8%) than in the lixisenatide one-step titration group (18.6%) and in the combined placebo group (20.4%).

For the lixisenatide-treated groups, the main reason for treatment discontinuation was "adverse events" (11.8% for lixisenatide two-step titration and 8.7% for lixisenatide one-step titration, versus 6.2% for combined placebo), followed by "other reasons" (9.9% and 7.5%, versus 9.9% for combined placebo). Similar results were observed for the main 24-week treatment period, where a total of 40 (8.3%) patients prematurely discontinued the study treatment with the main reason also being adverse events for the lixisenatide-treated groups (6.8% for two-step titration and 5.0% for one-step titration, versus 1.9% for the combined placebo). The time-to-onset of treatment discontinuation due to any reason for the overall treatment period is depicted in FIG. 3. Similar discontinuation trends were observed between the two lixisenatide groups during the first 6 months, compared with a slightly lower discontinuation rate in the combined placebo group. After 6 months, lixisenatide one-step titration group showed a similar trend as the combined placebo group, whereas the lixisenatide two-step titration still maintained a higher rate.

Of 4 placebo-treated two-step titration patients who discontinued the treatment due to an AE (Table 2), one had a missing last administration date on the "End of treatment" CRF and discontinued the treatment due to the AEs that were classified as post-treatment AEs according to the SAP data handling convention, while 3 had TEAEs leading to treatment discontinuation (Table 16).

TABLE 2

Patient disposition - Randomized population

| | Placebo | | | Lixisenatide | | |
|---|---|---|---|---|---|---|
| | Two-step Titration (N = 80) | One-step Titration (N = 82) | Combined (N = 162) | Two-step Titration (N = 161) | One-step Titration (N = 161) | Combined (N = 322) |
| Randomized and not treated | 1 (1.3%) | 1 (1.2%) | 2 (1.2%) | 0 | 0 | 0 |
| Subject's request for not treated | 0 | 1 (1.2%) | 1 (0.6%) | 0 | 0 | 0 |
| Reason for not treated | 1 (1.3%) | 1 (1.2%) | 2 (1.2%) | 0 | 0 | 0 |
| Adverse event | 0 | 0 | 0 | 0 | 0 | 0 |
| Lack of efficacy | 0 | 0 | 0 | 0 | 0 | 0 |
| Poor compliance to protocol | 0 | 0 | 0 | 0 | 0 | 0 |
| Lost to follow-up | 0 | 0 | 0 | 0 | 0 | 0 |
| Other reasons | 1 (1.3%) | 1 (1.2%) | 2 (1.2%) | 0 | 0 | 0 |
| Randomized and treated | 79 (98.8%) | 81 (98.8%) | 160 (98.8%) | 161 (100%) | 161 (100%) | 322 (100%) |
| Did not complete 24-week double-blind study treatment | 1 (1.3%) | 8 (9.8%) | 9 (5.6%) | 17 (10.6%) | 14 (8.7%) | 31 (9.6%) |
| Subject's request for 24-week treatment discontinuation | 0 | 8 (9.8%) | 8 (4.9%) | 15 (9.3%) | 10 (6.2%) | 25 (7.8%) |
| Reason for 24-week treatment discontinuation | 1 (1.3%) | 8 (9.8%) | 9 (5.6%) | 17 (10.6%) | 14 (8.7%) | 31 (9.6%) |
| Adverse event | 1 (1.3%) | 2 (2.4%) | 3 (1.9%) | 11 (6.8%) | 8 (5.0%) | 19 (5.9%) |
| Lack of efficacy | 0 | 1 (1.2%) | 1 (0.6%) | 1 (0.6%) | 1 (0.6%) | 2 (0.6%) |
| Poor compliance to protocol | 0 | 0 | 0 | 1 (0.6%) | 0 | 1 (0.3%) |
| Lost to follow-up | 0 | 0 | 0 | 0 | 0 | 0 |
| Other reasons | 0 | 5 (6.1%) | 5 (3.1%) | 4 (2.5%) | 5 (3.1%) | 9 (2.8%) |
| Did not complete double-blind study treatment | 12 (15.0%) | 21 (25.6%) | 33 (20.4%) | 40 (24.8%) | 30 (18.6%) | 70 (21.7%) |
| Subject's request for treatment discontinuation | 9 (11.3%) | 16 (19.5%) | 25 (15.4%) | 31 (19.3%) | 23 (14.3%) | 54 (16.8%) |
| Reason for study treatment discontinuation | 12 (15.0%) | 21 (25.6%) | 33 (20.4%) | 40 (24.8%) | 30 (18.6%) | 70 (21.7%) |
| Adverse event | 4 (5.0%) | 6 (7.3%) | 10 (6.2%) | 19 (11.8%) | 14 (8.7%) | 33 (10.2%) |
| Lack of efficacy | 1 (1.3%) | 4 (4.9%) | 5 (3.1%) | 3 (1.9%) | 2 (1.2%) | 5 (1.6%) |
| Poor compliance to protocol | 1 (1.3%) | 1 (1.2%) | 2 (1.2%) | 2 (1.2%) | 2 (1.2%) | 4 (1.2%) |
| Lost to follow-up | 0 | 0 | 0 | 0 | 0 | 0 |
| Other reasons | 6 (7.5%) | 10 (12.2%) | 16 (9.9%) | 16 (9.9%) | 12 (7.5%) | 28 (8.7%) |
| Status at last study contact | 80 (100%) | 82 (100%) | 162 (100%) | 161 (100%) | 161 (100%) | 322 (100%) |
| Alive | 79 (98.8%) | 80 (97.6%) | 159 (98.1%) | 160 (99.4%) | 158 (98.1%) | 318 (98.8%) |
| Dead | 1 (1.3%) | 2 (2.4%) | 3 (1.9%) | 1 (0.6%) | 2 (1.2%) | 3 (0.9%) |
| Lost to follow-up | 0 | 0 | 0 | 0 | 1 (0.6%) | 1 (0.3%) |

Note:
Percentages are calculated using the number of randomized patients as denominator.

Demographics and Baseline Characteristics

The demographic and patient baseline characteristics were generally similar across treatment groups for the safety population (Table 3), except that the placebo-treated patients were slightly older than the lixiseantide-treated patients. The median age of the study population was 57.0 years. The majority of the patients were Caucasian/White (90.2%).

Disease characteristics including diabetic history were generally comparable across treatment groups, except that the mean age at onset of type 2 diabetes is slightly higher in the placebo-treated patients than the lixiseantide-treated patients (Table 4).

$HbA_{1c}$, FPG, and body weight at baseline were generally comparable across treatment groups for the safety population (Table 5).

TABLE 3

Demographics and patient characteristics at screening or baseline - Safety population

| | Placebo | | | Lixisenatide | | | |
|---|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) | All (N = 482) |
| Age (years) | | | | | | | |
| Number | 79 | 81 | 160 | 161 | 161 | 322 | 482 |
| Mean (SD) | 58.9 (8.8) | 57.5 (10.8) | 58.2 (9.8) | 54.6 (8.9) | 55.4 (8.9) | 55.0 (8.9) | 56.1 (9.3) |
| Median | 58.0 | 59.0 | 58.0 | 55.0 | 57.0 | 56.0 | 57.0 |
| Min:Max | 40:79 | 29:77 | 29:79 | 24:73 | 34:73 | 24:73 | 24:79 |
| Age Group (years) [n (%)] | | | | | | | |
| Number | 79 | 81 | 160 | 161 | 161 | 322 | 482 |
| <50 | 9 (11.4%) | 17 (21.0%) | 26 (16.3%) | 45 (28.0%) | 45 (28.0%) | 90 (28.0%) | 116 (24.1%) |
| ≥50 to <65 | 47 (59.5%) | 43 (53.1%) | 90 (56.3%) | 102 (63.4%) | 96 (59.6%) | 198 (61.5%) | 288 (59.8%) |
| ≥65 to <75 | 19 (24.1%) | 17 (21.0%) | 36 (22.5%) | 14 (8.7%) | 20 (12.4%) | 34 (10.6%) | 70 (14.5%) |
| ≥75 | 4 (5.1%) | 4 (4.9%) | 8 (5.0%) | 0 | 0 | 0 | 8 (1.7%) |
| Gender [n (%)] | | | | | | | |
| Number | 79 | 81 | 160 | 161 | 161 | 322 | 482 |
| Male | 36 (45.6%) | 36 (44.4%) | 72 (45.0%) | 72 (44.7%) | 71 (44.1%) | 143 (44.4%) | 215 (44.6%) |
| Female | 43 (54.4%) | 45 (55.6%) | 88 (55.0%) | 89 (55.3%) | 90 (55.9%) | 179 (55.6%) | 267 (55.4%) |
| Race [n (%)] | | | | | | | |
| Number | 79 | 81 | 160 | 161 | 161 | 322 | 482 |
| Caucasian/White | 72 (91.1%) | 76 (93.8%) | 148 (92.5%) | 146 (90.7%) | 141 (87.6%) | 287 (89.1%) | 435 (90.2%) |
| Black | 0 | 1 (1.2%) | 1 (0.6%) | 2 (1.2%) | 1 (0.6%) | 3 (0.9%) | 4 (0.8%) |
| Asian/Oriental | 5 (6.3%) | 4 (4.9%) | 9 (5.6%) | 11 (6.8%) | 13 (8.1%) | 24 (7.5%) | 33 (6.8%) |
| Other | 2 (2.5%) | 0 | 2 (1.3%) | 2 (1.2%) | 6 (3.7%) | 8 (2.5%) | 10 (2.1%) |
| Ethnicity [n (%)] | | | | | | | |
| Number | 79 | 81 | 160 | 161 | 161 | 322 | 482 |
| Hispanic | 24 (30.4%) | 22 (27.2%) | 46 (28.8%) | 55 (34.2%) | 44 (27.3%) | 99 (30.7%) | 145 (30.1%) |
| Not Hispanic | 55 (69.6%) | 59 (72.8%) | 114 (71.3%) | 106 (65.8%) | 117 (72.7%) | 223 (69.3%) | 337 (69.9%) |
| Screening HbA1c (%) | | | | | | | |
| Number | 79 | 81 | 160 | 161 | 161 | 322 | 482 |
| Mean (SD) | 8.15 (0.83) | 8.15 (0.85) | 8.15 (0.84) | 8.20 (0.87) | 8.13 (0.82) | 8.17 (0.85) | 8.16 (0.84) |
| Median | 8.00 | 8.00 | 8.00 | 8.10 | 8.00 | 8.05 | 8.00 |
| Min:Max | 7.0:10.0 | 7.0:10.0 | 7.0:10.0 | 7.0:10.0 | 7.0:9.8 | 7.0:10.0 | 7.0:10.0 |
| Randomization strata of screening HbA1c (%) [n (%)] | | | | | | | |
| Number | 79 | 81 | 160 | 161 | 161 | 322 | 482 |
| <8 | 38 (48.1%) | 39 (48.1%) | 77 (48.1%) | 77 (47.8%) | 78 (48.4%) | 155 (48.1%) | 232 (48.1%) |
| ≥8 | 41 (51.9%) | 42 (51.9%) | 83 (51.9%) | 84 (52.2%) | 83 (51.6%) | 167 (51.9%) | 250 (51.9%) |

TABLE 3-continued

Demographics and patient characteristics at screening or baseline - Safety population

|  | Placebo | | | Lixisenatide | | | |
|---|---|---|---|---|---|---|---|
|  | Two-step Titration (N = 79) | One-step Titration (N = 81) | Combined (N = 160) | Two-step Titration (N = 161) | One-step Titration (N = 161) | Combined (N = 322) | All (N = 482) |
| Screening BMI (kg/m$^2$) | | | | | | | |
| Number | 79 | 81 | 160 | 161 | 161 | 322 | 482 |
| Mean (SD) | 32.52 | 32.41 | 32.47 | 32.09 | 33.12 | 32.60 | 32.56 |
|  | (4.97) | (5.91) | (5.45) | (4.82) | (5.82) | (5.36) | (5.39) |
| Median | 31.43 | 31.56 | 31.53 | 31.39 | 32.83 | 32.13 | 31.84 |
| Min:Max | 24.8:48.2 | 22.8:57.5 | 22.8:57.5 | 21.9:45.7 | 21.8:55.3 | 21.8:55.3 | 21.8:57.5 |
| Randomization strata of screening BMI (kg/m$^2$) [n (%)] | | | | | | | |
| Number | 79 | 81 | 160 | 161 | 161 | 322 | 482 |
| <30 | 28 | 28 | 56 | 56 | 56 | 112 | 168 |
|  | (35.4%) | (34.6%) | (35.0%) | (34.8%) | (34.8%) | (34.8%) | (34.9%) |
| ≥30 | 51 | 53 | 104 | 105 | 105 | 210 | 314 |
|  | (64.6%) | (65.4%) | (65.0%) | (65.2%) | (65.2%) | (65.2%) | (65.1%) |
| Baseline BMI (kg/m$^2$) | | | | | | | |
| Number | 79 | 81 | 160 | 161 | 161 | 322 | 482 |
| Mean (SD) | 32.38 | 32.35 | 32.37 | 32.06 | 32.99 | 32.53 | 32.47 |
|  | (5.04) | (5.86) | (5.45) | (4.84) | (5.80) | (5.36) | (5.38) |
| Median | 31.37 | 31.45 | 31.39 | 31.37 | 32.53 | 31.99 | 31.76 |
| Min:Max | 23.8:48.0 | 22.9:56.2 | 22.9:56.2 | 21.9:45.8 | 22.0:55.4 | 21.9:55.4 | 21.9:56.2 |
| Baseline BMI Categories (kg/m$^2$) [n (%)] | | | | | | | |
| Number | 79 | 81 | 160 | 161 | 161 | 322 | 482 |
| <30 | 29 | 29 | 58 | 59 | 57 | 116 | 174 |
|  | (36.7%) | (35.8%) | (36.3%) | (36.6%) | (35.4%) | (36.0%) | (36.1%) |
| ≥30 | 50 | 52 | 102 | 102 | 104 | 206 | 308 |
|  | (63.3%) | (64.2%) | (63.8%) | (63.4%) | (64.6%) | (64.0%) | (63.9%) |

BMI = Body Mass Index.

TABLE 4

Disease characteristics at screening or baseline - Safety population

|  | Placebo | | | Lixisenatide | | | |
|---|---|---|---|---|---|---|---|
|  | Two-step Titration (N = 79) | One-step Titration (N = 81) | Combined (N = 160) | Two-step Titration (N = 161) | One-step Titration (N = 161) | Combined (N = 322) | All (N = 482) |
| Duration of diabetes (years) | | | | | | | |
| Number | 79 | 81 | 160 | 161 | 161 | 322 | 482 |
| Mean (SD) | 6.68 (5.33) | 5.77 (4.00) | 6.22 (4.71) | 6.01 (4.60) | 5.77 (3.85) | 5.89 (4.24) | 6.00 (4.40) |
| Median | 5.31 | 4.58 | 4.92 | 5.25 | 5.04 | 5.15 | 5.05 |
| Min:Max | 0.6:23.4 | 1.0:18.7 | 0.6:23.4 | 0.5:22.5 | 0.5:17.2 | 0.5:22.5 | 0.5:23.4 |
| Age at onset of type 2 diabetes (years) | | | | | | | |
| Number | 79 | 81 | 160 | 161 | 161 | 322 | 482 |
| Mean (SD) | 52.3 (8.9) | 51.8 (10.6) | 52.0 (9.8) | 48.6 (9.1) | 49.7 (8.7) | 49.1 (8.9) | 50.1 (9.3) |
| Median | 52.0 | 52.0 | 52.0 | 50.0 | 51.0 | 50.0 | 51.0 |
| Min:Max | 25:75 | 21:72 | 21:75 | 12:70 | 27:70 | 12:70 | 12:75 |
| Duration of metformin treatment (years) | | | | | | | |
| Number | 79 | 81 | 160 | 161 | 161 | 322 | 482 |
| Mean (SD) | 4.01 (3.46) | 3.20 (2.60) | 3.60 (3.07) | 3.70 (3.37) | 3.26 (2.58) | 3.48 (3.01) | 3.52 (3.03) |
| Median | 3.18 | 2.25 | 2.64 | 2.68 | 2.31 | 2.49 | 2.56 |
| Min:Max | 0.3:18.9 | 0.4:13.9 | 0.3:18.9 | 0.3:21.0 | 0.3:12.0 | 0.3:21.0 | 0.3:21.0 |

TABLE 4-continued

Disease characteristics at screening or baseline - Safety population

|  | Placebo | | | Lixisenatide | | | |
|---|---|---|---|---|---|---|---|
|  | Two-step Titration (N = 79) | One-step Titration (N = 81) | Combined (N = 160) | Two-step Titration (N = 161) | One-step Titration (N = 161) | Combined (N = 322) | All (N = 482) |
| Daily dose of metformin at baseline (mg/day) | | | | | | | |
| Number | 79 | 81 | 160 | 161 | 161 | 322 | 482 |
| Mean (SD) | 1878.2 (344.3) | 2005.6 (439.2) | 1942.7 (399.1) | 2035.7 (427.4) | 1967.7 (404.3) | 2001.7 (416.7) | 1982.1 (411.5) |
| Median | 1700.0 | 2000.0 | 1700.0 | 2000.0 | 1700.0 | 2000.0 | 1700.0 |
| Min:Max | 1500:2550 | 1500:3400 | 1500:3400 | 1500:3000 | 1500:3000 | 1500:3000 | 1500:3400 |
| Categorized daily dose of metformin at baseline (mg/day) [n (%)] | | | | | | | |
| Number | 79 | 81 | 160 | 161 | 161 | 322 | 482 |
| <1500 | 0 | 0 | 0 | 0 | 0 | 0 | 0 |
| ≥1500-<2500 | 66 (83.5%) | 58 (71.6%) | 124 (77.5%) | 111 (68.9%) | 119 (73.9%) | 230 (71.4%) | 354 (73.4%) |
| ≥2500-<3000 | 13 (16.5%) | 20 (24.7%) | 33 (20.6%) | 43 (26.7%) | 39 (24.2%) | 82 (25.5%) | 115 (23.9%) |
| ≥3000 | 0 | 3 (3.7%) | 3 (1.9%) | 7 (4.3%) | 3 (1.9%) | 10 (3.1%) | 13 (2.7%) |
| History of gestational diabetes [n (%)] | | | | | | | |
| Number (Female) | 43 | 45 | 88 | 89 | 90 | 179 | 267 |
| Yes (Female) | 0 | 1 (2.2%) | 1 (1.1%) | 2 (2.2%) | 8 (8.9%) | 10 (5.6%) | 11 (4.1%) |
| No (Female) | 43 (100%) | 44 (97.8%) | 87 (98.9%) | 87 (97.8%) | 82 (91.1%) | 169 (94.4%) | 256 (95.9%) |
| Prior use of GLP-1 receptor agonist [n (%)] | | | | | | | |
| Number | 79 | 81 | 160 | 161 | 161 | 322 | 482 |
| Yes | 1 (1.3%) | 0 | 1 (0.6%) | 0 | 0 | 0 | 1 (0.2%) |
| No | 78 (98.7%) | 81 (100%) | 159 (99.4%) | 161 (100%) | 161 (100%) | 322 (100%) | 481 (99.8%) |
| Diabetic retinopathy [n (%)] | | | | | | | |
| Number | 79 | 81 | 160 | 160 | 161 | 321 | 481 |
| Yes | 2 (2.5%) | 3 (3.7%) | 5 (3.1%) | 13 (8.1%) | 10 (6.2%) | 23 (7.2%) | 28 (5.8%) |
| No | 63 (79.7%) | 62 (76.5%) | 125 (78.1%) | 131 (81.9%) | 131 (81.4%) | 262 (81.6%) | 387 (80.5%) |
| Unknown | 14 (17.7%) | 16 (19.8%) | 30 (18.8%) | 16 (10.0%) | 20 (12.4%) | 36 (11.2%) | 66 (13.7%) |
| Diabetic sensory or motor neuropathy [n (%)] | | | | | | | |
| Number | 79 | 81 | 160 | 160 | 161 | 321 | 481 |
| Yes | 19 (24.1%) | 16 (19.8%) | 35 (21.9%) | 34 (21.3%) | 35 (21.7%) | 69 (21.5%) | 104 (21.6%) |
| No | 57 (72.2%) | 64 (79.0%) | 121 (75.6%) | 124 (77.5%) | 124 (77.0%) | 248 (77.3%) | 369 (76.7%) |
| Unknown | 3 (3.8%) | 1 (1.2%) | 4 (2.5%) | 2 (1.3%) | 2 (1.2%) | 4 (1.2%) | 8 (1.7%) |
| Diabetic autonomic neuropathy [n (%)] | | | | | | | |
| Number | 79 | 81 | 160 | 160 | 161 | 321 | 481 |
| Yes | 2 (2.5%) | 0 | 2 (1.3%) | 1 (0.6%) | 0 | 1 (0.3%) | 3 (0.6%) |
| No | 68 (86.1%) | 72 (88.9%) | 140 (87.5%) | 148 (92.5%) | 148 (91.9%) | 296 (92.2%) | 436 (90.6%) |
| Unknown | 9 (11.4%) | 9 (11.1%) | 18 (11.3%) | 11 (6.9%) | 13 (8.1%) | 24 (7.5%) | 42 (8.7%) |
| Diabetic nephropathy [n (%)] | | | | | | | |
| Number | 79 | 81 | 160 | 160 | 161 | 321 | 481 |
| Yes | 4 (5.1%) | 4 (4.9%) | 8 (5.0%) | 5 (3.1%) | 3 (1.9%) | 8 (2.5%) | 16 (3.3%) |
| Microalbuminuria | 3 (3.8%) | 4 (4.9%) | 7 (4.4%) | 4 (2.5%) | 3 (1.9%) | 7 (2.2%) | 14 (2.9%) |
| Overt proteinuria | 1 (1.3%) | 0 | 1 (0.6%) | 1 (0.6%) | 0 | 1 (0.3%) | 2 (0.4%) |
| Impaired renal function | 0 | 0 | 0 | 0 | 0 | 0 | 0 |
| Dialysis or transplantation | 0 | 0 | 0 | 0 | 0 | 0 | 0 |
| No | 69 (87.3%) | 67 (82.7%) | 136 (85.0%) | 146 (91.3%) | 145 (90.1%) | 291 (90.7%) | 427 (88.8%) |
| Unknown | 6 (7.6%) | 10 (12.3%) | 16 (10.0%) | 9 (5.6%) | 13 (8.1%) | 22 (6.9%) | 38 (7.9%) |

TABLE 4-continued

Disease characteristics at screening or baseline - Safety population

| | Placebo | | | Lixisenatide | | | |
|---|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) | All (N = 482) |
| Categorized albuminuria at randomization [n (%)] | | | | | | | |
| Number | 9 | 12 | 21 | 14 | 17 | 31 | 52 |
| <3 mg/L (Not reportable) | 0 | 0 | 0 | 1 (7.1%) | 2 (11.8%) | 3 (9.7%) | 3 (5.8%) |
| ≥3 mg/L (Reportable) | 9 (100%) | 12 (100%) | 21 (100%) | 13 (92.9%) | 15 (88.2%) | 28 (90.3%) | 49 (94.2%) |
| <20 mg/L | 7 (77.8%) | 5 (41.7%) | 12 (57.1%) | 6 (42.9%) | 12 (70.6%) | 18 (58.1%) | 30 (57.7%) |
| ≥20-<200 mg/L | 2 (22.2%) | 5 (41.7%) | 7 (33.3%) | 6 (42.9%) | 3 (17.6%) | 9 (29.0%) | 16 (30.8%) |
| ≥200 mg/L | 0 | 2 (16.7%) | 2 (9.5%) | 1 (7.1%) | 0 | 1 (3.2%) | 3 (5.8%) |
| Creatinine clearance (ml/min) at screening | | | | | | | |
| Number | 79 | 81 | 160 | 160 | 159 | 319 | 479 |
| Mean (SD) | 115.64 (33.25) | 122.00 (39.63) | 118.86 (36.64) | 125.34 (41.80) | 129.62 (44.51) | 127.47 (43.16) | 124.59 (41.26) |
| Median | 114.55 | 115.62 | 115.03 | 123.04 | 123.84 | 123.75 | 121.07 |
| Min:Max | 35.8:209.6 | 54.7:263.9 | 35.8:263.9 | 43.5:329.3 | 45.8:360.5 | 43.5:360.5 | 35.8:360.5 |
| Creatinine clearance categories at screening [n (%)] | | | | | | | |
| Number | 79 | 81 | 160 | 160 | 159 | 319 | 479 |
| <30 ml/min (severe renal impairment) | 0 | 0 | 0 | 0 | 0 | 0 | 0 |
| ≥30-<50 ml/min (moderate renal impairment) | 1 (1.3%) | 0 | 1 (0.6%) | 1 (0.6%) | 1 (0.6%) | 2 (0.6%) | 3 (0.6%) |
| ≥50-≤80 ml/min (mild renal impairment) | 10 (12.7%) | 11 (13.6%) | 21 (13.1%) | 21 (13.1%) | 12 (7.5%) | 33 (10.3%) | 54 (11.3%) |
| >80 ml/min (no renal impairment) | 68 (86.1%) | 70 (86.4%) | 138 (86.3%) | 138 (86.3%) | 146 (91.8%) | 284 (89.0%) | 422 (88.1%) |

GLP-1 = Glucagon like peptide-1.
Creatinine clearance value is derived using the equation of Cockcroft and Gault.

TABLE 5

Baseline efficacy variables - Safety population

| | Placebo | | | Lixisenatide | | | |
|---|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) | All (N = 482) |
| HbA1c (%) | | | | | | | |
| Number | 79 | 81 | 160 | 161 | 161 | 322 | 482 |
| Mean (SD) | 8.03 (0.81) | 8.02 (0.84) | 8.03 (0.82) | 8.10 (0.88) | 7.99 (0.87) | 8.05 (0.88) | 8.04 (0.86) |
| Median | 7.90 | 7.90 | 7.90 | 8.00 | 7.80 | 7.90 | 7.90 |
| Min:Max | 6.6:10.3 | 6.2:10.0 | 6.2:10.3 | 6.3:11.4 | 6.2:10.2 | 6.2:11.4 | 6.2:11.4 |
| FPG (mmol/L) | | | | | | | |
| Number | 79 | 81 | 160 | 161 | 161 | 322 | 482 |
| Mean (SD) | 9.60 (2.06) | 9.31 (1.82) | 9.45 (1.94) | 9.54 (2.50) | 9.56 (2.02) | 9.55 (2.27) | 9.52 (2.17) |
| Median | 9.10 | 9.40 | 9.15 | 9.10 | 9.50 | 9.20 | 9.20 |
| Min:Max | 5.8:15.9 | 5.4:14.3 | 5.4:15.9 | 5.1:18.2 | 5.7:17.1 | 5.1:18.2 | 5.1:18.2 |
| Weight (kg) | | | | | | | |
| Number | 79 | 81 | 160 | 161 | 161 | 322 | 482 |
| Mean (SD) | 87.45 (16.32) | 88.28 (18.43) | 87.87 (17.37) | 87.41 (16.90) | 90.21 (18.95) | 88.81 (17.98) | 88.50 (17.77) |

TABLE 5-continued

| | Baseline efficacy variables - Safety population | | | | | | |
|---|---|---|---|---|---|---|---|
| | Placebo | | | Lixisenatide | | | |
| | Two-step Titration (N = 79) | One-step Titration (N = 81) | Combined (N = 160) | Two-step Titration (N = 161) | One-step Titration (N = 161) | Combined (N = 322) | All (N = 482) |
| Median | 84.50 | 86.50 | 85.40 | 86.30 | 87.10 | 86.55 | 86.20 |
| Min:Max | 61.0:145.2 | 51.5:172.0 | 51.5:172.0 | 50.5:140.5 | 55.0:165.0 | 50.5:165.0 | 50.5:172.0 |

FPG = Fasting Plasma Glucose.

Dosage and Duration

The average treatment exposure was similar across treatment groups (552.8 days (79.0 weeks) for combined placebo, 518.6 days (74.1 weeks) for lixisenatide two-step titration, and 538.1 days (76.9 weeks) for lixisenatide one-step titration). Out of 482 safety patients, 439 (93.8% in the combined placebo 2% in the lixisenatide two-step titration group, and 91.3% in the lixisenatide one-step titration group) had at least 169 days (24 weeks) of treatment, and 298 (63.8% in the combined placebo group, 59.0% in the lixisenatide two-step titration group, and 62.7% in the lixisenatide one-step titration group) had at least 547 days (18 months) of treatment. Two patients (1 in each placebo group) had the last administration date on the "End of treatment" CRF missing and hence their treatment durations were set to missing following the SAP data handling convention.

For the lixisenatide two-step titration group, 141 (87.6%) patients were at the target total daily dose of 20 µg at the end of double-blind treatment, at the end of titration and at the end of the 24-week double-blind treatment period (Table 7, Table 8 and Table 9). For the lixisenatide one-step titration group, 147 (91.3%) patients, 150 (93.2%) patients, and 150 (93.2%) patients were at the target total daily dose of 20 µg at the end of double-blind treatment, at the end of titration, and at the end of the 24-week double-blind treatment period, respectively (Table 7, Table 8 and Table 9). For the combined placebo group, 156 (97.5%) patients, 155 (96.9%) patients, and 156 (97.5%) patients were at the target total daily dose 20 µg at the end of double-blind treatment, at the end of titration, and at the end of 24-week double-blind treatment period, respectively (Table 7, Table 8 and Table 9).

TABLE 6

| | Exposure to investigational product - Safety population | | | | | |
|---|---|---|---|---|---|---|
| | Placebo | | | Lixisenatide | | |
| | Two-step Titration (N = 79) | One-step Titration (N = 81) | Combined (N = 160) | Two-step Titration (N = 161) | One-step Titration (N = 161) | Combined (N = 322) |
| Cumulative duration of treatment exposure (patient years) | 123.0 | 116.1 | 239.1 | 228.6 | 237.2 | 465.8 |
| Duration of study treatment (days) | | | | | | |
| Number | 78 | 80 | 158 | 161 | 161 | 322 |
| Mean (SD) | 576.1 (118.8) | 530.1 (179.3) | 552.8 (153.7) | 518.6 (191.4) | 538.1 (172.2) | 528.3 (182.1) |
| Median | 589.0 | 581.5 | 589.0 | 567.0 | 588.0 | 586.5 |
| Min:Max | 182:757 | 2:757 | 2:757 | 6:785 | 1:778 | 1:785 |
| Duration of study treatment by category [n (%)] | | | | | | |
| Missing duration | 1 (1.3%) | 1 (1.2%) | 2 (1.3%) | 0 | 0 | 0 |
| 1-14 days | 0 | 2 (2.5%) | 2 (1.3%) | 2 (1.2%) | 4 (2.5%) | 6 (1.9%) |
| 15-28 days | 0 | 0 | 0 | 4 (2.5%) | 0 | 4 (1.2%) |
| 29-56 days | 0 | 1 (1.2%) | 1 (0.6%) | 3 (1.9%) | 4 (2.5%) | 7 (2.2%) |
| 57-84 days | 0 | 1 (1.2%) | 1 (0.6%) | 2 (1.2%) | 2 (1.2%) | 4 (1.2%) |
| 85-168 days | 0 | 4 (4.9%) | 4 (2.5%) | 8 (5.0%) | 4 (2.5%) | 12 (3.7%) |
| 169-364 days | 6 (7.6%) | 4 (4.9%) | 10 (6.3%) | 7 (4.3%) | 4 (2.5%) | 11 (3.4%) |
| 365-546 days | 18 (22.8%) | 20 (24.7%) | 38 (23.8%) | 40 (24.8%) | 42 (26.1%) | 82 (25.5%) |
| 547-728 days | 48 (60.8%) | 44 (54.3%) | 92 (57.5%) | 87 (54.0%) | 95 (59.0%) | 182 (56.5%) |
| >728 days | 6 (7.6%) | 4 (4.9%) | 10 (6.3%) | 8 (5.0%) | 6 (3.7%) | 14 (4.3%) |
| Cumulative duration of study treatment by category [n (%)] | | | | | | |
| Missing duration | 1 (1.3%) | 1 (1.2%) | 2 (1.3%) | 0 | 0 | 0 |
| ≥1 day | 78 (98.7%) | 80 (98.8%) | 158 (98.8%) | 161 (100%) | 161 (100%) | 322 (100%) |
| ≥15 days | 78 (98.7%) | 78 (96.3%) | 156 (97.5%) | 159 (98.8%) | 157 (97.5%) | 316 (98.1%) |
| ≥29 days | 78 (98.7%) | 78 (96.3%) | 156 (97.5%) | 155 (96.3%) | 157 (97.5%) | 312 (96.9%) |
| ≥57 days | 78 (98.7%) | 77 (95.1%) | 155 (96.9%) | 152 (94.4%) | 153 (95.0%) | 305 (94.7%) |
| ≥85 days | 78 (98.7%) | 76 (93.8%) | 154 (96.3%) | 150 (93.2%) | 151 (93.8%) | 301 (93.5%) |
| ≥169 days | 78 (98.7%) | 72 (88.9%) | 150 (93.8%) | 142 (88.2%) | 147 (91.3%) | 289 (89.8%) |

TABLE 6-continued

Exposure to investigational product - Safety population

|  | Placebo | | | Lixisenatide | | |
|---|---|---|---|---|---|---|
|  | Two-step Titration (N = 79) | One-step Titration (N = 81) | Combined (N = 160) | Two-step Titration (N = 161) | One-step Titration (N = 161) | Combined (N = 322) |
| ≥365 days | 72 (91.1%) | 68 (84.0%) | 140 (87.5%) | 135 (83.9%) | 143 (88.8%) | 278 (86.3%) |
| ≥547 days | 54 (68.4%) | 48 (59.3%) | 102 (63.8%) | 95 (59.0%) | 101 (62.7%) | 196 (60.9%) |
| ≥729 days | 6 (7.6%) | 4 (4.9%) | 10 (6.3%) | 8 (5.0%) | 6 (3.7%) | 14 (4.3%) |

Duration of exposure = (date of the last double-blind investigational product injection − date of the first double-blind investigational product injection) + 1.

TABLE 7

Number (%) of patients by final total daily dose at the end of the double-blind treatment - Safety population

| Final dose | Placebo | | | Lixisenatide | | |
|---|---|---|---|---|---|---|
|  | Two-step Titration (N = 79) | One-step Titration (N = 81) | Combined (N = 160) | Two-step Titration (N = 161) | One-step Titration (N = 161) | Combined (N = 322) |
| 10 μg | 1 (1.3%) | 3 (3.7%) | 4 (2.5%) | 7 (4.3%) | 13 (8.1%) | 20 (6.2%) |
| 15 μg | 0 | 0 | 0 | 13 (8.1%) | 1 (0.6%) | 14 (4.3%) |
| 20 μg | 78 (98.7%) | 78 (96.3%) | 156 (97.5%) | 141 (87.6%) | 147 (91.3%) | 288 (89.4%) |

Dose = Dose of active drug or volume-matched placebo.
Note:
Percentages are calculated using the number of safety patients as the denominator.

TABLE 8

Number (%) of patients by dose at the end of titration - Safety population

| Dose at the end of titration | Placebo | | | Lixisenatide | | |
|---|---|---|---|---|---|---|
|  | Two-step Titration (N = 79) | One-step Titration (N = 81) | Combined (N = 160) | Two-step Titration (N = 161) | One-step Titration (N = 161) | Combined (N = 322) |
| 10 μg | 0 | 4 (4.9%) | 4 (2.5%) | 4 (2.5%) | 11 (6.8%) | 15 (4.7%) |
| 15 μg | 1 (1.3%) | 0 | 1 (0.6%) | 16 (9.9%) | 0 | 16 (5.0%) |
| 20 μg | 78 (98.7%) | 77 (95.1%) | 155 (96.9%) | 141 (87.6%) | 150 (93.2%) | 291 (90.4%) |

Dose = Dose of active drug or volume-matched placebo.
The scheduled visit for end of titration per protocol would be Visit 5/Week 2.
Note:
Percentages are calculated using the number of safety patients as the denominator.

TABLE 9

Number (%) of patients by final total daily dose at the end of the 24-week treatment - Safety population

| Dose at the end of the 24-week | Placebo | | | Lixisenatide | | |
|---|---|---|---|---|---|---|
|  | Two-step Titration (N = 79) | One-step Titration (N = 81) | Combined (N = 160) | Two-step Titration (N = 161) | One-step Titration (N = 161) | Combined (N = 322) |
| 10 μg | 0 | 3 (3.7%) | 3 (1.9%) | 6 (3.7%) | 11 (6.8%) | 17 (5.3%) |
| 15 μg | 1 (1.3%) | 0 | 1 (0.6%) | 14 (8.7%) | 0 | 14 (4.3%) |
| 20 μg | 78 (98.7%) | 78 (96.3%) | 156 (97.5%) | 141 (87.6%) | 150 (93.2%) | 291 (90.4%) |

Dose = Dose of active drug or volume-matched placebo.
Note:
Percentages are calculated using the number of safety patients as the denominator.

Efficacy
Primary Efficacy Endpoint
Main Analysis

Table 10 summarizes the results of the primary efficacy parameter, change from baseline to Week 24 (LOCF) in $HbA_{1c}$ using an ANCOVA analysis.

The pre-specified primary analysis showed that both lixisenatide-treated groups demonstrated statistically significant reduction of $HbA_{1c}$ from Baseline to Week 24, compared to the combined placebo group (for the lixisenatide two-step titration group, LS mean difference=−0.41%; p-value <0.0001; for the lixisenatide one-step titration group, LS mean difference=−0.49%; p-value <0.0001).

TABLE 10

Mean change in $HbA_{1c}$ (%) from baseline to Week 24 - mITT population

| | | Lixisenatide | |
|---|---|---|---|
| HbA1c (%) | Placebo Combined (N = 159) | Two-step Titration (N = 160) | One-step Titration (N = 158) |
| Baseline | | | |
| Number | 158 | 152 | 156 |
| Mean (SD) | 8.03 (0.83) | 8.12 (0.89) | 7.99 (0.88) |
| Median | 7.90 | 8.00 | 7.80 |
| Min:Max | 6.2:10.3 | 6.3:11.4 | 6.2:10.2 |
| Week 24 (LOCF) | | | |
| Number | 158 | 152 | 156 |
| Mean (SD) | 7.63 (0.92) | 7.27 (1.00) | 7.13 (0.85) |
| Median | 7.60 | 7.10 | 7.00 |
| Min:Max | 5.9:10.7 | 5.5:11.5 | 5.3:9.6 |
| Change from baseline to Week 24 (LOCF) | | | |
| Number | 158 | 152 | 156 |
| Mean (SD) | −0.40 (0.85) | −0.85 (0.93) | −0.86 (0.86) |
| Median | −0.40 | −0.80 | −0.80 |
| Min:Max | −3.1:2.2 | −4.0:2.4 | −3.8:1.3 |
| LS Mean (SE)[a] | −0.42 (0.099) | −0.83 (0.099) | −0.92 (0.101) |
| LS Mean difference (SE) vs. placebo combined[a] | — | −0.41 (0.089) | −0.49 (0.090) |
| 95% CI | — | (−0.583 to −0.232) | (−0.670 to −0.317) |
| p-value | | <0.0001 | <0.0001 |

LOCF = Last observation carried forward.
[a]Analysis of covariance (ANCOVA) model with treatment groups (two-step titration lixisenatide and placebo arms, one-step titration lixisenatide and placebo arms), randomization strata of screening HbA1c (<8.0, ≥8.0%), randomization strata of screening body mass index (<30, ≥30 kg/m²), and country as fixed effects and baseline HbA1c value as a covariate. The comparison between each lixisenatide group and the placebo combined group was achieved through appropriate contrasts.
Note:
The analysis included measurements obtained before the introduction of rescue medication and up to 3 days after the last dose of the double-blind investigational product injection on or before Visit 12 (Week 24), or Day 169 if Visit 12 (Week 24) is not available.
Patients with both baseline and Week 24 (LOCF) measurements are included.

Secondary Analysis

Table 11 summarizes the proportion of patients with treatment response $HbA_{1c}$≤6.5% or <7% at Week 24, respectively. Treatment responses were similar between lixisenatide-treated groups. The analysis of $HbA_{1c}$ responders using the CMH method showed a significant treatment difference between each lixisenatide group versus the combined placebo (for $HbA_1$≤6.5% at Week 24, p-value=0.0009 for lixisenatide two-step titration and p-value <0.0001 for lixisenatide one-step titration; for $HbA_{1c}$<7% at Week 24, p-value=0.0005 for lixisenatide two-step titration and p-value <0.0001 for lixisenatide one-step titration).

TABLE 11

Number (%) of patients with $HbA_{1c}$ value ≤6.5% or <7% respectively at Week 24 - mITT population

| | | Lixisenatide | |
|---|---|---|---|
| HbA1c (%) | Placebo Combined (N = 159) | Two-step Titration (N = 160) | One-step Titration (N = 158) |
| Number | 158 | 152 | 156 |
| ≤6.5% | 12 (7.6%) | 31 (20.4%) | 40 (25.6%) |
| >6.5% | 146 (92.4%) | 121 (79.6%) | 116 (74.4%) |
| p-value vs. Placebo combined[a] | — | 0.0009 | <0.0001 |
| Number | 158 | 152 | 156 |
| <7.0% | 38 (24.1%) | 64 (42.1%) | 74 (47.4%) |
| ≥7.0% | 120 (75.9%) | 88 (57.9%) | 82 (52.6%) |
| p-value vs. Placebo combined[a] | — | 0.0005 | <0.0001 |

[a]Cochran-Mantel-Haenszel (CMH) method stratified by randomization strata of screening HbA1c (<8.0 or ≥8.0%) and randomization strata of screening body mass index (<30 or ≥30 kg/m²).
Note:
The analysis included measurements obtained before the introduction of rescue medication and up to 3 days after the last dose of the double-blind investigational product injection on or before Visit 12 (Week 24), or Day 169 if Visit 12 (Week 24) is not available.

Secondary Efficacy Endpoints

Table 12 and Table 13 summarize the ANCOVA analyses of FPG and body weight, respectively. FIG. 5 and FIG. 6 illustrate the mean (±SE) change from baseline in FPG and body weight over time during the main 24-week double blind treatment period, respectively. Mean (±SE) change from baseline in FPG and body weight over time up to Week 76 are depicted in FIG. 8 and FIG. 9 in the appendix, respectively.

For FPG, both lixisenatide-treated groups showed a statistically significant decrease from baseline to Week 24 compared with the combined placebo group (for the lixisenatide two-step titration group, LS mean difference=−0.67 mmol/L and p-value=0.0004; for the lixisenatide one-step titration group, LS mean difference=−0.65 mmol/L and p-value=0.0007)

The LS mean body weight change from baseline at week 24 was −2.68 kg for the lixisenatide two-step titration group, −2.63 kg for the lixisenatide one-step titration group, and −1.63 kg for the combined placebo group, with statistically significant differences observed in both lixisenatide-treated groups compared with the combined placebo group (for lixisenatide two-step titration, LS mean difference=−1.05 kg and p-value 0.0025; for lixisenatide one-step titration, LS mean difference=−1.00 kg and p-value 0.0042).

TABLE 12

Mean change in fasting plasma glucose (mmol/L) from baseline to Week 24 - mITT population

| | | Lixisenatide | |
|---|---|---|---|
| Fasting plasma glucose (mmol/L) | Placebo Combined (N = 159) | Two-step Titration (N = 160) | One-step Titration (N = 158) |
| Baseline | | | |
| Number | 158 | 160 | 158 |
| Mean (SD) | 9.46 (1.95) | 9.52 (2.50) | 9.55 (2.04) |
| Median | 9.15 | 9.05 | 9.45 |
| Min:Max | 5.4:15.9 | 5.1:18.2 | 5.7:17.1 |

TABLE 12-continued

Mean change in fasting plasma glucose (mmol/L) from baseline to Week 24 - mITT population

|  | Placebo Combined (N = 159) | Lixisenatide Two-step Titration (N = 160) | Lixisenatide One-step Titration (N = 158) |
|---|---|---|---|
| Fasting plasma glucose (mmol/L) | | | |
| Week 24 (LOCF) | | | |
| Number | 158 | 160 | 158 |
| Mean (SD) | 9.10 (1.99) | 8.40 (2.08) | 8.44 (1.90) |
| Median | 8.90 | 8.10 | 8.25 |
| Min:Max | 5.0:17.5 | 3.9:17.8 | 4.9:15.5 |
| Change from baseline to Week 24 (LOCF) | | | |
| Number | 158 | 160 | 158 |
| Mean (SD) | −0.36 (1.88) | −1.13 (2.20) | −1.10 (2.21) |
| Median | −0.30 | −0.90 | −0.90 |
| Min:Max | −6.0:6.0 | −12.2:7.4 | −11.1:6.9 |
| LS Mean (SE)[a] | 0.11 (0.209) | −0.56 (0.208) | −0.53 (0.212) |
| LS Mean difference (SE) vs. placebo combined[a] | — | −0.67 (0.187) | −0.65 (0.189) |
| 95% CI | — | (−1.035 to −0.301) | (−1.019 to −0.275) |
| p-value | | 0.0004 | 0.0007 |

LOCF = Last observation carried forward.

[a]Analysis of covariance (ANCOVA) model with treatment groups (two-step titration lixisenatide and placebo arms, one-step titration lixisenatide and placebo arms), randomization strata of screening HbA1c (<8.0, ≥8.0%), randomization strata of screening body mass index (<30, ≥30 kg/m$^2$), and country as fixed effects and baseline fasting plasma glucose as a covariate. The comparison between each lixisenatide group and the placebo combined group was achieved through appropriate contrasts.

Note:
The analysis included measurements obtained before the introduction of rescue medication and up to 1 day after the last dose of the double-blind investigational product injection on or before Visit 12 (Week 24), or Day 169 if Visit 12 (Week 24) is not available.
Patients with both baseline and Week 24 (LOCF) measurements are included.

TABLE 13

Mean change in body weight (kg) from baseline to Week 24 - mITT population

|  | Placebo Combined (N = 159) | Lixisenatide Two-step Titration (N = 160) | Lixisenatide One-step Titration (N = 158) |
|---|---|---|---|
| Body weight (kg) | | | |
| Baseline | | | |
| Number | 158 | 155 | 158 |
| Mean (SD) | 87.86 (17.31) | 88.08 (16.77) | 90.30 (19.01) |
| Median | 85.40 | 87.80 | 87.55 |
| Min:Max | 51.5:172.0 | 58.2:140.5 | 55.0:165.0 |
| Week 24 (LOCF) | | | |
| Number | 158 | 155 | 158 |
| Mean (SD) | 86.25 (17.35) | 85.42 (16.80) | 87.68 (18.67) |
| Median | 83.50 | 85.10 | 84.55 |
| Min:Max | 48.6:172.0 | 56.5:139.0 | 52.0:154.0 |
| Change from baseline to Week 24 (LOCF) | | | |
| Number | 158 | 155 | 158 |
| Mean (SD) | −1.61 (3.05) | −2.66 (2.80) | −2.62 (3.25) |
| Median | −1.40 | −2.40 | −2.17 |
| Min:Max | −11.4:8.9 | −12.8:5.8 | −16.9:8.0 |
| LS Mean (SE)[a] | −1.63 (0.385) | −2.68 (0.385) | −2.63 (0.389) |
| LS Mean difference (SE) vs. placebo combined[a] | — | −1.05 (0.345) | −1.00 (0.349) |
| 95% CI | — | (−1.727 to −0.371) | (−1.687 to −0.317) |
| p-value | | 0.0025 | 0.0042 |

LOCF = Last observation carried forward.

[a]Analysis of covariance (ANCOVA) model with treatment groups (two-step titration lixisenatide and placebo arms, one-step titration lixisenatide and placebo arms), randomization strata of screening HbA1c (<8.0, ≥8.0%), randomization strata of screening body mass index (<30, ≥30 kg/m$^2$), and country as fixed effects and baseline body weight as a covariate. The comparison between each lixisenatide group and the placebo combined group was achieved through appropriate contrasts.

Note:
The analysis included measurements obtained before the introduction of rescue medication and up to 3 days after the last dose of the double-blind investigational product injection on or before Visit 12 (Week 24), or Day 169 if Visit 12 (Week 24) is not available.
Patients with both baseline and Week 24 (LOCF) measurements are included.

25.8% lixisenatide-treated two-step titration patients, 19.6% lixisenatide-treated one-step titration patients, and 15.2% placebo-treated patients had ≥5% weight loss from baseline to week 24 (Table 14). Body weight continued to decrease after the 24 week main treatment period in both lixisenatide-treated groups FIG. 9.

TABLE 14

Number (%) of patients with >=5% weight loss from baseline to week 24 - mITT population

| Weight loss | Placebo Combined (N = 159) | Lixisenatide Two-step Titration (N = 160) | Lixisenatide One-step Titration (N = 158) |
|---|---|---|---|
| Number | 158 | 155 | 158 |
| ≥5% | 24 (15.2%) | 40 (25.8%) | 31 (19.6%) |
| <5% | 134 (84.8%) | 115 (74.2%) | 127 (80.4%) |

Note:
The analysis included measurements obtained before the introduction of rescue medication and up to 3 days after the last dose of the double-blind investigational product injection on or before Visit 12 (Week 24), or Day 169 if Visit 12 (Week 24) is not available.
Patients with both baseline and Week 24 (LOCF) measurements are included.

Both lixisenatide-treated groups showed slightly lower percentages of patients requiring rescue therapy during the main 24-week double-blind treatment period (3.1% for two-step titration and 1.3% for one-step titration), compared with the combined placebo group (4.4%) (Table 15). There was no evidence for significant differences between each lixisenatide group and the combined placebo group due to the low incidence of rescued patients during the main 24-week double-blind treatment period.

TABLE 15

Number (%) of patients requiring rescue therapy during the 24-week treatment period - mITT population

| Requiring rescue therapy | Placebo Combined (N = 159) | Lixisenatide Two-step Titration (N = 160) | Lixisenatide One-step Titration (N = 158) |
|---|---|---|---|
| Number | 159 | 160 | 158 |
| Yes | 7 (4.4%) | 5 (3.1%) | 2 (1.3%) |
| No | 152 (95.6%) | 155 (96.9%) | 156 (98.7%) |
| p-value vs. Placebo combined[a] | — | 0.5499 | 0.0949 |

[a]Cochran-Mantel-Haenszel (CMH) method stratified by randomization strata of screening HbA1c (<8.0 or ≥8.0%) and randomization strata of screening body mass index (<30 or ≥30 kg/m$^2$).

Safety

An overview of the adverse events observed during the on-treatment period for the whole study is provided in Table 16. The proportion of patients who experienced TEAEs was comparable across treatment groups (87.6% in the lixisenatide two-step titration group, 85.7% in the lixisenatide one-step titration group, and 86.3% in the combined placebo group). Five patients (1 patient in the lixisenatide two-step titration group, 2 patients in the lixisenatide one-step titration group, and 2 patients in the combined placebo group) had TEAEs during the on-treatment period leading to death. Fifty nine patients had at lease one serious TEAE occurring during the on-treatment period for the whole study with a similar incidence rate between the lixisenatide two-step titration group (13.0%) and the combined placebo group (13.8%), but a slightly lower incidence rate in the lixisenatide one-step titration group (9.9%). The percentage of patients with TEAEs leading to treatment discontinuation was slightly higher in the lixisenatide-treated groups (11.8% for two-step titration; 8.7% for one-step titration) than in the combined placebo group (5.6%). Between the two lixisenatide groups, a slightly lower rate of TEAEs leading to treatmenmt discontinuation was observed in the one-step titration than in the two-step titration. Table 17, Table 18, and Table 19 summarize TEAEs leading to death, serious TEAEs, and TEAEs leading to treatment discontinuation by primary SOC, HLGT, HLT and PT, respectively. The most common TEAE leading to treatment discontinuation was nausea in both lixisenatide-treated groups (6 [3.7%] patients in each lixisenatide group). No patients discontinued the treatment due to nausea in the combined placebo group.

Table 28 in the appendix presents the incidences of TEAEs during the on-treatment period for the whole study occurring in at least 1% of patients in the combined placebo group or any individual lixisenatide group. Nausea was the most frequently reported TEAE in both lixisenatide-treated groups (62 [38.5%] patients for lixisenatide two-step titration and 47 [29.2%] patients for lixisenatide one-step titration). Thirteen placebo-treated patients (8.1%) reported nausea. The second most frequently reported TEAE in the lixisenatide-treated patients was vomiting (29 [18.0%] patients for lixisenatide two-step titration and 21 [13.0%] patients for lixisenatide one-step titration), followed by headache (23 [14.3%] patients for lixisenatide two-step titration and 20 [12.4%] patients for lixisenatide one-step titration) and diarrhoea (24 [14.9%] patients for lixisenatide two-step titration and 16 [9.9%] patients for lixisenatide one-step titration). The corresponding number of patients (%) in the combined placebo group was 1 (0.6%) for vomiting, 20 (12.5%) for headache, and 21 (13.1%) for diarrhoea.

TABLE 16

Overview of adverse event profile: treatment emergent adverse events during the on-treatment period for the whole study - Safety population

| | Placebo | | | Lixisenatide | | |
| --- | --- | --- | --- | --- | --- | --- |
| | Two-step Titration (N = 79) | One-step Titration (N = 81) | Combined (N = 160) | Two-step Titration (N = 161) | One-step Titration (N = 161) | Combined (N = 322) |
| Patients with any TEAE | 69 (87.3%) | 69 (85.2%) | 138 (86.3%) | 141 (87.6%) | 138 (85.7%) | 279 (86.6%) |
| Patients with any serious TEAE | 13 (16.5%) | 9 (11.1%) | 22 (13.8%) | 21 (13.0%) | 16 (9.9%) | 37 (11.5%) |
| Patients with any TEAE leading to death | 0 | 2 (2.5%) | 2 (1.3%) | 1 (0.6%) | 2 (1.2%) | 3 (0.9%) |
| Patients with any TEAE leading to permanent treatment discontinuation | 3 (3.8%) | 6 (7.4%) | 9 (5.6%) | 19 (11.8%) | 14 (8.7%) | 33 (10.2%) |

TEAE: Treatment Emergent Adverse Event
n (%) = number and percentage of patients with at least one adverse event
Note:
On-treatment period for the whole study = the time from the first dose of double-blind study medication up to 3 days after the last dose administration.

TABLE 17

Number (%) of patients experiencing TEAE(s) leading to death during the overall treatment period by primary SOC, HLGT, HLT, and PT - Safety population

| PRIMARY SYSTEM ORGAN CLASS HLGT: High Level Group Term HLT: High Level Term Preferred Term | Placebo | | | Lixisenatide | | |
| --- | --- | --- | --- | --- | --- | --- |
| | Two-step Titration (N = 79) | One-step Titration (N = 81) | Combined (N = 160) | Two-step Titration (N = 161) | One-step Titration (N = 161) | Combined (N = 322) |
| Any class | 0 | 2 (2.5%) | 2 (1.3%) | 1 (0.6%) | 2 (1.2%) | 3 (0.9%) |
| NEOPLASMS BENIGN, MALIGNANT AND UNSPECIFIED (INCL CYSTS AND POLYPS) | 0 | 0 | 0 | 0 | 1 (0.6%) | 1 (0.3%) |
| HLGT: Gastrointestinal neoplasms malignant and unspecified | 0 | 0 | 0 | 0 | 1 (0.6%) | 1 (0.3%) |

TABLE 17-continued

Number (%) of patients experiencing TEAE(s) leading to death during the overall treatment period by primary SOC, HLGT, HLT, and PT - Safety population

| PRIMARY SYSTEM ORGAN CLASS HLGT: High Level Group Term HLT: High Level Term Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| HLT: Pancreatic neoplasms malignant (excl islet cell and carcinoid) | 0 | 0 | 0 | 0 | 1 (0.6%) | 1 (0.3%) |
| Pancreatic carcinoma | 0 | 0 | 0 | 0 | 1 (0.6%) | 1 (0.3%) |
| NERVOUS SYSTEM DISORDERS | 0 | 1 (1.2%) | 1 (0.6%) | 1 (0.6%) | 1 (0.6%) | 2 (0.6%) |
| HLGT: Central nervous system vascular disorders | 0 | 1 (1.2%) | 1 (0.6%) | 1 (0.6%) | 1 (0.6%) | 2 (0.6%) |
| HLT: Central nervous system haemorrhages and cerebrovascular accidents | 0 | 1 (1.2%) | 1 (0.6%) | 1 (0.6%) | 1 (0.6%) | 2 (0.6%) |
| Cerebrovascular accident | 0 | 1 (1.2%) | 1 (0.6%) | 0 | 1 (0.6%) | 1 (0.3%) |
| Haemorrhagic stroke | 0 | 0 | 0 | 1 (0.6%) | 0 | 1 (0.3%) |
| HLGT: Neurological disorders NEC | 0 | 0 | 0 | 0 | 1 (0.6%) | 1 (0.3%) |
| HLT: Coma states | 0 | 0 | 0 | 0 | 1 (0.6%) | 1 (0.3%) |
| Coma | 0 | 0 | 0 | 0 | 1 (0.6%) | 1 (0.3%) |
| CARDIAC DISORDERS | 0 | 1 (1.2%) | 1 (0.6%) | 0 | 0 | 0 |
| HLGT: Coronary artery disorders | 0 | 1 (1.2%) | 1 (0.6%) | 0 | 0 | 0 |
| HLT: Ischaemic coronary artery disorders | 0 | 1 (1.2%) | 1 (0.6%) | 0 | 0 | 0 |
| Myocardial infarction | 0 | 1 (1.2%) | 1 (0.6%) | 0 | 0 | 0 |
| VASCULAR DISORDERS | 0 | 0 | 0 | 0 | 1 (0.6%) | 1 (0.3%) |
| HLGT: Vascular hypertensive disorders | 0 | 0 | 0 | 0 | 1 (0.6%) | 1 (0.3%) |
| HLT: Vascular hypertensive disorders NEC | 0 | 0 | 0 | 0 | 1 (0.6%) | 1 (0.3%) |
| Hypertension | 0 | 0 | 0 | 0 | 1 (0.6%) | 1 (0.3%) |

TEAE: Treatment Emergent Adverse Event,
SOC: System Organ Class,
HLGT: High Level Group Term,
HLT: High Level Term,
PT: Preferred Term.
MedDRA version: 13.1
n (%) = number and percentage of patients with at least one TEAE leading to death.
Note:
On-treatment period for the whole study = the time from the first dose of double-blind study medication up to 3 days after the last dose administration.
Table sorted by SOC internationally agreed order and HLGT, HLT, PT alphabetic order.

TABLE 18

Number (%) of patients experiencing serious TEAE(s) during the overall treatment period presented by primary SOC, HLGT, HLT, and PT - Safety population

| PRIMARY SYSTEM ORGAN CLASS HLGT: High Level Group Term HLT: High Level Term Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Any class | 13 (16.5%) | 9 (11.1%) | 22 (13.8%) | 21 (13.0%) | 16 (9.9%) | 37 (11.5%) |
| INFECTIONS AND INFESTATIONS | 1 (1.3%) | 3 (3.7%) | 4 (2.5%) | 3 (1.9%) | 2 (1.2%) | 5 (1.6%) |
| HLGT: Infections - pathogen unspecified | 1 (1.3%) | 2 (2.5%) | 3 (1.9%) | 3 (1.9%) | 1 (0.6%) | 4 (1.2%) |
| HLT: Abdominal and gastrointestinal infections | 0 | 0 | 0 | 0 | 1 (0.6%) | 1 (0.3%) |
| Appendicitis | 0 | 0 | 0 | 0 | 1 (0.6%) | 1 (0.3%) |
| HLT: Lower respiratory tract and lung infections | 1 (1.3%) | 2 (2.5%) | 3 (1.9%) | 1 (0.6%) | 0 | 1 (0.3%) |
| Bronchitis | 0 | 1 (1.2%) | 1 (0.6%) | 0 | 0 | 0 |
| Lobar pneumonia | 0 | 0 | 0 | 1 (0.6%) | 0 | 1 (0.3%) |

TABLE 18-continued

Number (%) of patients experiencing serious TEAE(s) during the overall treatment period presented by primary SOC, HLGT, HLT, and PT - Safety population

| PRIMARY SYSTEM ORGAN CLASS<br>HLGT: High Level Group<br>Term<br>HLT: High Level Term<br>Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Pneumonia | 1 (1.3%) | 1 (1.2%) | 2 (1.3%) | 0 | 0 | 0 |
| HLT: Sepsis, bacteraemia, viraemia and fungaemia NEC | 0 | 1 (1.2%) | 1 (0.6%) | 0 | 0 | 0 |
| Septic shock | 0 | 1 (1.2%) | 1 (0.6%) | 0 | 0 | 0 |
| HLT: Skin structures and soft tissue infections | 0 | 0 | 0 | 1 (0.6%) | 0 | 1 (0.3%) |
| Soft tissue infection | 0 | 0 | 0 | 1 (0.6%) | 0 | 1 (0.3%) |
| HLT: Upper respiratory tract infections | 0 | 0 | 0 | 1 (0.6%) | 0 | 1 (0.3%) |
| Peritonsillar abscess | 0 | 0 | 0 | 1 (0.6%) | 0 | 1 (0.3%) |
| HLGT: Viral infectious disorders | 0 | 1 (1.2%) | 1 (0.6%) | 0 | 1 (0.6%) | 1 (0.3%) |
| HLT: Flaviviral infections | 0 | 0 | 0 | 0 | 1 (0.6%) | 1 (0.3%) |
| Dengue fever | 0 | 0 | 0 | 0 | 1 (0.6%) | 1 (0.3%) |
| HLT: Hepatitis viral infections | 0 | 1 (1.2%) | 1 (0.6%) | 0 | 0 | 0 |
| Hepatitis B | 0 | 1 (1.2%) | 1 (0.6%) | 0 | 0 | 0 |
| NEOPLASMS BENIGN, MALIGNANT AND UNSPECIFIED (INCL CYSTS AND POLYPS) | 0 | 0 | 0 | 3 (1.9%) | 3 (1.9%) | 6 (1.9%) |
| HLGT: Breast neoplasms malignant and unspecified (incl nipple) | 0 | 0 | 0 | 1 (0.6%) | 0 | 1 (0.3%) |
| HLT: Breast and nipple neoplasms malignant | 0 | 0 | 0 | 1 (0.6%) | 0 | 1 (0.3%) |
| Breast cancer | 0 | 0 | 0 | 1 (0.6%) | 0 | 1 (0.3%) |
| HLGT: Gastrointestinal neoplasms malignant and unspecified | 0 | 0 | 0 | 0 | 1 (0.6%) | 1 (0.3%) |
| HLT: Pancreatic neoplasms malignant (excl islet cell and carcinoid) | 0 | 0 | 0 | 0 | 1 (0.6%) | 1 (0.3%) |
| Pancreatic carcinoma | 0 | 0 | 0 | 0 | 1 (0.6%) | 1 (0.3%) |
| HLGT: Renal and urinary tract neoplasms malignant and unspecified | 0 | 0 | 0 | 2 (1.2%) | 1 (0.6%) | 3 (0.9%) |
| HLT: Bladder neoplasms malignant | 0 | 0 | 0 | 1 (0.6%) | 0 | 1 (0.3%) |
| Bladder cancer | 0 | 0 | 0 | 1 (0.6%) | 0 | 1 (0.3%) |
| HLT: Urinary tract neoplasms unspecified malignancy NEC | 0 | 0 | 0 | 1 (0.6%) | 1 (0.6%) | 2 (0.6%) |
| Renal neoplasm | 0 | 0 | 0 | 1 (0.6%) | 1 (0.6%) | 2 (0.6%) |
| HLGT: Reproductive neoplasms female malignant and unspecified | 0 | 0 | 0 | 0 | 1 (0.6%) | 1 (0.3%) |
| HLT: Ovarian neoplasms malignant (excl germ cell) | 0 | 0 | 0 | 0 | 1 (0.6%) | 1 (0.3%) |
| Ovarian cancer | 0 | 0 | 0 | 0 | 1 (0.6%) | 1 (0.3%) |
| ENDOCRINE DISORDERS | 0 | 0 | 0 | 1 (0.6%) | 1 (0.6%) | 2 (0.6%) |
| HLGT: Thyroid gland disorders | 0 | 0 | 0 | 1 (0.6%) | 1 (0.6%) | 2 (0.6%) |
| HLT: Thyroid disorders NEC | 0 | 0 | 0 | 1 (0.6%) | 0 | 1 (0.3%) |
| Goitre | 0 | 0 | 0 | 1 (0.6%) | 0 | 1 (0.3%) |
| HLT: Thyroid hypofunction disorders | 0 | 0 | 0 | 0 | 1 (0.6%) | 1 (0.3%) |
| Hypothyroidism | 0 | 0 | 0 | 0 | 1 (0.6%) | 1 (0.3%) |
| METABOLISM AND NUTRITION DISORDERS | 0 | 0 | 0 | 2 (1.2%) | 0 | 2 (0.6%) |
| HLGT: Glucose metabolism disorders (incl diabetes mellitus) | 0 | 0 | 0 | 2 (1.2%) | 0 | 2 (0.6%) |
| HLT: Diabetes mellitus (incl subtypes) | 0 | 0 | 0 | 2 (1.2%) | 0 | 2 (0.6%) |
| Diabetes mellitus | 0 | 0 | 0 | 2 (1.2%) | 0 | 2 (0.6%) |
| PSYCHIATRIC DISORDERS | 0 | 0 | 0 | 1 (0.6%) | 0 | 1 (0.3%) |
| HLGT: Depressed mood disorders and disturbances | 0 | 0 | 0 | 1 (0.6%) | 0 | 1 (0.3%) |

TABLE 18-continued

Number (%) of patients experiencing serious TEAE(s) during the overall treatment period presented by primary SOC, HLGT, HLT, and PT - Safety population

| PRIMARY SYSTEM ORGAN CLASS<br>HLGT: High Level Group<br>Term<br>HLT: High Level Term<br>Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| HLT: Depressive disorders | 0 | 0 | 0 | 1 (0.6%) | 0 | 1 (0.3%) |
| Depression | 0 | 0 | 0 | 1 (0.6%) | 0 | 1 (0.3%) |
| NERVOUS SYSTEM DISORDERS | 0 | 3 (3.7%) | 3 (1.9%) | 3 (1.9%) | 3 (1.9%) | 6 (1.9%) |
| HLGT: Central nervous system vascular disorders | 0 | 3 (3.7%) | 3 (1.9%) | 3 (1.9%) | 1 (0.6%) | 4 (1.2%) |
| HLT: Central nervous system haemorrhages and cerebrovascular accidents | 0 | 3 (3.7%) | 3 (1.9%) | 3 (1.9%) | 1 (0.6%) | 4 (1.2%) |
| Cerebral infarction | 0 | 0 | 0 | 2 (1.2%) | 0 | 2 (0.6%) |
| Cerebrovascular accident | 0 | 1 (1.2%) | 1 (0.6%) | 0 | 1 (0.6%) | 1 (0.3%) |
| Haemorrhagic stroke | 0 | 0 | 0 | 1 (0.6%) | 0 | 1 (0.3%) |
| Ischaemic stroke | 0 | 1 (1.2%) | 1 (0.6%) | 0 | 0 | 0 |
| Ruptured cerebral aneurysm | 0 | 1 (1.2%) | 1 (0.6%) | 0 | 0 | 0 |
| HLGT: Neurological disorders NEC | 0 | 0 | 0 | 0 | 1 (0.6%) | 1 (0.3%) |
| HLT: Coma states | 0 | 0 | 0 | 0 | 1 (0.6%) | 1 (0.3%) |
| Coma | 0 | 0 | 0 | 0 | 1 (0.6%) | 1 (0.3%) |
| HLGT: Peripheral neuropathies | 0 | 0 | 0 | 0 | 2 (1.2%) | 2 (0.6%) |
| HLT: Acute polyneuropathies | 0 | 0 | 0 | 0 | 1 (0.6%) | 1 (0.3%) |
| Polyneuropathy | 0 | 0 | 0 | 0 | 1 (0.6%) | 1 (0.3%) |
| HLT: Chronic polyneuropathies | 0 | 0 | 0 | 0 | 1 (0.6%) | 1 (0.3%) |
| Diabetic neuropathy | 0 | 0 | 0 | 0 | 1 (0.6%) | 1 (0.3%) |
| EYE DISORDERS | 0 | 0 | 0 | 1 (0.6%) | 0 | 1 (0.3%) |
| HLGT: Ocular structural change, deposit and degeneration NEC | 0 | 0 | 0 | 1 (0.6%) | 0 | 1 (0.3%) |
| HLT: Retinal structural change, deposit and degeneration | 0 | 0 | 0 | 1 (0.6%) | 0 | 1 (0.3%) |
| Retinal detachment | 0 | 0 | 0 | 1 (0.6%) | 0 | 1 (0.3%) |
| CARDIAC DISORDERS | 2 (2.5%) | 2 (2.5%) | 4 (2.5%) | 1 (0.6%) | 5 (3.1%) | 6 (1.9%) |
| HLGT: Cardiac arrhythmias | 1 (1.3%) | 1 (1.2%) | 2 (1.3%) | 1 (0.6%) | 2 (1.2%) | 3 (0.9%) |
| HLT: Cardiac conduction disorders | 0 | 0 | 0 | 0 | 1 (0.6%) | 1 (0.3%) |
| Adams-Stokes syndrome | 0 | 0 | 0 | 0 | 1 (0.6%) | 1 (0.3%) |
| HLT: Rate and rhythm disorders NEC | 0 | 1 (1.2%) | 1 (0.6%) | 0 | 0 | 0 |
| Bradycardia | 0 | 1 (1.2%) | 1 (0.6%) | 0 | 0 | 0 |
| HLT: Supraventricular arrhythmias | 1 (1.3%) | 0 | 1 (0.6%) | 1 (0.6%) | 1 (0.6%) | 2 (0.6%) |
| Atrial fibrillation | 1 (1.3%) | 0 | 1 (0.6%) | 1 (0.6%) | 1 (0.6%) | 2 (0.6%) |
| HLGT: Coronary artery disorders | 1 (1.3%) | 1 (1.2%) | 2 (1.3%) | 0 | 4 (2.5%) | 4 (1.2%) |
| HLT: Coronary artery disorders NEC | 1 (1.3%) | 0 | 1 (0.6%) | 0 | 1 (0.6%) | 1 (0.3%) |
| Coronary artery disease | 0 | 0 | 0 | 0 | 1 (0.6%) | 1 (0.3%) |
| Coronary artery stenosis | 1 (1.3%) | 0 | 1 (0.6%) | 0 | 0 | 0 |
| HLT: Ischaemic coronary artery disorders | 0 | 1 (1.2%) | 1 (0.6%) | 0 | 4 (2.5%) | 4 (1.2%) |
| Acute myocardial infarction | 0 | 0 | 0 | 0 | 2 (1.2%) | 2 (0.6%) |
| Angina unstable | 0 | 0 | 0 | 0 | 1 (0.6%) | 1 (0.3%) |
| Myocardial infarction | 0 | 1 (1.2%) | 1 (0.6%) | 0 | 0 | 0 |
| Myocardial ischaemia | 0 | 0 | 0 | 0 | 1 (0.6%) | 1 (0.3%) |
| VASCULAR DISORDERS | 0 | 0 | 0 | 0 | 1 (0.6%) | 1 (0.3%) |
| HLGT: Vascular hypertensive disorders | 0 | 0 | 0 | 0 | 1 (0.6%) | 1 (0.3%) |
| HLT: Vascular hypertensive disorders NEC | 0 | 0 | 0 | 0 | 1 (0.6%) | 1 (0.3%) |
| Hypertension | 0 | 0 | 0 | 0 | 1 (0.6%) | 1 (0.3%) |
| RESPIRATORY, THORACIC AND MEDIASTINAL DISORDERS | 1 (1.3%) | 0 | 1 (0.6%) | 0 | 0 | 0 |
| HLGT: Lower respiratory tract disorders (excl obstruction and infection) | 1 (1.3%) | 0 | 1 (0.6%) | 0 | 0 | 0 |

TABLE 18-continued

Number (%) of patients experiencing serious TEAE(s) during the overall treatment period presented by primary SOC, HLGT, HLT, and PT - Safety population PRIMARY SYSTEM ORGAN CLASS
HLGT: High Level Group
Term
HLT: High Level Term
Preferred Term

| | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| HLT: Pulmonary oedemas | 1 (1.3%) | 0 | 1 (0.6%) | 0 | 0 | 0 |
| Pulmonary oedema | 1 (1.3%) | 0 | 1 (0.6%) | 0 | 0 | 0 |
| GASTROINTESTINAL DISORDERS | 3 (3.8%) | 0 | 3 (1.9%) | 2 (1.2%) | 1 (0.6%) | 3 (0.9%) |
| HLGT: Abdominal hernias and other abdominal wall conditions | 1 (1.3%) | 0 | 1 (0.6%) | 1 (0.6%) | 0 | 1 (0.3%) |
| HLT: Inguinal hernias | 1 (1.3%) | 0 | 1 (0.6%) | 1 (0.6%) | 0 | 1 (0.3%) |
| Inguinal hernia | 1 (1.3%) | 0 | 1 (0.6%) | 1 (0.6%) | 0 | 1 (0.3%) |
| HLGT: Gastrointestinal inflammatory conditions | 1 (1.3%) | 0 | 1 (0.6%) | 0 | 0 | 0 |
| HLT: Gastritis (excl infective) | 1 (1.3%) | 0 | 1 (0.6%) | 0 | 0 | 0 |
| Gastritis | 1 (1.3%) | 0 | 1 (0.6%) | 0 | 0 | 0 |
| HLGT: Gastrointestinal motility and defaecation conditions | 1 (1.3%) | 0 | 1 (0.6%) | 0 | 1 (0.6%) | 1 (0.3%) |
| HLT: Gastrointestinal atonic and hypomotility disorders NEC | 1 (1.3%) | 0 | 1 (0.6%) | 0 | 0 | 0 |
| Constipation | 1 (1.3%) | 0 | 1 (0.6%) | 0 | 0 | 0 |
| HLT: Gastrointestinal spastic and hypermotility disorders | 0 | 0 | 0 | 0 | 1 (0.6%) | 1 (0.3%) |
| Irritable bowel syndrome | 0 | 0 | 0 | 0 | 1 (0.6%) | 1 (0.3%) |
| HLGT: Gastrointestinal signs and symptoms | 0 | 0 | 0 | 1 (0.6%) | 0 | 1 (0.3%) |
| HLT: Nausea and vomiting symptoms | 0 | 0 | 0 | 1 (0.6%) | 0 | 1 (0.3%) |
| Nausea | 0 | 0 | 0 | 1 (0.6%) | 0 | 1 (0.3%) |
| Vomiting | 0 | 0 | 0 | 1 (0.6%) | 0 | 1 (0.3%) |
| HEPATOBILIARY DISORDERS | 1 (1.3%) | 1 (1.2%) | 2 (1.3%) | 0 | 1 (0.6%) | 1 (0.3%) |
| HLGT: Gallbladder disorders | 1 (1.3%) | 1 (1.2%) | 2 (1.3%) | 0 | 1 (0.6%) | 1 (0.3%) |
| HLT: Cholecystitis and cholelithiasis | 1 (1.3%) | 1 (1.2%) | 2 (1.3%) | 0 | 1 (0.6%) | 1 (0.3%) |
| Cholecystitis | 0 | 1 (1.2%) | 1 (0.6%) | 0 | 0 | 0 |
| Cholecystitis acute | 1 (1.3%) | 0 | 1 (0.6%) | 0 | 1 (0.6%) | 1 (0.3%) |
| SKIN AND SUBCUTANEOUS TISSUE DISORDERS | 0 | 0 | 0 | 0 | 1 (0.6%) | 1 (0.3%) |
| HLGT: Epidermal and dermal conditions | 0 | 0 | 0 | 0 | 1 (0.6%) | 1 (0.3%) |
| HLT: Dermatitis and eczema | 0 | 0 | 0 | 0 | 1 (0.6%) | 1 (0.3%) |
| Dermatitis allergic | 0 | 0 | 0 | 0 | 1 (0.6%) | 1 (0.3%) |
| MUSCULOSKELETAL AND CONNECTIVE TISSUE DISORDERS | 3 (3.8%) | 0 | 3 (1.9%) | 2 (1.2%) | 0 | 2 (0.6%) |
| HLGT: Joint disorders | 2 (2.5%) | 0 | 2 (1.3%) | 1 (0.6%) | 0 | 1 (0.3%) |
| HLT: Arthropathies NEC | 1 (1.3%) | 0 | 1 (0.6%) | 0 | 0 | 0 |
| Arthropathy | 1 (1.3%) | 0 | 1 (0.6%) | 0 | 0 | 0 |
| HLT: Osteoarthropathies | 1 (1.3%) | 0 | 1 (0.6%) | 1 (0.6%) | 0 | 1 (0.3%) |
| Osteoarthritis | 1 (1.3%) | 0 | 1 (0.6%) | 1 (0.6%) | 0 | 1 (0.3%) |
| HLGT: Musculoskeletal and connective tissue disorders NEC | 0 | 0 | 0 | 1 (0.6%) | 0 | 1 (0.3%) |
| HLT: Musculoskeletal and connective tissue pain and discomfort | 0 | 0 | 0 | 1 (0.6%) | 0 | 1 (0.3%) |
| Back pain | 0 | 0 | 0 | 1 (0.6%) | 0 | 1 (0.3%) |
| HLGT: Tendon, ligament and cartilage disorders | 1 (1.3%) | 0 | 1 (0.6%) | 0 | 0 | 0 |
| HLT: Cartilage disorders | 1 (1.3%) | 0 | 1 (0.6%) | 0 | 0 | 0 |
| Osteochondrosis | 1 (1.3%) | 0 | 1 (0.6%) | 0 | 0 | 0 |
| INVESTIGATIONS | 0 | 0 | 0 | 1 (0.6%) | 1 (0.6%) | 2 (0.6%) |
| HLGT: Endocrine investigations (incl sex hormones) | 0 | 0 | 0 | 0 | 1 (0.6%) | 1 (0.3%) |
| HLT: Gastrointestinal, pancreatic and APUD hormone analyses | 0 | 0 | 0 | 0 | 1 (0.6%) | 1 (0.3%) |
| Blood calcitonin increased | 0 | 0 | 0 | 0 | 1 (0.6%) | 1 (0.3%) |
| HLGT: Gastrointestinal investigations | 0 | 0 | 0 | 1 (0.6%) | 0 | 1 (0.3%) |

TABLE 18-continued

Number (%) of patients experiencing serious TEAE(s) during the overall treatment period presented by primary SOC, HLGT, HLT, and PT - Safety population

| PRIMARY SYSTEM ORGAN CLASS HLGT: High Level Group | Placebo | | | Lixisenatide | | |
|---|---|---|---|---|---|---|
| Term HLT: High Level Term Preferred Term | Two-step Titration (N = 79) | One-step Titration (N = 81) | Combined (N = 160) | Two-step Titration (N = 161) | One-step Titration (N = 161) | Combined (N = 322) |
| HLT: Digestive enzymes | 0 | 0 | 0 | 1 (0.6%) | 0 | 1 (0.3%) |
| Pancreatic enzymes increased | 0 | 0 | 0 | 1 (0.6%) | 0 | 1 (0.3%) |
| INJURY, POISONING AND PROCEDURAL COMPLICATIONS | 3 (3.8%) | 1 (1.2%) | 4 (2.5%) | 3 (1.9%) | 0 | 3 (0.9%) |
| HLGT: Bone and joint injuries | 2 (2.5%) | 1 (1.2%) | 3 (1.9%) | 2 (1.2%) | 0 | 2 (0.6%) |
| HLT: Limb injuries NEC (incl traumatic amputation) | 0 | 1 (1.2%) | 1 (0.6%) | 0 | 0 | 0 |
| Meniscus lesion | 0 | 1 (1.2%) | 1 (0.6%) | 0 | 0 | 0 |
| HLT: Lower limb fractures and dislocations | 1 (1.3%) | 0 | 1 (0.6%) | 0 | 0 | 0 |
| Ankle fracture | 1 (1.3%) | 0 | 1 (0.6%) | 0 | 0 | 0 |
| HLT: Spinal fractures and dislocations | 1 (1.3%) | 0 | 1 (0.6%) | 0 | 0 | 0 |
| Spinal fracture | 1 (1.3%) | 0 | 1 (0.6%) | 0 | 0 | 0 |
| HLT: Thoracic cage fractures and dislocations | 0 | 0 | 0 | 2 (1.2%) | 0 | 2 (0.6%) |
| Rib fracture | 0 | 0 | 0 | 1 (0.6%) | 0 | 1 (0.3%) |
| Sternal fracture | 0 | 0 | 0 | 1 (0.6%) | 0 | 1 (0.3%) |
| HLT: Upper limb fractures and dislocations | 0 | 0 | 0 | 1 (0.6%) | 0 | 1 (0.3%) |
| Wrist fracture | 0 | 0 | 0 | 1 (0.6%) | 0 | 1 (0.3%) |
| HLGT: Injuries NEC | 0 | 0 | 0 | 3 (1.9%) | 0 | 3 (0.9%) |
| HLT: Non-site specific injuries NEC | 0 | 0 | 0 | 2 (1.2%) | 0 | 2 (0.6%) |
| Fall | 0 | 0 | 0 | 1 (0.6%) | 0 | 1 (0.3%) |
| Multiple injuries | 0 | 0 | 0 | 1 (0.6%) | 0 | 1 (0.3%) |
| HLT: Skin injuries NEC | 0 | 0 | 0 | 1 (0.6%) | 0 | 1 (0.3%) |
| Skin laceration | 0 | 0 | 0 | 1 (0.6%) | 0 | 1 (0.3%) |
| HLGT: Procedural related injuries and complications NEC | 1 (1.3%) | 0 | 1 (0.6%) | 0 | 0 | 0 |
| HLT: Non-site specific procedural complications | 1 (1.3%) | 0 | 1 (0.6%) | 0 | 0 | 0 |
| Incisional hernia | 1 (1.3%) | 0 | 1 (0.6%) | 0 | 0 | 0 |
| SURGICAL AND MEDICAL PROCEDURES | 1 (1.3%) | 0 | 1 (0.6%) | 0 | 0 | 0 |
| HLGT: Vascular therapeutic procedures | 1 (1.3%) | 0 | 1 (0.6%) | 0 | 0 | 0 |
| HLT: Arterial therapeutic procedures (excl aortic) | 1 (1.3%) | 0 | 1 (0.6%) | 0 | 0 | 0 |
| Coronary arterial stent insertion | 1 (1.3%) | 0 | 1 (0.6%) | 0 | 0 | 0 |

TEAE: Treatment Emergent Adverse Event,
SOC: System Organ Class,
HLGT: High Level Group Term,
HLT: High Level Term,
PT: Preferred Term.
MedDRA version: 13.1
n (%) = number and percentage of patients with at least one serious TEAE.
Note:
On-treatment period for the whole study = the time from the first dose of double-blind study medication up to 3 days after the last dose administration.
Table sorted by SOC internationally agreed order and HLGT, HLT, PT alphabetic order.

TABLE 19

Number (%) of patients experiencing TEAE(s) leading to permanent treatment discontinuation during the overall treatment period by primary SOC, HLGT, HLT, and PT - Safety population

| PRIMARY SYSTEM ORGAN CLASS<br>HLGT: High Level Group<br>Term<br>HLT: High Level Term<br>Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Any class | 3 (3.8%) | 6 (7.4%) | 9 (5.6%) | 19 (11.8%) | 14 (8.7%) | 33 (10.2%) |
| INFECTIONS AND INFESTATIONS | 0 | 1 (1.2%) | 1 (0.6%) | 0 | 0 | 0 |
| HLGT: Viral infectious disorders | 0 | 1 (1.2%) | 1 (0.6%) | 0 | 0 | 0 |
| HLT: Hepatitis viral infections | 0 | 1 (1.2%) | 1 (0.6%) | 0 | 0 | 0 |
| Hepatitis B | 0 | 1 (1.2%) | 1 (0.6%) | 0 | 0 | 0 |
| NEOPLASMS BENIGN, MALIGNANT AND UNSPECIFIED (INCL CYSTS AND POLYPS) | 1 (1.3%) | 0 | 1 (0.6%) | 2 (1.2%) | 2 (1.2%) | 4 (1.2%) |
| HLGT: Breast neoplasms malignant and unspecified (incl nipple) | 0 | 0 | 0 | 1 (0.6%) | 0 | 1 (0.3%) |
| HLT: Breast and nipple neoplasms malignant | 0 | 0 | 0 | 1 (0.6%) | 0 | 1 (0.3%) |
| Breast cancer | 0 | 0 | 0 | 1 (0.6%) | 0 | 1 (0.3%) |
| HLGT: Endocrine neoplasms malignant and unspecified | 1 (1.3%) | 0 | 1 (0.6%) | 0 | 0 | 0 |
| HLT: Thyroid neoplasms malignant | 1 (1.3%) | 0 | 1 (0.6%) | 0 | 0 | 0 |
| Thyroid cancer | 1 (1.3%) | 0 | 1 (0.6%) | 0 | 0 | 0 |
| HLGT: Gastrointestinal neoplasms malignant and unspecified | 0 | 0 | 0 | 0 | 1 (0.6%) | 1 (0.3%) |
| HLT: Pancreatic neoplasms malignant (excl islet cell and carcinoid) | 0 | 0 | 0 | 0 | 1 (0.6%) | 1 (0.3%) |
| Pancreatic carcinoma | 0 | 0 | 0 | 0 | 1 (0.6%) | 1 (0.3%) |
| HLGT: Nervous system neoplasms benign | 0 | 0 | 0 | 0 | 1 (0.6%) | 1 (0.3%) |
| HLT: Meningiomas benign | 0 | 0 | 0 | 0 | 1 (0.6%) | 1 (0.3%) |
| Meningioma benign | 0 | 0 | 0 | 0 | 1 (0.6%) | 1 (0.3%) |
| HLGT: Renal and urinary tract neoplasms malignant and unspecified | 0 | 0 | 0 | 1 (0.6%) | 0 | 1 (0.3%) |
| HLT: Bladder neoplasms malignant | 0 | 0 | 0 | 1 (0.6%) | 0 | 1 (0.3%) |
| Bladder cancer | 0 | 0 | 0 | 1 (0.6%) | 0 | 1 (0.3%) |
| METABOLISM AND NUTRITION DISORDERS | 0 | 0 | 0 | 1 (0.6%) | 1 (0.6%) | 2 (0.6%) |
| HLGT: Glucose metabolism disorders (incl diabetes mellitus) | 0 | 0 | 0 | 1 (0.6%) | 1 (0.6%) | 2 (0.6%) |
| HLT: Hyperglycaemic conditions NEC | 0 | 0 | 0 | 0 | 1 (0.6%) | 1 (0.3%) |
| Hyperglycaemia | 0 | 0 | 0 | 0 | 1 (0.6%) | 1 (0.3%) |
| HLT: Hypoglycaemic conditions NEC | 0 | 0 | 0 | 1 (0.6%) | 0 | 1 (0.3%) |
| Hypoglycaemia | 0 | 0 | 0 | 1 (0.6%) | 0 | 1 (0.3%) |
| PSYCHIATRIC DISORDERS | 0 | 0 | 0 | 1 (0.6%) | 0 | 1 (0.3%) |
| HLGT: Anxiety disorders and symptoms | 0 | 0 | 0 | 1 (0.6%) | 0 | 1 (0.3%) |
| HLT: Anxiety symptoms | 0 | 0 | 0 | 1 (0.6%) | 0 | 1 (0.3%) |
| Anxiety | 0 | 0 | 0 | 1 (0.6%) | 0 | 1 (0.3%) |
| NERVOUS SYSTEM DISORDERS | 0 | 1 (1.2%) | 1 (0.6%) | 2 (1.2%) | 3 (1.9%) | 5 (1.6%) |
| HLGT: Central nervous system vascular disorders | 0 | 1 (1.2%) | 1 (0.6%) | 2 (1.2%) | 1 (0.6%) | 3 (0.9%) |
| HLT: Central nervous system haemorrhages and cerebrovascular accidents | 0 | 1 (1.2%) | 1 (0.6%) | 2 (1.2%) | 1 (0.6%) | 3 (0.9%) |
| Cerebral infarction | 0 | 0 | 0 | 1 (0.6%) | 0 | 1 (0.3%) |
| Cerebrovascular accident | 0 | 0 | 0 | 0 | 1 (0.6%) | 1 (0.3%) |
| Haemorrhagic stroke | 0 | 0 | 0 | 1 (0.6%) | 0 | 1 (0.3%) |
| Ruptured cerebral aneurysm | 0 | 1 (1.2%) | 1 (0.6%) | 0 | 0 | 0 |
| HLGT: Neurological disorders NEC | 0 | 0 | 0 | 0 | 3 (1.9%) | 3 (0.9%) |

TABLE 19-continued

Number (%) of patients experiencing TEAE(s) leading to permanent treatment discontinuation during the overall treatment period by primary SOC, HLGT, HLT, and PT - Safety population

| PRIMARY SYSTEM ORGAN CLASS<br>HLGT: High Level Group<br>Term<br>HLT: High Level Term<br>Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| HLT: Coma states | 0 | 0 | 0 | 0 | 1 (0.6%) | 1 (0.3%) |
| Coma | 0 | 0 | 0 | 0 | 1 (0.6%) | 1 (0.3%) |
| HLT: Neurological signs and symptoms NEC | 0 | 0 | 0 | 0 | 2 (1.2%) | 2 (0.6%) |
| Dizziness | 0 | 0 | 0 | 0 | 2 (1.2%) | 2 (0.6%) |
| CARDIAC DISORDERS | 0 | 2 (2.5%) | 2 (1.3%) | 0 | 1 (0.6%) | 1 (0.3%) |
| HLGT: Cardiac arrhythmias | 0 | 1 (1.2%) | 1 (0.6%) | 0 | 0 | 0 |
| HLT: Rate and rhythm disorders NEC | 0 | 1 (1.2%) | 1 (0.6%) | 0 | 0 | 0 |
| Bradycardia | 0 | 1 (1.2%) | 1 (0.6%) | 0 | 0 | 0 |
| HLGT: Coronary artery disorders | 0 | 1 (1.2%) | 1 (0.6%) | 0 | 1 (0.6%) | 1 (0.3%) |
| HLT: Ischaemic coronary artery disorders | 0 | 1 (1.2%) | 1 (0.6%) | 0 | 1 (0.6%) | 1 (0.3%) |
| Acute myocardial infarction | 0 | 0 | 0 | 0 | 1 (0.6%) | 1 (0.3%) |
| Myocardial infarction | 0 | 1 (1.2%) | 1 (0.6%) | 0 | 0 | 0 |
| VASCULAR DISORDERS | 0 | 0 | 0 | 0 | 1 (0.6%) | 1 (0.3%) |
| HLGT: Vascular hypertensive disorders | 0 | 0 | 0 | 0 | 1 (0.6%) | 1 (0.3%) |
| HLT: Vascular hypertensive disorders NEC | 0 | 0 | 0 | 0 | 1 (0.6%) | 1 (0.3%) |
| Hypertension | 0 | 0 | 0 | 0 | 1 (0.6%) | 1 (0.3%) |
| GASTROINTESTINAL DISORDERS | 1 (1.3%) | 0 | 1 (0.6%) | 9 (5.6%) | 7 (4.3%) | 16 (5.0%) |
| HLGT: Gastrointestinal inflammatory conditions | 0 | 0 | 0 | 0 | 1 (0.6%) | 1 (0.3%) |
| HLT: Gastritis (excl infective) | 0 | 0 | 0 | 0 | 1 (0.6%) | 1 (0.3%) |
| Gastritis | 0 | 0 | 0 | 0 | 1 (0.6%) | 1 (0.3%) |
| HLGT: Gastrointestinal motility and defaecation conditions | 0 | 0 | 0 | 1 (0.6%) | 0 | 1 (0.3%) |
| HLT: Diarrhoea (excl infective) | 0 | 0 | 0 | 1 (0.6%) | 0 | 1 (0.3%) |
| Diarrhoea | 0 | 0 | 0 | 1 (0.6%) | 0 | 1 (0.3%) |
| HLGT: Gastrointestinal signs and symptoms | 1 (1.3%) | 0 | 1 (0.6%) | 8 (5.0%) | 6 (3.7%) | 14 (4.3%) |
| HLT: Flatulence, bloating and distension | 1 (1.3%) | 0 | 1 (0.6%) | 0 | 0 | 0 |
| Abdominal distension | 1 (1.3%) | 0 | 1 (0.6%) | 0 | 0 | 0 |
| HLT: Gastrointestinal and abdominal pains (excl oral and throat) | 0 | 0 | 0 | 1 (0.6%) | 0 | 1 (0.3%) |
| Abdominal pain upper | 0 | 0 | 0 | 1 (0.6%) | 0 | 1 (0.3%) |
| HLT: Nausea and vomiting symptoms | 0 | 0 | 0 | 7 (4.3%) | 6 (3.7%) | 13 (4.0%) |
| Nausea | 0 | 0 | 0 | 6 (3.7%) | 6 (3.7%) | 12 (3.7%) |
| Vomiting | 0 | 0 | 0 | 4 (2.5%) | 1 (0.6%) | 5 (1.6%) |
| HEPATOBILIARY DISORDERS | 0 | 1 (1.2%) | 1 (0.6%) | 0 | 0 | 0 |
| HLGT: Gallbladder disorders | 0 | 1 (1.2%) | 1 (0.6%) | 0 | 0 | 0 |
| HLT: Cholecystitis and cholelithiasis | 0 | 1 (1.2%) | 1 (0.6%) | 0 | 0 | 0 |
| Cholecystitis | 0 | 1 (1.2%) | 1 (0.6%) | 0 | 0 | 0 |
| SKIN AND SUBCUTANEOUS TISSUE DISORDERS | 0 | 0 | 0 | 2 (1.2%) | 1 (0.6%) | 3 (0.9%) |
| HLGT: Epidermal and dermal conditions | 0 | 0 | 0 | 2 (1.2%) | 1 (0.6%) | 3 (0.9%) |
| HLT: Dermatitis and eczema | 0 | 0 | 0 | 1 (0.6%) | 1 (0.6%) | 2 (0.6%) |
| Dermatitis allergic | 0 | 0 | 0 | 1 (0.6%) | 1 (0.6%) | 2 (0.6%) |
| HLT: Psoriatic conditions | 0 | 0 | 0 | 1 (0.6%) | 0 | 1 (0.3%) |
| Dermatitis psoriasiform | 0 | 0 | 0 | 1 (0.6%) | 0 | 1 (0.3%) |
| MUSCULOSKELETAL AND CONNECTIVE TISSUE DISORDERS | 1 (1.3%) | 1 (1.2%) | 2 (1.3%) | 2 (1.2%) | 0 | 2 (0.6%) |
| HLGT: Connective tissue disorders (excl congenital) | 0 | 0 | 0 | 1 (0.6%) | 0 | 1 (0.3%) |
| HLT: Connective tissue disorders (excl LE) | 0 | 0 | 0 | 1 (0.6%) | 0 | 1 (0.3%) |
| Polymyalgia rheumatica | 0 | 0 | 0 | 1 (0.6%) | 0 | 1 (0.3%) |

TABLE 19-continued

Number (%) of patients experiencing TEAE(s) leading to permanent treatment discontinuation during the overall treatment period by primary SOC, HLGT, HLT, and PT - Safety population PRIMARY SYSTEM ORGAN CLASS
HLGT: High Level Group

| Term<br>HLT: High Level Term<br>Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| HLGT: Joint disorders | 1 (1.3%) | 0 | 1 (0.6%) | 1 (0.6%) | 0 | 1 (0.3%) |
| HLT: Osteoarthropathies | 1 (1.3%) | 0 | 1 (0.6%) | 1 (0.6%) | 0 | 1 (0.3%) |
| Osteoarthritis | 1 (1.3%) | 0 | 1 (0.6%) | 1 (0.6%) | 0 | 1 (0.3%) |
| HLGT: Muscle disorders | 0 | 1 (1.2%) | 1 (0.6%) | 0 | 0 | 0 |
| HLT: Muscle pains | 0 | 1 (1.2%) | 1 (0.6%) | 0 | 0 | 0 |
| Myalgia | 0 | 1 (1.2%) | 1 (0.6%) | 0 | 0 | 0 |
| RENAL AND URINARY DISORDERS | 0 | 0 | 0 | 0 | 1 (0.6%) | 1 (0.3%) |
| HLGT: Urinary tract signs and symptoms | 0 | 0 | 0 | 0 | 1 (0.6%) | 1 (0.3%) |
| HLT: Bladder and urethral symptoms | 0 | 0 | 0 | 0 | 1 (0.6%) | 1 (0.3%) |
| Dysuria | 0 | 0 | 0 | 0 | 1 (0.6%) | 1 (0.3%) |
| INVESTIGATIONS | 0 | 0 | 0 | 0 | 1 (0.6%) | 1 (0.3%) |
| HLGT: Gastrointestinal investigations | 0 | 0 | 0 | 0 | 1 (0.6%) | 1 (0.3%) |
| HLT: Digestive enzymes | 0 | 0 | 0 | 0 | 1 (0.6%) | 1 (0.3%) |
| Lipase increased | 0 | 0 | 0 | 0 | 1 (0.6%) | 1 (0.3%) |

TEAE: Treatment Emergent Adverse Event,
SOC: System Organ Class,
HLGT: High Level Group Term,
HLT: High Level Term,
PT: Preferred Term.
MedDRA version: 13.1
n (%) = number and percentage of patients with at least one TEAE leading to permanent treatment discontinuation.
Note:
On-treatment period for the whole study = the time from the first dose of double-blind study medication up to 3 days after the last dose administration.
Table sorted by SOC internationally agreed order and HLGT, HLT, PT alphabetic order.

Twelve (7.5%) patients in the lixisenatide two-step titration group and 6 (3.7%) patients in the lixisenatide one-step titration group had symptomatic hypoglycemia events per protocol definition during the on-treatment period for the whole study, compared with 12 (7.5%) placebo-treated patients who had symptomatic hypoglycemia events during the same period (Table 20). None of the symptomatic hypoglycemia events was severe in intensity. One additional patient (in the placebo two-step titration group) reported a symptomatic hypoglycemia event on a specific AE page for "symptomatic hypoglycemia" but this event did not meet the protocol-specified definition (i.e., the associated glucose values ≥60 mg/dl).

Nine (5.6%) patients in each lixisenatide group and 3 (1.9%) in the combined placebo group experienced injection site reaction AEs (Table 21). The injection site reaction AEs were identified by searching the term "injection site" in either the PTs coded from the investigator reported terms or PTs from the ARAC diagnosis during the allergic reaction adjudication. None of the reactions was serious o rsevere in intensity.

A total of 30 events were reported as possible allergic events by investigators during the on-treatment period for the whole study and were sent to ARAC for adjudication. Of these, 16 events from 15 patients (6 [3.7%] lixisenatide-treated two-step titration patients, 3 [1.9%] lixisenatide-treated one-step titration patients, and 6 [3.8%] placebo-treated patients) were adjudicated as allergic reactions by the ARAC, but only 2 events of anaphylactic reaction (1 in each lixisenatide group) were adjudicated as possibly related to IP (Table 22).

Patient #276303004 (lixisenatide one-step titration), without personal or family history of allergy, developed skin reaction 30 min. after the first dose of the randomized treatment. The event was reported as "allergic exanthema" and coded to PT "dermatitis allergic". The IP was permanently discontinued. Corrective treatment with antihistamines and steroids was applied and the event resolved on the same day. The event was adjudicated by ARAC as an anaphylactic reaction possibly related to the IP Patient #642307010 (lixisenatide two-step titration), without personal or family history of allergy, developed 5.5 months after initiation of IP nausea and dizziness few seconds after IP administration followed by skin reaction. The event was accompanied by hypotension. The event was reported as "allergic dermatitis" and coded to PT "dermatitis allergic". The IP was permanently discontinued following the event. Corrective treatment with antihistamines and steroids was applied and the event resolved the day after. The event was adjudicated by ARAC as an anaphylactic reaction possibly related to the IP Per protocol, any confirmed increase in amylase and/or lipase above twice the upper limit of normal range (ULN) was to be monitored and documented on a specific form: "adverse event form for suspected pancreatitis". During the on-treatment period for the whole study, this form was completed for 4 (2.5%) patients in each lixisenatide group and for 5 (3.1%) patients in the combined placebo group (Table 23). No case of pancreatitis was observed in the study.

Patients who had at least one value of lipase or amylase ≥3 ULN during the on-treatment period are summarized in Table 24. A total of 17 patients (8 [5.0%] in the lixisenatide two-step titration group, 5 [3.1%] in the lixisenatide one-step titration group, and 4 [2.5%] in the combined placebo) with elevated lipase (≥3ULN) were observed. One (0.6%) patient in the lixisenatide one-step titration group had elevated amylase ≥3ULN and none in the lixisenatide two-step titration group and in the combined placebo group.

Per protocol, any calcitonin value confirmed as being ≥20 pg/mL, was to be monitored and reported on a specific adverse event form for "increased calcitonin ≥20 pg/mL". During the on-treatment period for the whole study, this form was completed for 1 (0.6%) patient in each lixisenatide group and for 1 (0.6%) patient in the combined placebo group (Table 25). For 2 of these 3 patients (1 in each lixisenatide group), the calcitonin value was ≥20 ng/L but <50 ng/L and the PT was "blood calcitonin increased". For both patients, further work-up as recommended by the protocol comprising thyroid ultrasound scan and specialist evaluation was conducted and the result was normal. For the third patient (in the placebo two-step titration group), the calcitonin value was ≥50 ng/L and the PT was "thyroid cancer". This patient was diagnosed with medullary thyroid cancer left with lymphogen metastases, which was assessed as not related to the IP by the investigator.

Two (1.4%) patients in the lixisenatide two-step titration group, 2 (1.3%) in the lixisenatide one-step titration group, and 4 (2.5%) in the combined placebo group had at least one value of calcitonin ≥20 ng/L during the on-treatment period (Table 26). Of these patients, in addition to those described in the previous paragraph, two other patients (1 in the lixisenatide one-step titration group and 1 in the combined placebo group) had an adverse event after the discontinuation of IP reported on the specific adverse event form for "increased calcitonin ≥20 pg/mL". For the lixisenatide-treated patient, "high level of calcitonin" was reported 5.5 months after the discontinuation of IP and thyroid nodules were revealed by thyroid ultrasound scan performed 2.5 months after. For the placebo-treated patient, "intermittent increased calcitonin" was reported 7 months after the discontinuation of IP. Thyroid ultrasound scan and specialist evaluation were performed one month later and the results were normal. It should be pointed out that calcitonin measurements were implemented in a protocol amendment after most patients were already randomized in this study. Therefore, baseline calcitonin values are missing for most patients.

TABLE 20

Summary of symptomatic hypoglycemia during the on-treatment period for the whole study - Safety population

| Type | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Total patient years | 123.7 | 116.8 | 240.4 | 229.9 | 238.5 | 468.4 |
| Any symptomatic hypoglycemia | | | | | | |
| Number of patients with events, n (%)[a] | 7 (8.9%) | 5 (6.2%) | 12 (7.5%) | 12 (7.5%) | 6 (3.7%) | 18 (5.6%) |
| Number of patients with events per 100 patient years[b] | 5.7 | 4.3 | 5.0 | 5.2 | 2.5 | 3.8 |
| Blood glucose <60 mg/dL | | | | | | |
| Number of patients with events, n (%)[a] | 6 (7.6%) | 4 (4.9%) | 10 (6.3%) | 11 (6.8%) | 5 (3.1%) | 16 (5.0%) |
| Number of patients with events per 100 patient years[b] | 4.9 | 3.4 | 4.2 | 4.8 | 2.1 | 3.4 |
| No blood glucose reported | | | | | | |
| Number of patients with events, n (%)[a] | 2 (2.5%) | 1 (1.2%) | 3 (1.9%) | 2 (1.2%) | 1 (0.6%) | 3 (0.9%) |
| Number of patients with events per 100 patient years[b] | 1.6 | 0.9 | 1.2 | 0.9 | 0.4 | 0.6 |

[a]Percents are calculated using the number of safety patients as the denominator.
[b]Calculated as (number of patients with events * 100 divided by total exposure + 3 days in patient years).
Symptomatic hypoglycemia = symptomatic hypoglycemia as defined per protocol.
Note:
On-treatment period for the whole study = the time from the first dose of double-blind study medication up to 3 days after the last dose administration.

TABLE 21

Number (%) of patients experiencing injection site reactions during the on-treatment period for the whole study - Safety population

| | Placebo | | | Lixisenatide | | |
|---|---|---|---|---|---|---|
| Event source Preferred Term n (%) | Two-step Titration (N = 79) | One-step Titration (N = 81) | Combined (N = 160) | Two-step Titration (N = 161) | One-step Titration (N = 161) | Combined (N = 322) |
| Any injection site reactions | 1 (1.3%) | 2 (2.5%) | 3 (1.9%) | 9 (5.6%) | 9 (5.6%) | 18 (5.6%) |
| PTs by investigator reported terms | 1 (1.3%) | 2 (2.5%) | 3 (1.9%) | 9 (5.6%) | 8 (5.0%) | 17 (5.3%) |
| Injection site erythema | 0 | 0 | 0 | 4 (2.5%) | 2 (1.2%) | 6 (1.9%) |
| Injection site haematoma | 1 (1.3%) | 0 | 1 (0.6%) | 1 (0.6%) | 1 (0.6%) | 2 (0.6%) |
| Injection site haemorrhage | 0 | 1 (1.2%) | 1 (0.6%) | 0 | 1 (0.6%) | 1 (0.3%) |
| Injection site irritation | 0 | 0 | 0 | 1 (0.6%) | 0 | 1 (0.3%) |
| Injection site macule | 0 | 0 | 0 | 1 (0.6%) | 2 (1.2%) | 3 (0.9%) |
| Injection site pain | 0 | 1 (1.2%) | 1 (0.6%) | 2 (1.2%) | 2 (1.2%) | 4 (1.2%) |
| Injection site pruritus | 0 | 0 | 0 | 3 (1.9%) | 3 (1.9%) | 6 (1.9%) |
| Injection site rash | 0 | 0 | 0 | 0 | 1 (0.6%) | 1 (0.3%) |
| Injection site reaction | 0 | 0 | 0 | 0 | 1 (0.6%) | 1 (0.3%) |
| PTs by ARAC diagnosis | 0 | 0 | 0 | 0 | 1 (0.6%) | 1 (0.3%) |
| Injection site reaction | 0 | 0 | 0 | 0 | 1 (0.6%) | 1 (0.3%) |

ARAC = Allergic Reaction Assessment Committee.
Note:
On-treatment period for the whole study = the time from the first dose of double-blind study medication up to 3 days after the last dose administration.

TABLE 22

Number (%) of patients with events adjudicated as allergic reaction by ARAC during the on-treatment period of the whole study - Safety population

| Relationship to study treatment (by ARAC) | MedDRA coded term (PT) for ARAC diagnosis | ARAC diagnosis | Placebo | | | Lixisenatide | | |
|---|---|---|---|---|---|---|---|---|
| | | | Two-step Titration (N = 79) | One-step Titration (N = 81) | Combined (N = 160) | Two-step Titration (N = 161) | One-step Titration (N = 161) | Combined (N = 322) |
| All | Events adjudicated as an allergic reaction by ARAC | | 1 (1.3%) | 5 (6.2%) | 6 (3.8%) | 6 (3.7%) | 3 (1.9%) | 9 (2.8%) |
| | Anaphylactic reaction | ANAPHYLACTIC REACTION | 0 | 0 | 0 | 1 (0.6%) | 1 (0.6%) | 2 (0.6%) |
| | Angioedema | ANGIOEDEMA | 0 | 0 | 0 | 1 (0.6%) | 1 (0.6%) | 2 (0.6%) |
| | Asthma | ASTHMA | 1 (1.3%) | 0 | 1 (0.6%) | 0 | 0 | 0 |
| | Conjunctivitis allergic | ALLERGIC RHINOCONJUNCTIVITIS | 0 | 1 (1.2%) | 1 (0.6%) | 0 | 1 (0.6%) | 1 (0.3%) |
| | Dermatitis allergic | ALLERGIC DERMATITIS | 0 | 1 (1.2%) | 1 (0.6%) | 0 | 0 | 0 |
| | Pruritus generalised | GENERALIZED PRURITUS | 0 | 0 | 0 | 1 (0.6%) | 0 | 1 (0.3%) |
| | Pruritus | PRURITUS | 0 | 0 | 0 | 1 (0.6%) | 0 | 1 (0.3%) |
| | Rhinitis allergic | ALLERGIC RHINITIS | 0 | 1 (1.2%) | 1 (0.6%) | 1 (0.6%) | 0 | 1 (0.3%) |
| | Urticaria | URTICARIA (HIVES) | 0 | 2 (2.5%) | 2 (1.3%) | 1 (0.6%) | 0 | 1 (0.3%) |
| Possibly Related to IP | Events adjudicated as an allergic reaction by ARAC | | 0 | 0 | 0 | 1 (0.6%) | 1 (0.6%) | 2 (0.6%) |
| | Anaphylactic reaction | ANAPHYLACTIC REACTION | 0 | 0 | 0 | 1 (0.6%) | 1 (0.6%) | 2 (0.6%) |
| Not related to IP | Events adjudicated as an allergic reaction by ARAC | | 1 (1.3%) | 5 (6.2%) | 6 (3.8%) | 5 (3.1%) | 2 (1.2%) | 7 (2.2%) |
| | Angioedema | ANGIOEDEMA | 0 | 0 | 0 | 1 (0.6%) | 1 (0.6%) | 2 (0.6%) |
| | Asthma | ASTHMA | 1 (1.3%) | 0 | 1 (0.6%) | 0 | 0 | 0 |
| | Conjunctivitis allergic | ALLERGIC RHINOCONJUNCTIVITIS | 0 | 1 (1.2%) | 1 (0.6%) | 0 | 1 (0.6%) | 1 (0.3%) |
| | Dermatitis allergic | ALLERGIC DERMATITIS | 0 | 1 (1.2%) | 1 (0.6%) | 0 | 0 | 0 |

TABLE 22-continued

Number (%) of patients with events adjudicated as allergic reaction by ARAC during the on-treatment period of the whole study - Safety population

| Relationship to study treatment (by ARAC) | MedDRA coded term (PT) for ARAC diagnosis | ARAC diagnosis | Placebo | | | Lixisenatide | | |
|---|---|---|---|---|---|---|---|---|
| | | | Two-step Titration (N = 79) | One-step Titration (N = 81) | Combined (N = 160) | Two-step Titration (N = 161) | One-step Titration (N = 161) | Combined (N = 322) |
| | Pruritus generalised | GENERALIZED PRURITUS | 0 | 0 | 0 | 1 (0.6%) | 0 | 1 (0.3%) |
| | Pruritus | PRURITUS | 0 | 0 | 0 | 1 (0.6%) | 0 | 1 (0.3%) |
| | Rhinitis allergic | ALLERGIC RHINITIS | 0 | 1 (1.2%) | 1 (0.6%) | 1 (0.6%) | 0 | 1 (0.3%) |
| | Urticaria | URTICARIA (HIVES) | 0 | 2 (2.5%) | 2 (1.3%) | 1 (0.6%) | 0 | 1 (0.3%) |

ARAC = Allergic Reaction Assessment Committee.
IP = Investigational Product.
Note:
On-treatment period for the whole study = the time from the first dose of double-blind study medication up to 3 days after the last dose administration.

TABLE 23

Number (%) of patients with a specific adverse event form for suspected pancreatitis completed during the on-treatment period for the whole study - Safety population

| Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Any | 2 (2.5%) | 3 (3.7%) | 5 (3.1%) | 4 (2.5%) | 4 (2.5%) | 8 (2.5%) |
| Blood amylase increased | 0 | 0 | 0 | 0 | 1 (0.6%) | 1 (0.3%) |
| Hyperlipasaemia | 2 (2.5%) | 1 (1.2%) | 3 (1.9%) | 2 (1.2%) | 0 | 2 (0.6%) |
| Lipase increased | 0 | 2 (2.5%) | 2 (1.3%) | 1 (0.6%) | 3 (1.9%) | 4 (1.2%) |
| Pancreatic enzymes increased | 0 | 0 | 0 | 1 (0.6%) | 0 | 1 (0.3%) | n (%) = number and percentage of patients with any cases reported on the AE form for suspected pancreatitis.
Note:
On-treatment period for the whole study = the time from the first dose of double-blind study medication up to 3 days after the last dose administration.

TABLE 24

Pancreatic enzymes: Number (%) of patients with at least one post-baseline PCSA during the on-treatment period for the whole study according to baseline PCSA status - Safety population

| Laboratory parameter Baseline By PCSA criteria n/N1 (%) | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Lipase (IU/L) Total* | | | | | | |
| ≥3 ULN | 1/79 (1.3%) | 3/80 (3.8%) | 4/159 (2.5%) | 8/160 (5.0%) | 5/159 (3.1%) | 13/319 (4.1%) |
| Normal/Missing | | | | | | |
| ≥3 ULN | 0/78 | 2/79 (2.5%) | 2/157 (1.3%) | 8/160 (5.0%) | 5/158 (3.2%) | 13/318 (4.1%) |

TABLE 24-continued

Pancreatic enzymes: Number (%) of patients with at least one post-baseline PCSA during the on-treatment period for the whole study according to baseline PCSA status - Safety population

| Laboratory parameter Baseline By PCSA criteria n/N1 (%) | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Amylase (IU/L) Total* | | | | | | |
| ≥3 ULN | 0/79 | 0/80 | 0/159 | 0/160 | 1/159 (0.6%) | 1/319 (0.3%) |
| Normal/Missing | | | | | | |
| ≥3 ULN | 0/79 | 0/80 | 0/159 | 0/160 | 1/159 (0.6%) | 1/319 (0.3%) |

PCSA: Potentially Clinically Significant Abnormalities,
ULN = Upper limit of normal.
*Regardless of baseline.
Note:
On-treatment period for the whole study = the time from the first dose of double-blind study medication up to 3 days after the last dose administration.
The number (n) represents the subset of the total number of patients who met the criterion in question at least once. The denominator (/N1) for each parameter within a treatment group is the number of patients for the treatment group who had that parameter assessed post-baseline by baseline PCSA status. Only the worsening of the worst case for each patient is presented by baseline status.

TABLE 25

Number (%) of patients with increased calcitonin during the on-treatment period for the whole study - Safety population

| Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Any | 1 (1.3%) | 0 | 1 (0.6%) | 1 (0.6%) | 1 (0.6%) | 2 (0.6%) |
| Blood calcitonin increased | 0 | 0 | 0 | 1 (0.6%) | 1 (0.6%) | 2 (0.6%) |
| Thyroid cancer | 1 (1.3%) | 0 | 1 (0.6%) | 0 | 0 | 0 | n (%) = number and percentage of patients with any cases reported on the AE form for increased calcitonin ≥20 ng/L.
Note:
On-treatment period for the whole study = the time from the first dose of double-blind study medication up to 3 days after the last dose administration.

TABLE 26

Serum calcitonin - Number (%) of patients by pre-defined categories during the on-treatment period of the whole study according to baseline category - Safety population

| Laboratory criteria Baseline status Post-baseline | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Calcitonin (ng/L) Total* | | | | | | |
| ≤ULN | 68/77 (88.3%) | 65/78 (83.3%) | 133/155 (85.8%) | 123/142 (86.6%) | 132/150 (88.0%) | 255/292 (87.3%) |
| >ULN-<20 ng/L | 8/77 (10.4%) | 10/78 (12.8%) | 18/155 (11.6%) | 17/142 (12.0%) | 16/150 (10.7%) | 33/292 (11.3%) |
| ≥20 ng/L-<50 ng/L | 0/77 | 3/78 (3.8%) | 3/155 (1.9%) | 2/142 (1.4%) | 2/150 (1.3%) | 4/292 (1.4%) |
| ≥50 ng/L | 1/77 (1.3%) | 0/78 | 1/155 (0.6%) | 0/142 | 0/150 | 0/292 |
| Missing | | | | | | |
| ≤ULN | 61/69 (88.4%) | 59/70 (84.3%) | 120/139 (86.3%) | 114/132 (86.4%) | 119/134 (88.8%) | 233/266 (87.6%) |
| >ULN-<20 ng/L | 7/69 (10.1%) | 9/70 (12.9%) | 16/139 (11.5%) | 16/132 (12.1%) | 14/134 (10.4%) | 30/266 (11.3%) |
| ≥20 ng/L-<50 ng/L | 0/69 | 2/70 (2.9%) | 2/139 (1.4%) | 2/132 (1.5%) | 1/134 (0.7%) | 3/266 (1.1%) |
| ≥50 ng/L | 1/69 (1.4%) | 0/70 | 1/139 (0.7%) | 0/132 | 0/134 | 0/266 |
| ≤ULN | | | | | | |
| ≤ULN | 7/7 (100%) | 6/6 (100%) | 13/13 (100%) | 8/8 (100%) | 13/14 (92.9%) | 21/22 (95.5%) |
| >ULN-<20 ng/L | 0/7 | 0/6 | 0/13 | 0/8 | 1/14 (7.1%) | 1/22 (4.5%) |
| ≥20 ng/L-<50 ng/L | 0/7 | 0/6 | 0/13 | 0/8 | 0/14 | 0/22 |
| ≥50 ng/L | 0/7 | 0/6 | 0/13 | 0/8 | 0/14 | 0/22 |

TABLE 26-continued

Serum calcitonin - Number (%) of patients by pre-defined categories during the on-treatment period of the whole study according to baseline category - Safety population

| Laboratory criteria Baseline status Post-baseline | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| >ULN-<20 ng/L | | | | | | |
| ≤ULN | 0/1 | 0/2 | 0/3 | 1/2 (50.0%) | 0/2 | 1/4 (25.0%) |
| >ULN-<20 ng/L | 1/1 (100%) | 1/2 (50.0%) | 2/3 (66.7%) | 1/2 (50.0%) | 1/2 (50.0%) | 2/4 (50.0%) |
| ≥20 ng/L-<50 ng/L | 0/1 | 1/2 (50.0%) | 1/3 (33.3%) | 0/2 | 1/2 (50.0%) | 1/4 (25.0%) |
| ≥50 ng/L | 0/1 | 0/2 | 0/3 | 0/2 | 0/2 | 0/4 |
| ≥20 ng/L-<50 ng/L | | | | | | |
| ≤ULN | 0/0 | 0/0 | 0/0 | 0/0 | 0/0 | 0/0 |
| >ULN-<20 ng/L | 0/0 | 0/0 | 0/0 | 0/0 | 0/0 | 0/0 |
| ≥20 ng/L-<50 ng/L | 0/0 | 0/0 | 0/0 | 0/0 | 0/0 | 0/0 |
| ≥50 ng/L | 0/0 | 0/0 | 0/0 | 0/0 | 0/0 | 0/0 |
| ≥50 ng/L | | | | | | |
| ≤ULN | 0/0 | 0/0 | 0/0 | 0/0 | 0/0 | 0/0 |
| >ULN-<20 ng/L | 0/0 | 0/0 | 0/0 | 0/0 | 0/0 | 0/0 |
| ≥20 ng/L-<50 ng/L | 0/0 | 0/0 | 0/0 | 0/0 | 0/0 | 0/0 |
| ≥50 ng/L | 0/0 | 0/0 | 0/0 | 0/0 | 0/0 | 0/0 |

ULN = Upper limit of normal.
*Regardless of baseline.
Note:
On-treatment period for the whole study = the time from the first dose of double-blind study medication up to 3 days after the last dose administration.
The numerator represents the number of patients who were in the pre-specified categories at post-baseline in each baseline category. The denominator for each parameter within a treatment group is the number of patients for the treatment group who had that parameter assessed post-baseline by baseline status.
A patient is counted only in the worst category.

TABLE 27

Mean change in HbA1c (%) from baseline by visit - mITT population

| Treatment Time point | Observed data | | | | | | | Change from baseline | | | | | |
|---|---|---|---|---|---|---|---|---|---|---|---|---|---|
| | N | Mean | SD | SE | Median | Min | Max | N | Mean | SD | SE | Median | Min | Max |
| Placebo Combined (N = 159) | | | | | | | | | | | | | | |
| Screening | 159 | 8.15 | 0.84 | 0.067 | 8.00 | 7.0 | 10.0 | | | | | | | |
| Baseline | 159 | 8.03 | 0.82 | 0.065 | 7.90 | 6.2 | 10.3 | | | | | | | |
| Week 8 | 157 | 7.70 | 0.84 | 0.067 | 7.50 | 6.1 | 10.6 | 157 | −0.33 | 0.68 | 0.054 | −0.30 | −2.5 | 1.7 |
| Week 12 | 150 | 7.62 | 0.92 | 0.075 | 7.50 | 5.8 | 11.0 | 150 | −0.42 | 0.81 | 0.066 | −0.30 | −3.1 | 2.7 |
| Week 24 | 147 | 7.57 | 0.84 | 0.070 | 7.50 | 5.9 | 10.7 | 147 | −0.46 | 0.79 | 0.065 | −0.40 | −3.1 | 1.3 |
| Week 24 (LOCF) | 158 | 7.63 | 0.92 | 0.073 | 7.60 | 5.9 | 10.7 | 158 | −0.40 | 0.85 | 0.067 | −0.40 | −3.1 | 2.2 |
| Week 36 | 122 | 7.43 | 0.83 | 0.075 | 7.25 | 6.1 | 10.0 | 122 | −0.54 | 0.85 | 0.077 | −0.50 | −3.4 | 1.0 |
| Week 44 | 114 | 7.38 | 0.84 | 0.079 | 7.20 | 6.0 | 10.2 | 114 | −0.55 | 0.90 | 0.084 | −0.60 | −3.2 | 2.1 |
| Week 52 | 107 | 7.44 | 0.95 | 0.092 | 7.30 | 5.8 | 10.9 | 107 | −0.49 | 0.95 | 0.091 | −0.60 | −3.0 | 3.2 |
| Week 60 | 95 | 7.35 | 1.04 | 0.107 | 7.10 | 5.7 | 11.0 | 95 | −0.64 | 1.02 | 0.105 | −0.60 | −3.2 | 3.8 |
| Week 68 | 86 | 7.24 | 0.91 | 0.098 | 7.00 | 5.3 | 10.9 | 86 | −0.69 | 1.11 | 0.120 | −0.60 | −3.5 | 4.0 |
| Week 76 | 79 | 7.28 | 1.09 | 0.122 | 7.20 | 5.5 | 11.8 | 79 | −0.64 | 1.25 | 0.141 | −0.70 | −3.7 | 4.9 |
| Week 84 | 53 | 7.22 | 0.95 | 0.131 | 7.10 | 5.4 | 10.6 | 53 | −0.76 | 1.24 | 0.170 | −0.70 | −3.8 | 3.4 |
| Week 92 | 20 | 7.22 | 0.59 | 0.133 | 7.10 | 6.4 | 8.3 | 20 | −0.93 | 0.85 | 0.190 | −0.60 | −2.8 | 0.5 |
| Week 100 | 10 | 7.23 | 0.80 | 0.253 | 6.95 | 6.3 | 8.5 | 10 | −0.82 | 0.54 | 0.171 | −0.90 | −1.5 | 0.2 |
| Week 108 | 4 | 7.30 | 0.71 | 0.354 | 7.20 | 6.6 | 8.2 | 4 | −0.43 | 0.22 | 0.111 | −0.40 | −0.7 | −0.2 |
| Last on-treatment value | 158 | 7.83 | 1.09 | 0.087 | 7.80 | 6.0 | 11.2 | 158 | −0.21 | 1.07 | 0.085 | −0.20 | −2.8 | 4.3 |
| Lixisenatide Two-step Titration (N = 160) | | | | | | | | | | | | | | |
| Screening | 160 | 8.20 | 0.87 | 0.069 | 8.05 | 7.0 | 10.0 | | | | | | | |
| Baseline | 160 | 8.10 | 0.88 | 0.070 | 8.00 | 6.3 | 11.4 | | | | | | | |
| Week 8 | 147 | 7.40 | 1.03 | 0.085 | 7.20 | 5.5 | 11.3 | 147 | −0.72 | 0.66 | 0.054 | −0.70 | −2.5 | 1.9 |
| Week 12 | 147 | 7.28 | 1.00 | 0.083 | 7.10 | 5.5 | 11.0 | 147 | −0.85 | 0.83 | 0.068 | −0.80 | −2.7 | 2.6 |
| Week 24 | 138 | 7.22 | 0.98 | 0.084 | 7.10 | 5.5 | 11.5 | 138 | −0.87 | 0.94 | 0.080 | −0.85 | −4.0 | 2.4 |

TABLE 27-continued

Mean change in HbA1c (%) from baseline by visit - mITT population

| Treatment | Observed data | | | | | | | Change from baseline | | | | | | |
|---|---|---|---|---|---|---|---|---|---|---|---|---|---|---|
| Time point | N | Mean | SD | SE | Median | Min | Max | N | Mean | SD | SE | Median | Min | Max |
| Week 24 (LOCF) | 152 | 7.27 | 1.00 | 0.081 | 7.10 | 5.5 | 11.5 | 152 | −0.85 | 0.93 | 0.075 | −0.80 | −4.0 | 2.4 |
| Week 36 | 124 | 7.19 | 0.99 | 0.089 | 7.15 | 5.4 | 11.0 | 124 | −0.89 | 0.94 | 0.084 | −0.80 | −3.2 | 2.3 |
| Week 44 | 121 | 7.29 | 1.14 | 0.104 | 7.20 | 5.3 | 11.8 | 121 | −0.82 | 1.08 | 0.098 | −0.80 | −3.9 | 3.7 |
| Week 52 | 116 | 7.24 | 1.17 | 0.109 | 7.20 | 5.4 | 14.3 | 116 | −0.88 | 1.13 | 0.104 | −0.80 | −3.7 | 6.2 |
| Week 60 | 112 | 7.22 | 1.07 | 0.101 | 7.05 | 5.0 | 11.8 | 112 | −0.86 | 1.05 | 0.099 | −0.80 | −4.1 | 2.0 |
| Week 68 | 106 | 7.21 | 1.00 | 0.097 | 7.10 | 5.4 | 10.8 | 106 | −0.89 | 1.05 | 0.102 | −0.90 | −3.3 | 2.1 |
| Week 76 | 101 | 7.14 | 0.95 | 0.095 | 7.00 | 5.3 | 10.0 | 101 | −0.92 | 0.99 | 0.098 | −0.70 | −3.9 | 0.9 |
| Week 84 | 59 | 7.05 | 0.92 | 0.120 | 7.00 | 5.5 | 10.2 | 59 | −1.00 | 0.97 | 0.127 | −0.80 | −3.4 | 1.0 |
| Week 92 | 30 | 7.28 | 1.09 | 0.200 | 7.25 | 5.8 | 10.8 | 30 | −0.81 | 0.96 | 0.175 | −0.85 | −2.6 | 1.5 |
| Week 100 | 11 | 6.81 | 0.65 | 0.197 | 6.60 | 6.1 | 8.0 | 11 | −1.33 | 0.98 | 0.295 | −1.30 | −3.1 | 0.1 |
| Week 108 | 5 | 6.50 | 0.31 | 0.138 | 6.50 | 6.2 | 7.0 | 5 | −1.60 | 1.17 | 0.523 | −1.50 | −3.3 | 0.0 |
| Last on-treatment value | 152 | 7.47 | 1.10 | 0.089 | 7.40 | 5.5 | 11.6 | 152 | −0.65 | 1.08 | 0.087 | −0.60 | −3.9 | 2.2 |
| Lixisenatide One-step Titration (N = 158) | | | | | | | | | | | | | | |
| Screening | 158 | 8.12 | 0.81 | 0.065 | 8.00 | 7.0 | 9.8 | | | | | | | |
| Baseline | 158 | 7.98 | 0.88 | 0.070 | 7.80 | 6.2 | 10.2 | | | | | | | |
| Week 8 | 154 | 7.22 | 0.78 | 0.063 | 7.10 | 5.7 | 9.7 | 154 | −0.76 | 0.66 | 0.053 | −0.70 | −2.8 | 0.6 |
| Week 12 | 150 | 7.12 | 0.82 | 0.067 | 7.00 | 5.7 | 9.8 | 150 | −0.87 | 0.76 | 0.062 | −0.80 | −3.4 | 0.9 |
| Week 24 | 141 | 7.07 | 0.82 | 0.069 | 7.00 | 5.3 | 9.6 | 141 | −0.88 | 0.87 | 0.073 | −0.90 | −3.8 | 1.3 |
| Week 24 (LOCF) | 156 | 7.13 | 0.85 | 0.068 | 7.00 | 5.3 | 9.6 | 156 | −0.86 | 0.86 | 0.069 | −0.80 | −3.8 | 1.3 |
| Week 36 | 130 | 7.06 | 0.80 | 0.070 | 7.00 | 5.5 | 10.9 | 130 | −0.82 | 0.85 | 0.075 | −0.80 | −3.2 | 2.0 |
| Week 44 | 128 | 7.11 | 0.80 | 0.070 | 7.05 | 5.4 | 10.9 | 128 | −0.77 | 0.90 | 0.079 | −0.70 | −3.6 | 2.7 |
| Week 52 | 119 | 7.02 | 0.68 | 0.063 | 7.00 | 5.5 | 9.0 | 119 | −0.86 | 0.86 | 0.079 | −0.80 | −3.8 | 1.9 |
| Week 60 | 110 | 7.02 | 0.73 | 0.070 | 7.00 | 5.5 | 9.4 | 110 | −0.87 | 0.84 | 0.081 | −0.80 | −3.8 | 1.6 |
| Week 68 | 106 | 6.98 | 0.72 | 0.070 | 6.90 | 5.7 | 9.6 | 106 | −0.86 | 0.85 | 0.082 | −0.85 | −3.6 | 1.0 |
| Week 76 | 99 | 6.99 | 0.77 | 0.078 | 6.90 | 5.4 | 9.2 | 99 | −0.85 | 0.90 | 0.090 | −0.80 | −3.6 | 1.0 |
| Week 84 | 65 | 6.93 | 0.72 | 0.090 | 6.80 | 5.5 | 9.3 | 65 | −0.90 | 0.96 | 0.120 | −0.70 | −3.7 | 1.3 |
| Week 92 | 33 | 6.97 | 0.66 | 0.115 | 6.90 | 5.7 | 8.4 | 33 | −1.05 | 0.92 | 0.159 | −1.00 | −3.1 | 0.5 |
| Week 100 | 11 | 7.35 | 0.61 | 0.183 | 7.40 | 6.6 | 8.2 | 11 | −0.85 | 0.92 | 0.277 | −0.70 | −2.2 | 0.8 |
| Week 108 | 4 | 7.60 | 1.02 | 0.508 | 7.30 | 6.8 | 9.0 | 4 | −0.17 | 1.61 | 0.807 | −0.10 | −2.2 | 1.7 |
| Last on-treatment value | 156 | 7.44 | 1.02 | 0.082 | 7.40 | 5.4 | 10.8 | 156 | −0.55 | 1.06 | 0.085 | −0.60 | −3.6 | 4.4 |

LOCF = Last observation carried forward.
Note:
The analysis excluded measurements obtained after the introduction of rescue medication and/or after the treatment cessation plus 3 days.
For Week 24 (LOCF), the analysis included measurements obtained up to 3 days after the last dose of the double-blind investigational product injection on or before Visit 12 (Week 24), or Day 169 if Visit 12 (Week 24) is not available.

TABLE 28

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term HLT: High Level Term Preferred Term | Two-step Titration (N = 79) | One-step Titration (N = 81) | Combined (N = 160) | Two-step Titration (N = 161) | One-step Titration (N = 161) | Combined (N = 322) |
| Any class | 69 (87.3%) | 69 (85.2%) | 138 (86.3%) | 141 (87.6%) | 138 (85.7%) | 279 (86.6%) |
| INFECTIONS AND INFESTATIONS | 40 (50.6%) | 42 (51.9%) | 82 (51.3%) | 71 (44.1%) | 67 (41.6%) | 138 (42.9%) |
| HLGT: Fungal infectious disorders | 2 (2.5%) | 2 (2.5%) | 4 (2.5%) | 3 (1.9%) | 4 (2.5%) | 7 (2.2%) |
| HLT: Fungal infections NEC | 1 (1.3%) | 1 (1.2%) | 2 (1.3%) | 2 (1.2%) | 4 (2.5%) | 6 (1.9%) |
| Onychomycosis | 1 (1.3%) | 1 (1.2%) | 2 (1.3%) | 2 (1.2%) | 1 (0.6%) | 3 (0.9%) |
| HLGT: Infections - pathogen unspecified | 35 (44.3%) | 33 (40.7%) | 68 (42.5%) | 58 (36.0%) | 57 (35.4%) | 115 (35.7%) |
| HLT: Abdominal and gastrointestinal infections | 7 (8.9%) | 3 (3.7%) | 10 (6.3%) | 4 (2.5%) | 9 (5.6%) | 13 (4.0%) |
| Gastroenteritis | 7 (8.9%) | 2 (2.5%) | 9 (5.6%) | 4 (2.5%) | 7 (4.3%) | 11 (3.4%) |
| HLT: Dental and oral soft tissue infections | 2 (2.5%) | 3 (3.7%) | 5 (3.1%) | 2 (1.2%) | 4 (2.5%) | 6 (1.9%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS<br>HLGT: High Level Group Term<br>HLT: High Level Term<br>Preferred Term | Placebo | | | Lixisenatide | | |
|---|---|---|---|---|---|---|
| | Two-step Titration (N = 79) | One-step Titration (N = 81) | Combined (N = 160) | Two-step Titration (N = 161) | One-step Titration (N = 161) | Combined (N = 322) |
| Tooth infection | 2 (2.5%) | 2 (2.5%) | 4 (2.5%) | 1 (0.6%) | 3 (1.9%) | 4 (1.2%) |
| HLT: Female reproductive tract infections | 0 | 3 (3.7%) | 3 (1.9%) | 0 | 4 (2.5%) | 4 (1.2%) |
| Cervicitis | 0 | 1 (1.2%) | 1 (0.6%) | 0 | 2 (1.2%) | 2 (0.6%) |
| Vaginal infection | 0 | 1 (1.2%) | 1 (0.6%) | 0 | 2 (1.2%) | 2 (0.6%) |
| HLT: Lower respiratory tract and lung infections | 9 (11.4%) | 8 (9.9%) | 17 (10.6%) | 5 (3.1%) | 9 (5.6%) | 14 (4.3%) |
| Bronchitis | 6 (7.6%) | 7 (8.6%) | 13 (8.1%) | 3 (1.9%) | 7 (4.3%) | 10 (3.1%) |
| Pneumonia | 3 (3.8%) | 1 (1.2%) | 4 (2.5%) | 1 (0.6%) | 2 (1.2%) | 3 (0.9%) |
| HLT: Skin structures and soft tissue infections | 0 | 2 (2.5%) | 2 (1.3%) | 3 (1.9%) | 2 (1.2%) | 5 (1.6%) |
| Paronychia | 0 | 0 | 0 | 2 (1.2%) | 0 | 2 (0.6%) |
| HLT: Upper respiratory tract infections | 26 (32.9%) | 24 (29.6%) | 50 (31.3%) | 41 (25.5%) | 36 (22.4%) | 77 (23.9%) |
| Acute tonsillitis | 0 | 1 (1.2%) | 1 (0.6%) | 2 (1.2%) | 0 | 2 (0.6%) |
| Laryngitis | 0 | 0 | 0 | 2 (1.2%) | 0 | 2 (0.6%) |
| Nasopharyngitis | 13 (16.5%) | 8 (9.9%) | 21 (13.1%) | 16 (9.9%) | 18 (11.2%) | 34 (10.6%) |
| Pharyngitis | 6 (7.6%) | 6 (7.4%) | 12 (7.5%) | 9 (5.6%) | 10 (6.2%) | 19 (5.9%) |
| Pharyngotonsillitis | 1 (1.3%) | 1 (1.2%) | 2 (1.3%) | 1 (0.6%) | 0 | 1 (0.3%) |
| Rhinitis | 1 (1.3%) | 3 (3.7%) | 4 (2.5%) | 2 (1.2%) | 1 (0.6%) | 3 (0.9%) |
| Sinusitis | 1 (1.3%) | 0 | 1 (0.6%) | 3 (1.9%) | 1 (0.6%) | 4 (1.2%) |
| Tonsillitis | 3 (3.8%) | 1 (1.2%) | 4 (2.5%) | 5 (3.1%) | 5 (3.1%) | 10 (3.1%) |
| Tracheobronchitis | 1 (1.3%) | 2 (2.5%) | 3 (1.9%) | 0 | 0 | 0 |
| Upper respiratory tract infection | 4 (5.1%) | 5 (6.2%) | 9 (5.6%) | 4 (2.5%) | 6 (3.7%) | 10 (3.1%) |
| HLT: Urinary tract infections | 7 (8.9%) | 7 (8.6%) | 14 (8.8%) | 12 (7.5%) | 14 (8.7%) | 26 (8.1%) |
| Cystitis | 2 (2.5%) | 2 (2.5%) | 4 (2.5%) | 1 (0.6%) | 6 (3.7%) | 7 (2.2%) |
| Urinary tract infection | 6 (7.6%) | 5 (6.2%) | 11 (6.9%) | 11 (6.8%) | 10 (6.2%) | 21 (6.5%) |
| HLGT: Viral infectious disorders | 10 (12.7%) | 15 (18.5%) | 25 (15.6%) | 26 (16.1%) | 25 (15.5%) | 51 (15.8%) |
| HLT: Flaviviral infections | 1 (1.3%) | 0 | 1 (0.6%) | 0 | 5 (3.1%) | 5 (1.6%) |
| Dengue fever | 1 (1.3%) | 0 | 1 (0.6%) | 0 | 5 (3.1%) | 5 (1.6%) |
| HLT: Herpes viral infections | 0 | 1 (1.2%) | 1 (0.6%) | 3 (1.9%) | 6 (3.7%) | 9 (2.8%) |
| Herpes zoster | 0 | 0 | 0 | 1 (0.6%) | 3 (1.9%) | 4 (1.2%) |
| Oral herpes | 0 | 1 (1.2%) | 1 (0.6%) | 2 (1.2%) | 3 (1.9%) | 5 (1.6%) |
| HLT: Influenza viral infections | 9 (11.4%) | 9 (11.1%) | 18 (11.3%) | 20 (12.4%) | 12 (7.5%) | 32 (9.9%) |
| Influenza | 9 (11.4%) | 9 (11.1%) | 18 (11.3%) | 20 (12.4%) | 11 (6.8%) | 31 (9.6%) |
| HLT: Viral infections NEC | 1 (1.3%) | 5 (6.2%) | 6 (3.8%) | 6 (3.7%) | 6 (3.7%) | 12 (3.7%) |
| Respiratory tract infection viral | 0 | 2 (2.5%) | 2 (1.3%) | 3 (1.9%) | 0 | 3 (0.9%) |
| Viral infection | 0 | 1 (1.2%) | 1 (0.6%) | 2 (1.2%) | 2 (1.2%) | 4 (1.2%) |
| Viral upper respiratory tract infection | 1 (1.3%) | 2 (2.5%) | 3 (1.9%) | 1 (0.6%) | 4 (2.5%) | 5 (1.6%) |
| NEOPLASMS BENIGN, MALIGNANT AND UNSPECIFIED (INCL CYSTS AND POLYPS) | 4 (5.1%) | 0 | 4 (2.5%) | 7 (4.3%) | 6 (3.7%) | 13 (4.0%) |
| HLGT: Endocrine neoplasms malignant and unspecified | 1 (1.3%) | 0 | 1 (0.6%) | 2 (1.2%) | 1 (0.6%) | 3 (0.9%) |
| HLT: Endocrine neoplasms malignant and unspecified NEC | 0 | 0 | 0 | 2 (1.2%) | 1 (0.6%) | 3 (0.9%) |
| Thyroid neoplasm | 0 | 0 | 0 | 2 (1.2%) | 1 (0.6%) | 3 (0.9%) |
| BLOOD AND LYMPHATIC SYSTEM DISORDERS | 4 (5.1%) | 3 (3.7%) | 7 (4.4%) | 7 (4.3%) | 6 (3.7%) | 13 (4.0%) |
| HLGT: Anaemias nonhaemolytic and marrow depression | 3 (3.8%) | 2 (2.5%) | 5 (3.1%) | 5 (3.1%) | 4 (2.5%) | 9 (2.8%) |
| HLT: Anaemias NEC | 3 (3.8%) | 2 (2.5%) | 5 (3.1%) | 5 (3.1%) | 4 (2.5%) | 9 (2.8%) |
| Anaemia | 3 (3.8%) | 2 (2.5%) | 5 (3.1%) | 5 (3.1%) | 3 (1.9%) | 8 (2.5%) |
| HLGT: White blood cell disorders | 1 (1.3%) | 1 (1.2%) | 2 (1.3%) | 2 (1.2%) | 2 (1.2%) | 4 (1.2%) |
| HLT: Leukocytoses NEC | 1 (1.3%) | 1 (1.2%) | 2 (1.3%) | 0 | 2 (1.2%) | 2 (0.6%) |
| Leukocytosis | 0 | 1 (1.2%) | 1 (0.6%) | 0 | 2 (1.2%) | 2 (0.6%) |
| IMMUNE SYSTEM DISORDERS | 0 | 0 | 0 | 3 (1.9%) | 0 | 3 (0.9%) |
| HLGT: Allergic conditions | 0 | 0 | 0 | 3 (1.9%) | 0 | 3 (0.9%) |
| HLT: Allergies to foods, food additives, drugs and other chemicals | 0 | 0 | 0 | 3 (1.9%) | 0 | 3 (0.9%) |
| Drug hypersensitivity | 0 | 0 | 0 | 2 (1.2%) | 0 | 2 (0.6%) |
| ENDOCRINE DISORDERS | 2 (2.5%) | 3 (3.7%) | 5 (3.1%) | 1 (0.6%) | 2 (1.2%) | 3 (0.9%) |
| HLGT: Thyroid gland disorders | 2 (2.5%) | 2 (2.5%) | 4 (2.5%) | 1 (0.6%) | 2 (1.2%) | 3 (0.9%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term HLT: High Level Term Preferred Term | Two-step Titration (N = 79) | One-step Titration (N = 81) | Combined (N = 160) | Two-step Titration (N = 161) | One-step Titration (N = 161) | Combined (N = 322) |
| HLT: Acute and chronic thyroiditis | 0 | 1 (1.2%) | 1 (0.6%) | 0 | 2 (1.2%) | 2 (0.6%) |
| Autoimmune thyroiditis | 0 | 0 | 0 | 0 | 2 (1.2%) | 2 (0.6%) |
| HLT: Thyroid disorders NEC | 1 (1.3%) | 1 (1.2%) | 2 (1.3%) | 1 (0.6%) | 0 | 1 (0.3%) |
| Goitre | 1 (1.3%) | 1 (1.2%) | 2 (1.3%) | 1 (0.6%) | 0 | 1 (0.3%) |
| HLT: Thyroid hypofunction disorders | 1 (1.3%) | 1 (1.2%) | 2 (1.3%) | 0 | 1 (0.6%) | 1 (0.3%) |
| Hypothyroidism | 1 (1.3%) | 1 (1.2%) | 2 (1.3%) | 0 | 1 (0.6%) | 1 (0.3%) |
| METABOLISM AND NUTRITION DISORDERS | 19 (24.1%) | 18 (22.2%) | 37 (23.1%) | 26 (16.1%) | 28 (17.4%) | 54 (16.8%) |
| HLGT: Appetite and general nutritional disorders | 5 (6.3%) | 4 (4.9%) | 9 (5.6%) | 9 (5.6%) | 10 (6.2%) | 19 (5.9%) |
| HLT: Appetite disorders | 5 (6.3%) | 4 (4.9%) | 9 (5.6%) | 9 (5.6%) | 10 (6.2%) | 19 (5.9%) |
| Decreased appetite | 3 (3.8%) | 4 (4.9%) | 7 (4.4%) | 8 (5.0%) | 8 (5.0%) | 16 (5.0%) |
| Increased appetite | 2 (2.5%) | 0 | 2 (1.3%) | 1 (0.6%) | 2 (1.2%) | 3 (0.9%) |
| HLGT: Glucose metabolism disorders (incl diabetes mellitus) | 8 (10.1%) | 5 (6.2%) | 13 (8.1%) | 16 (9.9%) | 8 (5.0%) | 24 (7.5%) |
| HLT: Diabetes mellitus (incl subtypes) | 0 | 0 | 0 | 2 (1.2%) | 0 | 2 (0.6%) |
| Diabetes mellitus | 0 | 0 | 0 | 2 (1.2%) | 0 | 2 (0.6%) |
| HLT: Hyperglycaemic conditions NEC | 0 | 0 | 0 | 2 (1.2%) | 2 (1.2%) | 4 (1.2%) |
| Hyperglycaemia | 0 | 0 | 0 | 2 (1.2%) | 2 (1.2%) | 4 (1.2%) |
| HLT: Hypoglycaemic conditions NEC | 8 (10.1%) | 5 (6.2%) | 13 (8.1%) | 12 (7.5%) | 6 (3.7%) | 18 (5.6%) |
| Hypoglycaemia | 8 (10.1%) | 5 (6.2%) | 13 (8.1%) | 12 (7.5%) | 6 (3.7%) | 18 (5.6%) |
| HLGT: Lipid metabolism disorders | 2 (2.5%) | 9 (11.1%) | 11 (6.9%) | 1 (0.6%) | 5 (3.1%) | 6 (1.9%) |
| HLT: Elevated triglycerides | 1 (1.3%) | 4 (4.9%) | 5 (3.1%) | 0 | 3 (1.9%) | 3 (0.9%) |
| Hypertriglyceridaemia | 1 (1.3%) | 4 (4.9%) | 5 (3.1%) | 0 | 3 (1.9%) | 3 (0.9%) |
| HLT: Lipid metabolism and deposit disorders NEC | 1 (1.3%) | 4 (4.9%) | 5 (3.1%) | 0 | 1 (0.6%) | 1 (0.3%) |
| Dyslipidaemia | 1 (1.3%) | 3 (3.7%) | 4 (2.5%) | 0 | 1 (0.6%) | 1 (0.3%) |
| HLGT: Metabolism disorders NEC | 2 (2.5%) | 1 (1.2%) | 3 (1.9%) | 2 (1.2%) | 0 | 2 (0.6%) |
| HLT: Metabolic disorders NEC | 2 (2.5%) | 1 (1.2%) | 3 (1.9%) | 2 (1.2%) | 0 | 2 (0.6%) |
| Hyperlipasaemia | 2 (2.5%) | 1 (1.2%) | 3 (1.9%) | 2 (1.2%) | 0 | 2 (0.6%) |
| HLGT: Purine and pyrimidine metabolism disorders | 4 (5.1%) | 0 | 4 (2.5%) | 1 (0.6%) | 5 (3.1%) | 6 (1.9%) |
| HLT: Purine metabolism disorders NEC | 4 (5.1%) | 0 | 4 (2.5%) | 1 (0.6%) | 5 (3.1%) | 6 (1.9%) |
| Gout | 0 | 0 | 0 | 0 | 2 (1.2%) | 2 (0.6%) |
| Hyperuricaemia | 4 (5.1%) | 0 | 4 (2.5%) | 1 (0.6%) | 4 (2.5%) | 5 (1.6%) |
| PSYCHIATRIC DISORDERS | 11 (13.9%) | 3 (3.7%) | 14 (8.8%) | 14 (8.7%) | 19 (11.8%) | 33 (10.2%) |
| HLGT: Anxiety disorders and symptoms | 7 (8.9%) | 1 (1.2%) | 8 (5.0%) | 4 (2.5%) | 4 (2.5%) | 8 (2.5%) |
| HLT: Anxiety symptoms | 6 (7.6%) | 0 | 6 (3.8%) | 3 (1.9%) | 2 (1.2%) | 5 (1.6%) |
| Anxiety | 1 (1.3%) | 0 | 1 (0.6%) | 3 (1.9%) | 1 (0.6%) | 4 (1.2%) |
| Stress | 3 (3.8%) | 0 | 3 (1.9%) | 0 | 0 | 0 |
| HLGT: Depressed mood disorders and disturbances | 3 (3.8%) | 0 | 3 (1.9%) | 6 (3.7%) | 4 (2.5%) | 10 (3.1%) |
| HLT: Depressive disorders | 2 (2.5%) | 0 | 2 (1.3%) | 5 (3.1%) | 2 (1.2%) | 7 (2.2%) |
| Depression | 2 (2.5%) | 0 | 2 (1.3%) | 5 (3.1%) | 2 (1.2%) | 7 (2.2%) |
| HLT: Mood alterations with depressive symptoms | 1 (1.3%) | 0 | 1 (0.6%) | 2 (1.2%) | 2 (1.2%) | 4 (1.2%) |
| Depressed mood | 1 (1.3%) | 0 | 1 (0.6%) | 2 (1.2%) | 2 (1.2%) | 4 (1.2%) |
| HLGT: Eating disorders and disturbances | 0 | 0 | 0 | 2 (1.2%) | 2 (1.2%) | 4 (1.2%) |
| HLT: Eating disorders NEC | 0 | 0 | 0 | 2 (1.2%) | 2 (1.2%) | 4 (1.2%) |
| Food aversion | 0 | 0 | 0 | 2 (1.2%) | 2 (1.2%) | 4 (1.2%) |
| HLGT: Sleep disorders and disturbances | 2 (2.5%) | 1 (1.2%) | 3 (1.9%) | 3 (1.9%) | 8 (5.0%) | 11 (3.4%) |
| HLT: Disturbances in initiating and maintaining sleep | 2 (2.5%) | 1 (1.2%) | 3 (1.9%) | 3 (1.9%) | 6 (3.7%) | 9 (2.8%) |
| Insomnia | 2 (2.5%) | 1 (1.2%) | 3 (1.9%) | 3 (1.9%) | 6 (3.7%) | 9 (2.8%) |
| NERVOUS SYSTEM DISORDERS | 23 (29.1%) | 26 (32.1%) | 49 (30.6%) | 52 (32.3%) | 46 (28.6%) | 98 (30.4%) |
| HLGT: Central nervous system vascular disorders | 0 | 3 (3.7%) | 3 (1.9%) | 5 (3.1%) | 3 (1.9%) | 8 (2.5%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term HLT: High Level Term Preferred Term | Two-step Titration (N = 79) | One-step Titration (N = 81) | Combined (N = 160) | Two-step Titration (N = 161) | One-step Titration (N = 161) | Combined (N = 322) |
| HLT: Central nervous system haemorrhages and cerebrovascular accidents | 0 | 3 (3.7%) | 3 (1.9%) | 3 (1.9%) | 3 (1.9%) | 6 (1.9%) |
| Cerebral infarction | 0 | 0 | 0 | 2 (1.2%) | 0 | 2 (0.6%) |
| Cerebral ischaemia | 0 | 0 | 0 | 0 | 2 (1.2%) | 2 (0.6%) |
| HLGT: Headaches | 11 (13.9%) | 10 (12.3%) | 21 (13.1%) | 24 (14.9%) | 20 (12.4%) | 44 (13.7%) |
| HLT: Headaches NEC | 11 (13.9%) | 9 (11.1%) | 20 (12.5%) | 24 (14.9%) | 20 (12.4%) | 44 (13.7%) |
| Headache | 11 (13.9%) | 9 (11.1%) | 20 (12.5%) | 23 (14.3%) | 20 (12.4%) | 43 (13.4%) |
| HLGT: Movement disorders (incl parkinsonism) | 1 (1.3%) | 2 (2.5%) | 3 (1.9%) | 3 (1.9%) | 1 (0.6%) | 4 (1.2%) |
| HLT: Tremor (excl congenital) | 1 (1.3%) | 2 (2.5%) | 3 (1.9%) | 3 (1.9%) | 1 (0.6%) | 4 (1.2%) |
| Tremor | 1 (1.3%) | 2 (2.5%) | 3 (1.9%) | 3 (1.9%) | 1 (0.6%) | 4 (1.2%) |
| HLGT: Neurological disorders NEC | 11 (13.9%) | 13 (16.0%) | 24 (15.0%) | 26 (16.1%) | 19 (11.8%) | 45 (14.0%) |
| HLT: Disturbances in consciousness NEC | 1 (1.3%) | 1 (1.2%) | 2 (1.3%) | 6 (3.7%) | 3 (1.9%) | 9 (2.8%) |
| Lethargy | 0 | 0 | 0 | 0 | 2 (1.2%) | 2 (0.6%) |
| Somnolence | 0 | 1 (1.2%) | 1 (0.6%) | 4 (2.5%) | 2 (1.2%) | 6 (1.9%) |
| Syncope | 1 (1.3%) | 1 (1.2%) | 2 (1.3%) | 2 (1.2%) | 0 | 2 (0.6%) |
| HLT: Neurological signs and symptoms NEC | 11 (13.9%) | 10 (12.3%) | 21 (13.1%) | 21 (13.0%) | 15 (9.3%) | 36 (11.2%) |
| Dizziness | 11 (13.9%) | 10 (12.3%) | 21 (13.1%) | 19 (11.8%) | 15 (9.3%) | 34 (10.6%) |
| Presyncope | 0 | 0 | 0 | 2 (1.2%) | 0 | 2 (0.6%) |
| HLT: Paraesthesias and dysaesthesias | 1 (1.3%) | 2 (2.5%) | 3 (1.9%) | 4 (2.5%) | 1 (0.6%) | 5 (1.6%) |
| Paraesthesia | 1 (1.3%) | 2 (2.5%) | 3 (1.9%) | 3 (1.9%) | 1 (0.6%) | 4 (1.2%) |
| HLT: Sensory abnormalities NEC | 0 | 1 (1.2%) | 1 (0.6%) | 1 (0.6%) | 3 (1.9%) | 4 (1.2%) |
| Hypoaesthesia | 0 | 0 | 0 | 1 (0.6%) | 2 (1.2%) | 3 (0.9%) |
| HLGT: Peripheral neuropathies | 5 (6.3%) | 0 | 5 (3.1%) | 4 (2.5%) | 6 (3.7%) | 10 (3.1%) |
| HLT: Chronic polyneuropathies | 2 (2.5%) | 0 | 2 (1.3%) | 2 (1.2%) | 3 (1.9%) | 5 (1.6%) |
| Diabetic neuropathy | 2 (2.5%) | 0 | 2 (1.3%) | 2 (1.2%) | 3 (1.9%) | 5 (1.6%) |
| HLT: Peripheral neuropathies NEC | 2 (2.5%) | 0 | 2 (1.3%) | 1 (0.6%) | 1 (0.6%) | 2 (0.6%) |
| Neuropathy peripheral | 2 (2.5%) | 0 | 2 (1.3%) | 1 (0.6%) | 0 | 1 (0.3%) |
| HLGT: Spinal cord and nerve root disorders | 1 (1.3%) | 3 (3.7%) | 4 (2.5%) | 0 | 4 (2.5%) | 4 (1.2%) |
| HLT: Cervical spinal cord and nerve root disorders | 1 (1.3%) | 1 (1.2%) | 2 (1.3%) | 0 | 0 | 0 |
| Cervicobrachial syndrome | 1 (1.3%) | 1 (1.2%) | 2 (1.3%) | 0 | 0 | 0 |
| HLT: Spinal cord and nerve root disorders NEC | 0 | 0 | 0 | 0 | 2 (1.2%) | 2 (0.6%) |
| Radiculopathy | 0 | 0 | 0 | 0 | 2 (1.2%) | 2 (0.6%) |
| EYE DISORDERS | 8 (10.1%) | 2 (2.5%) | 10 (6.3%) | 14 (8.7%) | 11 (6.8%) | 25 (7.8%) |
| HLGT: Anterior eye structural change, deposit and degeneration | 1 (1.3%) | 0 | 1 (0.6%) | 3 (1.9%) | 4 (2.5%) | 7 (2.2%) |
| HLT: Cataract conditions | 0 | 0 | 0 | 3 (1.9%) | 4 (2.5%) | 7 (2.2%) |
| Cataract | 0 | 0 | 0 | 3 (1.9%) | 4 (2.5%) | 7 (2.2%) |
| HLGT: Ocular infections, irritations and inflammations | 1 (1.3%) | 1 (1.2%) | 2 (1.3%) | 2 (1.2%) | 2 (1.2%) | 4 (1.2%) |
| HLT: Conjunctival infections, irritations and inflammations | 1 (1.3%) | 1 (1.2%) | 2 (1.3%) | 1 (0.6%) | 2 (1.2%) | 3 (0.9%) |
| Conjunctivitis | 1 (1.3%) | 1 (1.2%) | 2 (1.3%) | 1 (0.6%) | 2 (1.2%) | 3 (0.9%) |
| HLGT: Vision disorders | 2 (2.5%) | 0 | 2 (1.3%) | 7 (4.3%) | 5 (3.1%) | 12 (3.7%) |
| HLT: Visual disorders NEC | 1 (1.3%) | 0 | 1 (0.6%) | 4 (2.5%) | 3 (1.9%) | 7 (2.2%) |
| Vision blurred | 1 (1.3%) | 0 | 1 (0.6%) | 3 (1.9%) | 2 (1.2%) | 5 (1.6%) |
| EAR AND LABYRINTH DISORDERS | 3 (3.8%) | 5 (6.2%) | 8 (5.0%) | 4 (2.5%) | 6 (3.7%) | 10 (3.1%) |
| HLGT: Aural disorders NEC | 1 (1.3%) | 1 (1.2%) | 2 (1.3%) | 1 (0.6%) | 1 (0.6%) | 2 (0.6%) |
| HLT: Ear disorders NEC | 1 (1.3%) | 1 (1.2%) | 2 (1.3%) | 1 (0.6%) | 1 (0.6%) | 2 (0.6%) |
| Ear pain | 1 (1.3%) | 1 (1.2%) | 2 (1.3%) | 1 (0.6%) | 1 (0.6%) | 2 (0.6%) |
| HLGT: Inner ear and VIIIth cranial nerve disorders | 2 (2.5%) | 4 (4.9%) | 6 (3.8%) | 4 (2.5%) | 5 (3.1%) | 9 (2.8%) |
| HLT: Inner ear signs and symptoms | 2 (2.5%) | 4 (4.9%) | 6 (3.8%) | 4 (2.5%) | 5 (3.1%) | 9 (2.8%) |
| Tinnitus | 2 (2.5%) | 1 (1.2%) | 3 (1.9%) | 0 | 0 | 0 |
| Vertigo | 0 | 3 (3.7%) | 3 (1.9%) | 4 (2.5%) | 4 (2.5%) | 8 (2.5%) |
| CARDIAC DISORDERS | 8 (10.1%) | 4 (4.9%) | 12 (7.5%) | 10 (6.2%) | 16 (9.9%) | 26 (8.1%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term<br>HLT: High Level Term<br>Preferred Term | Two-step<br>Titration<br>(N = 79) | One-step<br>Titration<br>(N = 81) | Combined<br>(N = 160) | Two-step<br>Titration<br>(N = 161) | One-step<br>Titration<br>(N = 161) | Combined<br>(N = 322) |
| HLGT: Cardiac arrhythmias | 5 (6.3%) | 2 (2.5%) | 7 (4.4%) | 7 (4.3%) | 9 (5.6%) | 16 (5.0%) |
| HLT: Supraventricular arrhythmias | 2 (2.5%) | 1 (1.2%) | 3 (1.9%) | 2 (1.2%) | 9 (5.6%) | 11 (3.4%) |
| Atrial fibrillation | 2 (2.5%) | 0 | 2 (1.3%) | 2 (1.2%) | 3 (1.9%) | 5 (1.6%) |
| Sinus tachycardia | 0 | 0 | 0 | 0 | 3 (1.9%) | 3 (0.9%) |
| Supraventricular extrasystoles | 0 | 1 (1.2%) | 1 (0.6%) | 0 | 2 (1.2%) | 2 (0.6%) |
| HLT: Ventricular arrhythmias and cardiac arrest | 2 (2.5%) | 0 | 2 (1.3%) | 0 | 1 (0.6%) | 1 (0.3%) |
| Ventricular extrasystoles | 2 (2.5%) | 0 | 2 (1.3%) | 0 | 1 (0.6%) | 1 (0.3%) |
| HLGT: Cardiac disorder signs and symptoms | 2 (2.5%) | 1 (1.2%) | 3 (1.9%) | 1 (0.6%) | 3 (1.9%) | 4 (1.2%) |
| HLT: Cardiac signs and symptoms NEC | 2 (2.5%) | 1 (1.2%) | 3 (1.9%) | 1 (0.6%) | 3 (1.9%) | 4 (1.2%) |
| Palpitations | 2 (2.5%) | 1 (1.2%) | 3 (1.9%) | 1 (0.6%) | 3 (1.9%) | 4 (1.2%) |
| HLGT: Coronary artery disorders | 3 (3.8%) | 1 (1.2%) | 4 (2.5%) | 1 (0.6%) | 6 (3.7%) | 7 (2.2%) |
| HLT: Ischaemic coronary artery disorders | 1 (1.3%) | 1 (1.2%) | 2 (1.3%) | 1 (0.6%) | 6 (3.7%) | 7 (2.2%) |
| Acute myocardial infarction | 0 | 0 | 0 | 0 | 2 (1.2%) | 2 (0.6%) |
| Angina unstable | 0 | 0 | 0 | 0 | 2 (1.2%) | 2 (0.6%) |
| Myocardial ischaemia | 1 (1.3%) | 0 | 1 (0.6%) | 0 | 2 (1.2%) | 2 (0.6%) |
| HLGT: Heart failures | 1 (1.3%) | 0 | 1 (0.6%) | 0 | 2 (1.2%) | 2 (0.6%) |
| HLT: Heart failures NEC | 1 (1.3%) | 0 | 1 (0.6%) | 0 | 2 (1.2%) | 2 (0.6%) |
| Cardiac failure | 1 (1.3%) | 0 | 1 (0.6%) | 0 | 2 (1.2%) | 2 (0.6%) |
| VASCULAR DISORDERS | 5 (6.3%) | 14 (17.3%) | 19 (11.9%) | 20 (12.4%) | 18 (11.2%) | 38 (11.8%) |
| HLGT: Arteriosclerosis, stenosis, vascular insufficiency and necrosis | 0 | 2 (2.5%) | 2 (1.3%) | 2 (1.2%) | 5 (3.1%) | 7 (2.2%) |
| HLT: Non-site specific necrosis and vascular insufficiency NEC | 0 | 0 | 0 | 1 (0.6%) | 2 (1.2%) | 3 (0.9%) |
| Venous insufficiency | 0 | 0 | 0 | 1 (0.6%) | 2 (1.2%) | 3 (0.9%) |
| HLGT: Decreased and nonspecific blood pressure disorders and shock | 1 (1.3%) | 0 | 1 (0.6%) | 4 (2.5%) | 3 (1.9%) | 7 (2.2%) |
| HLT: Vascular hypotensive disorders | 1 (1.3%) | 0 | 1 (0.6%) | 4 (2.5%) | 2 (1.2%) | 6 (1.9%) |
| Hypotension | 1 (1.3%) | 0 | 1 (0.6%) | 3 (1.9%) | 2 (1.2%) | 5 (1.6%) |
| HLGT: Vascular hypertensive disorders | 3 (3.8%) | 12 (14.8%) | 15 (9.4%) | 13 (8.1%) | 10 (6.2%) | 23 (7.1%) |
| HLT: Accelerated and malignant hypertension | 2 (2.5%) | 1 (1.2%) | 3 (1.9%) | 0 | 0 | 0 |
| Hypertensive crisis | 2 (2.5%) | 1 (1.2%) | 3 (1.9%) | 0 | 0 | 0 |
| HLT: Vascular hypertensive disorders NEC | 2 (2.5%) | 11 (13.6%) | 13 (8.1%) | 13 (8.1%) | 10 (6.2%) | 23 (7.1%) |
| Hypertension | 2 (2.5%) | 10 (12.3%) | 12 (7.5%) | 12 (7.5%) | 10 (6.2%) | 22 (6.8%) |
| RESPIRATORY, THORACIC AND MEDIASTINAL DISORDERS | 11 (13.9%) | 6 (7.4%) | 17 (10.6%) | 14 (8.7%) | 13 (8.1%) | 27 (8.4%) |
| HLGT: Bronchial disorders (excl neoplasms) | 1 (1.3%) | 3 (3.7%) | 4 (2.5%) | 3 (1.9%) | 0 | 3 (0.9%) |
| HLT: Bronchospasm and obstruction | 1 (1.3%) | 3 (3.7%) | 4 (2.5%) | 3 (1.9%) | 0 | 3 (0.9%) |
| Asthma | 1 (1.3%) | 2 (2.5%) | 3 (1.9%) | 2 (1.2%) | 0 | 2 (0.6%) |
| HLGT: Respiratory disorders NEC | 5 (6.3%) | 3 (3.7%) | 8 (5.0%) | 10 (6.2%) | 11 (6.8%) | 21 (6.5%) |
| HLT: Breathing abnormalities | 1 (1.3%) | 2 (2.5%) | 3 (1.9%) | 0 | 1 (0.6%) | 1 (0.3%) |
| Dyspnoea | 1 (1.3%) | 2 (2.5%) | 3 (1.9%) | 0 | 1 (0.6%) | 1 (0.3%) |
| HLT: Coughing and associated symptoms | 3 (3.8%) | 1 (1.2%) | 4 (2.5%) | 5 (3.1%) | 8 (5.0%) | 13 (4.0%) |
| Cough | 3 (3.8%) | 1 (1.2%) | 4 (2.5%) | 5 (3.1%) | 6 (3.7%) | 11 (3.4%) |
| Productive cough | 0 | 0 | 0 | 1 (0.6%) | 2 (1.2%) | 3 (0.9%) |
| HLT: Upper respiratory tract signs and symptoms | 2 (2.5%) | 0 | 2 (1.3%) | 5 (3.1%) | 3 (1.9%) | 8 (2.5%) |
| Oropharyngeal pain | 2 (2.5%) | 0 | 2 (1.3%) | 5 (3.1%) | 0 | 5 (1.6%) |
| Rhinorrhoea | 0 | 0 | 0 | 0 | 2 (1.2%) | 2 (0.6%) |
| HLGT: Upper respiratory tract disorders (excl infections) | 4 (5.1%) | 1 (1.2%) | 5 (3.1%) | 3 (1.9%) | 2 (1.2%) | 5 (1.6%) |
| HLT: Nasal congestion and inflammations | 1 (1.3%) | 1 (1.2%) | 2 (1.3%) | 1 (0.6%) | 0 | 1 (0.3%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term<br>HLT: High Level Term<br>Preferred Term | Two-step<br>Titration<br>(N = 79) | One-step<br>Titration<br>(N = 81) | Combined<br>(N = 160) | Two-step<br>Titration<br>(N = 161) | One-step<br>Titration<br>(N = 161) | Combined<br>(N = 322) |
| Rhinitis allergic | 1 (1.3%) | 1 (1.2%) | 2 (1.3%) | 1 (0.6%) | 0 | 1 (0.3%) |
| HLT: Nasal disorders NEC | 3 (3.8%) | 0 | 3 (1.9%) | 2 (1.2%) | 2 (1.2%) | 4 (1.2%) |
| Epistaxis | 3 (3.8%) | 0 | 3 (1.9%) | 1 (0.6%) | 2 (1.2%) | 3 (0.9%) |
| GASTROINTESTINAL DISORDERS | 26 (32.9%) | 24 (29.6%) | 50 (31.3%) | 90 (55.9%) | 83 (51.6%) | 173 (53.7%) |
| HLGT: Abdominal hernias and other abdominal wall conditions | 2 (2.5%) | 0 | 2 (1.3%) | 4 (2.5%) | 0 | 4 (1.2%) |
| HLT: Inguinal hernias | 1 (1.3%) | 0 | 1 (0.6%) | 2 (1.2%) | 0 | 2 (0.6%) |
| Inguinal hernia | 1 (1.3%) | 0 | 1 (0.6%) | 2 (1.2%) | 0 | 2 (0.6%) |
| HLGT: Dental and gingival conditions | 5 (6.3%) | 7 (8.6%) | 12 (7.5%) | 10 (6.2%) | 8 (5.0%) | 18 (5.6%) |
| HLT: Dental pain and sensation disorders | 3 (3.8%) | 2 (2.5%) | 5 (3.1%) | 8 (5.0%) | 4 (2.5%) | 12 (3.7%) |
| Toothache | 3 (3.8%) | 2 (2.5%) | 5 (3.1%) | 8 (5.0%) | 4 (2.5%) | 12 (3.7%) |
| HLT: Gingival disorders NEC | 1 (1.3%) | 0 | 1 (0.6%) | 1 (0.6%) | 3 (1.9%) | 4 (1.2%) |
| Gingivitis | 1 (1.3%) | 0 | 1 (0.6%) | 1 (0.6%) | 3 (1.9%) | 4 (1.2%) |
| HLT: Gingival pains | 0 | 2 (2.5%) | 2 (1.3%) | 0 | 0 | 0 |
| Gingival pain | 0 | 2 (2.5%) | 2 (1.3%) | 0 | 0 | 0 |
| HLGT: Gastrointestinal conditions NEC | 1 (1.3%) | 2 (2.5%) | 3 (1.9%) | 2 (1.2%) | 1 (0.6%) | 3 (0.9%) |
| HLT: Gastrointestinal disorders NEC | 0 | 2 (2.5%) | 2 (1.3%) | 0 | 1 (0.6%) | 1 (0.3%) |
| Food poisoning | 0 | 2 (2.5%) | 2 (1.3%) | 0 | 1 (0.6%) | 1 (0.3%) |
| HLT: Gastrointestinal mucosal dystrophies and secretion disorders | 1 (1.3%) | 0 | 1 (0.6%) | 2 (1.2%) | 0 | 2 (0.6%) |
| Hyperchlorhydria | 1 (1.3%) | 0 | 1 (0.6%) | 2 (1.2%) | 0 | 2 (0.6%) |
| HLGT: Gastrointestinal inflammatory conditions | 8 (10.1%) | 2 (2.5%) | 10 (6.3%) | 8 (5.0%) | 8 (5.0%) | 16 (5.0%) |
| HLT: Colitis (excl infective) | 1 (1.3%) | 2 (2.5%) | 3 (1.9%) | 0 | 2 (1.2%) | 2 (0.6%) |
| Colitis | 1 (1.3%) | 2 (2.5%) | 3 (1.9%) | 0 | 2 (1.2%) | 2 (0.6%) |
| HLT: Gastritis (excl infective) | 5 (6.3%) | 0 | 5 (3.1%) | 8 (5.0%) | 7 (4.3%) | 15 (4.7%) |
| Gastritis | 5 (6.3%) | 0 | 5 (3.1%) | 8 (5.0%) | 7 (4.3%) | 15 (4.7%) |
| HLGT: Gastrointestinal motility and defaecation conditions | 13 (16.5%) | 11 (13.6%) | 24 (15.0%) | 31 (19.3%) | 23 (14.3%) | 54 (16.8%) |
| HLT: Diarrhoea (excl infective) | 10 (12.7%) | 11 (13.6%) | 21 (13.1%) | 24 (14.9%) | 16 (9.9%) | 40 (12.4%) |
| Diarrhoea | 10 (12.7%) | 11 (13.6%) | 21 (13.1%) | 24 (14.9%) | 16 (9.9%) | 40 (12.4%) |
| HLT: Gastrointestinal atonic and hypomotility disorders NEC | 6 (7.6%) | 0 | 6 (3.8%) | 11 (6.8%) | 3 (1.9%) | 14 (4.3%) |
| Constipation | 4 (5.1%) | 0 | 4 (2.5%) | 11 (6.8%) | 2 (1.2%) | 13 (4.0%) |
| Gastrooesophageal reflux disease | 2 (2.5%) | 0 | 2 (1.3%) | 0 | 1 (0.6%) | 1 (0.3%) |
| HLT: Gastrointestinal spastic and hypermotility disorders | 0 | 1 (1.2%) | 1 (0.6%) | 1 (0.6%) | 5 (3.1%) | 6 (1.9%) |
| Irritable bowel syndrome | 0 | 1 (1.2%) | 1 (0.6%) | 0 | 4 (2.5%) | 4 (1.2%) |
| HLGT: Gastrointestinal signs and symptoms | 12 (15.2%) | 11 (13.6%) | 23 (14.4%) | 75 (46.6%) | 67 (41.6%) | 142 (44.1%) |
| HLT: Dyspeptic signs and symptoms | 0 | 1 (1.2%) | 1 (0.6%) | 7 (4.3%) | 10 (6.2%) | 17 (5.3%) |
| Dyspepsia | 0 | 1 (1.2%) | 1 (0.6%) | 7 (4.3%) | 9 (5.6%) | 16 (5.0%) |
| HLT: Flatulence, bloating and distension | 1 (1.3%) | 1 (1.2%) | 2 (1.3%) | 5 (3.1%) | 8 (5.0%) | 13 (4.0%) |
| Abdominal distension | 1 (1.3%) | 1 (1.2%) | 2 (1.3%) | 4 (2.5%) | 4 (2.5%) | 8 (2.5%) |
| Flatulence | 0 | 0 | 0 | 1 (0.6%) | 4 (2.5%) | 5 (1.6%) |
| HLT: Gastrointestinal and abdominal pains (excl oral and throat) | 4 (5.1%) | 5 (6.2%) | 9 (5.6%) | 14 (8.7%) | 12 (7.5%) | 26 (8.1%) |
| Abdominal pain | 3 (3.8%) | 4 (4.9%) | 7 (4.4%) | 9 (5.6%) | 8 (5.0%) | 17 (5.3%) |
| Abdominal pain upper | 1 (1.3%) | 1 (1.2%) | 2 (1.3%) | 6 (3.7%) | 4 (2.5%) | 10 (3.1%) |
| HLT: Gastrointestinal signs and symptoms NEC | 0 | 1 (1.2%) | 1 (0.6%) | 0 | 2 (1.2%) | 2 (0.6%) |
| Abdominal discomfort | 0 | 0 | 0 | 0 | 2 (1.2%) | 2 (0.6%) |
| HLT: Nausea and vomiting symptoms | 9 (11.4%) | 5 (6.2%) | 14 (8.8%) | 65 (40.4%) | 52 (32.3%) | 117 (36.3%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term HLT: High Level Term Preferred Term | Two-step Titration (N = 79) | One-step Titration (N = 81) | Combined (N = 160) | Two-step Titration (N = 161) | One-step Titration (N = 161) | Combined (N = 322) |
| Nausea | 8 (10.1%) | 5 (6.2%) | 13 (8.1%) | 62 (38.5%) | 47 (29.2%) | 109 (33.9%) |
| Vomiting | 1 (1.3%) | 0 | 1 (0.6%) | 29 (18.0%) | 21 (13.0%) | 50 (15.5%) |
| HLGT: Gastrointestinal vascular conditions | 0 | 0 | 0 | 0 | 2 (1.2%) | 2 (0.6%) |
| HLT: Haemorrhoids and gastrointestinal varices (excl oesophageal) | 0 | 0 | 0 | 0 | 2 (1.2%) | 2 (0.6%) |
| Haemorrhoids | 0 | 0 | 0 | 0 | 2 (1.2%) | 2 (0.6%) |
| HLGT: Salivary gland conditions | 2 (2.5%) | 0 | 2 (1.3%) | 2 (1.2%) | 0 | 2 (0.6%) |
| HLT: Oral dryness and saliva altered | 1 (1.3%) | 0 | 1 (0.6%) | 2 (1.2%) | 0 | 2 (0.6%) |
| Dry mouth | 1 (1.3%) | 0 | 1 (0.6%) | 2 (1.2%) | 0 | 2 (0.6%) |
| HEPATOBILIARY DISORDERS | 3 (3.8%) | 2 (2.5%) | 5 (3.1%) | 2 (1.2%) | 5 (3.1%) | 7 (2.2%) |
| HLGT: Gallbladder disorders | 2 (2.5%) | 1 (1.2%) | 3 (1.9%) | 1 (0.6%) | 2 (1.2%) | 3 (0.9%) |
| HLT: Cholecystitis and cholelithiasis | 2 (2.5%) | 1 (1.2%) | 3 (1.9%) | 1 (0.6%) | 2 (1.2%) | 3 (0.9%) |
| Cholecystitis | 1 (1.3%) | 1 (1.2%) | 2 (1.3%) | 1 (0.6%) | 0 | 1 (0.3%) |
| Cholecystitis acute | 1 (1.3%) | 0 | 1 (0.6%) | 0 | 2 (1.2%) | 2 (0.6%) |
| HLGT: Hepatic and hepatobiliary disorders | 1 (1.3%) | 1 (1.2%) | 2 (1.3%) | 1 (0.6%) | 3 (1.9%) | 4 (1.2%) |
| HLT: Hepatocellular damage and hepatitis NEC | 1 (1.3%) | 1 (1.2%) | 2 (1.3%) | 1 (0.6%) | 2 (1.2%) | 3 (0.9%) |
| Hepatic steatosis | 1 (1.3%) | 1 (1.2%) | 2 (1.3%) | 1 (0.6%) | 2 (1.2%) | 3 (0.9%) |
| SKIN AND SUBCUTANEOUS TISSUE DISORDERS | 12 (15.2%) | 9 (11.1%) | 21 (13.1%) | 14 (8.7%) | 15 (9.3%) | 29 (9.0%) |
| HLGT: Epidermal and dermal conditions | 5 (6.3%) | 7 (8.6%) | 12 (7.5%) | 8 (5.0%) | 10 (6.2%) | 18 (5.6%) |
| HLT: Dermatitis and eczema | 4 (5.1%) | 1 (1.2%) | 5 (3.1%) | 3 (1.9%) | 4 (2.5%) | 7 (2.2%) |
| Dermatitis | 2 (2.5%) | 1 (1.2%) | 3 (1.9%) | 0 | 0 | 0 |
| Dermatitis allergic | 0 | 0 | 0 | 2 (1.2%) | 1 (0.6%) | 3 (0.9%) |
| Skin irritation | 2 (2.5%) | 0 | 2 (1.3%) | 0 | 0 | 0 |
| HLT: Pruritus NEC | 0 | 3 (3.7%) | 3 (1.9%) | 5 (3.1%) | 2 (1.2%) | 7 (2.2%) |
| Pruritus | 0 | 3 (3.7%) | 3 (1.9%) | 3 (1.9%) | 1 (0.6%) | 4 (1.2%) |
| Pruritus generalised | 0 | 0 | 0 | 2 (1.2%) | 0 | 2 (0.6%) |
| HLT: Rashes, eruptions and exanthems NEC | 1 (1.3%) | 1 (1.2%) | 2 (1.3%) | 0 | 0 | 0 |
| Rash | 1 (1.3%) | 1 (1.2%) | 2 (1.3%) | 0 | 0 | 0 |
| HLGT: Skin appendage conditions | 6 (7.6%) | 2 (2.5%) | 8 (5.0%) | 6 (3.7%) | 5 (3.1%) | 11 (3.4%) |
| HLT: Alopecias | 1 (1.3%) | 0 | 1 (0.6%) | 2 (1.2%) | 3 (1.9%) | 5 (1.6%) |
| Alopecia | 1 (1.3%) | 0 | 1 (0.6%) | 2 (1.2%) | 3 (1.9%) | 5 (1.6%) |
| HLT: Apocrine and eccrine gland disorders | 5 (6.3%) | 1 (1.2%) | 6 (3.8%) | 3 (1.9%) | 1 (0.6%) | 4 (1.2%) |
| Hyperhidrosis | 3 (3.8%) | 1 (1.2%) | 4 (2.5%) | 3 (1.9%) | 1 (0.6%) | 4 (1.2%) |
| HLGT: Skin vascular abnormalities | 1 (1.3%) | 2 (2.5%) | 3 (1.9%) | 0 | 0 | 0 |
| HLT: Purpura and related conditions | 1 (1.3%) | 2 (2.5%) | 3 (1.9%) | 0 | 0 | 0 |
| Ecchymosis | 1 (1.3%) | 2 (2.5%) | 3 (1.9%) | 0 | 0 | 0 |
| MUSCULOSKELETAL AND CONNECTIVE TISSUE DISORDERS | 27 (34.2%) | 18 (22.2%) | 45 (28.1%) | 42 (26.1%) | 38 (23.6%) | 80 (24.8%) |
| HLGT: Bone disorders (excl congenital and fractures) | 0 | 0 | 0 | 0 | 2 (1.2%) | 2 (0.6%) |
| HLT: Bone disorders NEC | 0 | 0 | 0 | 0 | 2 (1.2%) | 2 (0.6%) |
| Exostosis | 0 | 0 | 0 | 0 | 2 (1.2%) | 2 (0.6%) |
| HLGT: Joint disorders | 14 (17.7%) | 7 (8.6%) | 21 (13.1%) | 16 (9.9%) | 16 (9.9%) | 32 (9.9%) |
| HLT: Joint related signs and symptoms | 9 (11.4%) | 5 (6.2%) | 14 (8.8%) | 12 (7.5%) | 10 (6.2%) | 22 (6.8%) |
| Arthralgia | 9 (11.4%) | 5 (6.2%) | 14 (8.8%) | 11 (6.8%) | 9 (5.6%) | 20 (6.2%) |
| HLT: Osteoarthropathies | 6 (7.6%) | 2 (2.5%) | 8 (5.0%) | 5 (3.1%) | 6 (3.7%) | 11 (3.4%) |
| Osteoarthritis | 5 (6.3%) | 2 (2.5%) | 7 (4.4%) | 4 (2.5%) | 5 (3.1%) | 9 (2.8%) |
| HLGT: Muscle disorders | 6 (7.6%) | 5 (6.2%) | 11 (6.9%) | 5 (3.1%) | 8 (5.0%) | 13 (4.0%) |
| HLT: Muscle pains | 4 (5.1%) | 4 (4.9%) | 8 (5.0%) | 2 (1.2%) | 4 (2.5%) | 6 (1.9%) |
| Myalgia | 4 (5.1%) | 4 (4.9%) | 8 (5.0%) | 2 (1.2%) | 4 (2.5%) | 6 (1.9%) |
| HLT: Muscle related signs and symptoms NEC | 3 (3.8%) | 1 (1.2%) | 4 (2.5%) | 3 (1.9%) | 5 (3.1%) | 8 (2.5%) |
| Muscle spasms | 2 (2.5%) | 1 (1.2%) | 3 (1.9%) | 3 (1.9%) | 5 (3.1%) | 8 (2.5%) |
| HLGT: Musculoskeletal and connective tissue disorders NEC | 16 (20.3%) | 9 (11.1%) | 25 (15.6%) | 27 (16.8%) | 22 (13.7%) | 49 (15.2%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term<br>HLT: High Level Term<br>Preferred Term | Two-step Titration (N = 79) | One-step Titration (N = 81) | Combined (N = 160) | Two-step Titration (N = 161) | One-step Titration (N = 161) | Combined (N = 322) |
| HLT: Musculoskeletal and connective tissue pain and discomfort | 14 (17.7%) | 9 (11.1%) | 23 (14.4%) | 25 (15.5%) | 21 (13.0%) | 46 (14.3%) |
| Back pain | 8 (10.1%) | 3 (3.7%) | 11 (6.9%) | 15 (9.3%) | 18 (11.2%) | 33 (10.2%) |
| Musculoskeletal chest pain | 2 (2.5%) | 1 (1.2%) | 3 (1.9%) | 0 | 1 (0.6%) | 1 (0.3%) |
| Musculoskeletal pain | 1 (1.3%) | 4 (4.9%) | 5 (3.1%) | 4 (2.5%) | 3 (1.9%) | 7 (2.2%) |
| Neck pain | 1 (1.3%) | 1 (1.2%) | 2 (1.3%) | 2 (1.2%) | 0 | 2 (0.6%) |
| Pain in extremity | 5 (6.3%) | 3 (3.7%) | 8 (5.0%) | 4 (2.5%) | 3 (1.9%) | 7 (2.2%) |
| HLT: Musculoskeletal and connective tissue signs and symptoms NEC | 2 (2.5%) | 0 | 2 (1.3%) | 1 (0.6%) | 1 (0.6) | 2 (0.6%) |
| Muscle contracture | 2 (2.5%) | 0 | 2 (1.3%) | 1 (0.6%) | 0 | 1 (0.3%) |
| RENAL AND URINARY DISORDERS | 6 (7.6%) | 4 (4.9%) | 10 (6.3%) | 7 (4.3%) | 11 (6.8%) | 18 (5.6%) |
| HLGT: Renal disorders (excl nephropathies) | 2 (2.5%) | 0 | 2 (1.3%) | 2 (1.2%) | 1 (0.6%) | 3 (0.9%) |
| HLT: Renal failure and impairment | 2 (2.5%) | 0 | 2 (1.3%) | 2 (1.2%) | 1 (0.6%) | 3 (0.9%) |
| Renal impairment | 2 (2.5%) | 0 | 2 (1.3%) | 1 (0.6%) | 0 | 1 (0.3%) |
| HLGT: Urinary tract signs and symptoms | 4 (5.1%) | 3 (3.7%) | 7 (4.4%) | 5 (3.1%) | 9 (5.6%) | 14 (4.3%) |
| HLT: Bladder and urethral symptoms | 3 (3.8%) | 2 (2.5%) | 5 (3.1%) | 2 (1.2%) | 4 (2.5%) | 6 (1.9%) |
| Dysuria | 2 (2.5%) | 1 (1.2%) | 3 (1.9%) | 1 (0.6%) | 4 (2.5%) | 5 (1.6%) |
| HLT: Urinary abnormalities | 0 | 1 (1.2%) | 1 (0.6%) | 2 (1.2%) | 0 | 2 (0.6%) |
| Haematuria | 0 | 0 | 0 | 2 (1.2%) | 0 | 2 (0.6%) |
| HLT: Urinary tract signs and symptoms NEC | 1 (1.3%) | 0 | 1 (0.6%) | 1 (0.6%) | 5 (3.1%) | 6 (1.9%) |
| Renal colic | 1 (1.3%) | 0 | 1 (0.6%) | 1 (0.6%) | 3 (1.9%) | 4 (1.2%) |
| REPRODUCTIVE SYSTEM AND BREAST DISORDERS | 5 (6.3%) | 0 | 5 (3.1%) | 3 (1.9%) | 6 (3.7%) | 9 (2.8%) |
| HLGT: Prostatic disorders (excl infections and inflammations) | 2 (2.5%) | 0 | 2 (1.3%) | 1 (0.6%) | 2 (1.2%) | 3 (0.9%) |
| HLT: Prostatic neoplasms and hypertrophy | 2 (2.5%) | 0 | 2 (1.3%) | 1 (0.6%) | 2 (1.2%) | 3 (0.9%) |
| Benign prostatic hyperplasia | 2 (2.5%) | 0 | 2 (1.3%) | 1 (0.6%) | 2 (1.2%) | 3 (0.9%) |
| GENERAL DISORDERS AND ADMINISTRATION SITE CONDITIONS | 9 (11.4%) | 12 (14.8%) | 21 (13.1%) | 30 (18.6%) | 24 (14.9%) | 54 (16.8%) |
| HLGT: Administration site reactions | 1 (1.3%) | 2 (2.5%) | 3 (1.9%) | 9 (5.6%) | 8 (5.0%) | 17 (5.3%) |
| HLT: Injection site reactions | 1 (1.3%) | 2 (2.5%) | 3 (1.9%) | 9 (5.6%) | 8 (5.0%) | 17 (5.3%) |
| Injection site erythema | 0 | 0 | 0 | 4 (2.5%) | 2 (1.2%) | 6 (1.9%) |
| Injection site macule | 0 | 0 | 0 | 1 (0.6%) | 2 (1.2%) | 3 (0.9%) |
| Injection site pain | 0 | 1 (1.2%) | 1 (0.6%) | 2 (1.2%) | 2 (1.2%) | 4 (1.2%) |
| Injection site pruritus | 0 | 0 | 0 | 3 (1.9%) | 3 (1.9%) | 6 (1.9%) |
| HLGT: Body temperature conditions | 0 | 1 (1.2%) | 1 (0.6%) | 4 (2.5%) | 3 (1.9%) | 7 (2.2%) |
| HLT: Febrile disorders | 0 | 1 (1.2%) | 1 (0.6%) | 4 (2.5%) | 3 (1.9%) | 7 (2.2%) |
| Pyrexia | 0 | 1 (1.2%) | 1 (0.6%) | 4 (2.5%) | 3 (1.9%) | 7 (2.2%) |
| HLGT: General system disorders NEC | 8 (10.1%) | 9 (11.1%) | 17 (10.6%) | 22 (13.7%) | 15 (9.3%) | 37 (11.5%) |
| HLT: Asthenic conditions | 3 (3.8%) | 5 (6.2%) | 8 (5.0%) | 16 (9.9%) | 6 (3.7%) | 22 (6.8%) |
| Asthenia | 0 | 1 (1.2%) | 1 (0.6%) | 9 (5.6%) | 3 (1.9%) | 12 (3.7%) |
| Fatigue | 3 (3.8%) | 2 (2.5%) | 5 (3.1%) | 3 (1.9%) | 2 (1.2%) | 5 (1.6%) |
| Malaise | 0 | 2 (2.5%) | 2 (1.3%) | 5 (3.1%) | 1 (0.6%) | 6 (1.9%) |
| HLT: Inflammations | 0 | 0 | 0 | 2 (1.2%) | 0 | 2 (0.6%) |
| Inflammation | 0 | 0 | 0 | 2 (1.2%) | 0 | 2 (0.6%) |
| HLT: Oedema NEC | 4 (5.1%) | 3 (3.7%) | 7 (4.4%) | 4 (2.5%) | 3 (1.9%) | 7 (2.2%) |
| Oedema peripheral | 4 (5.1%) | 3 (3.7%) | 7 (4.4%) | 3 (1.9%) | 3 (1.9%) | 6 (1.9%) |
| HLT: Pain and discomfort NEC | 0 | 0 | 0 | 2 (1.2%) | 2 (1.2%) | 4 (1.2%) |
| Chest pain | 0 | 0 | 0 | 2 (1.2%) | 1 (0.6%) | 3 (0.9%) |
| INVESTIGATIONS | 8 (10.1%) | 11 (13.6%) | 19 (11.9%) | 14 (8.7%) | 15 (9.3%) | 29 (9.0%) |
| HLGT: Cardiac and vascular investigations (excl enzyme tests) | 0 | 2 (2.5%) | 2 (1.3%) | 3 (1.9%) | 2 (1.2%) | 5 (1.6%) |
| HLT: Vascular tests NEC (incl blood pressure) | 0 | 2 (2.5%) | 2 (1.3%) | 2 (1.2%) | 2 (1.2%) | 4 (1.2%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term<br>HLT: High Level Term<br>Preferred Term | Two-step Titration (N = 79) | One-step Titration (N = 81) | Combined (N = 160) | Two-step Titration (N = 161) | One-step Titration (N = 161) | Combined (N = 322) |
| Blood pressure increased | 0 | 2 (2.5%) | 2 (1.3%) | 2 (1.2%) | 2 (1.2%) | 4 (1.2%) |
| HLGT: Endocrine investigations (incl sex hormones) | 0 | 1 (1.2%) | 1 (0.6%) | 4 (2.5%) | 5 (3.1%) | 9 (2.8%) |
| HLT: Gastrointestinal, pancreatic and APUD hormone analyses | 0 | 1 (1.2%) | 1 (0.6%) | 4 (2.5%) | 3 (1.9%) | 7 (2.2%) |
| Blood calcitonin increased | 0 | 1 (1.2%) | 1 (0.6%) | 4 (2.5%) | 3 (1.9%) | 7 (2.2%) |
| HLGT: Gastrointestinal investigations | 1 (1.3%) | 4 (4.9%) | 5 (3.1%) | 4 (2.5%) | 7 (4.3%) | 11 (3.4%) |
| HLT: Digestive enzymes | 1 (1.3%) | 4 (4.9%) | 5 (3.1%) | 4 (2.5%) | 7 (4.3%) | 11 (3.4%) |
| Blood amylase increased | 1 (1.3%) | 0 | 1 (0.6%) | 0 | 2 (1.2%) | 2 (0.6%) |
| Lipase increased | 0 | 3 (3.7%) | 3 (1.9%) | 4 (2.5%) | 4 (2.5%) | 8 (2.5%) |
| HLGT: Hepatobiliary investigations | 3 (3.8%) | 2 (2.5%) | 5 (3.1%) | 2 (1.2%) | 4 (2.5%) | 6 (1.9%) |
| HLT: Liver function analyses | 3 (3.8%) | 2 (2.5%) | 5 (3.1%) | 2 (1.2%) | 4 (2.5%) | 6 (1.9%) |
| Gamma-glutamyltransferase increased | 2 (2.5%) | 0 | 2 (1.3%) | 1 (0.6%) | 0 | 1 (0.3%) |
| Hepatic enzyme increased | 1 (1.3%) | 1 (1.2%) | 2 (1.3%) | 0 | 0 | 0 |
| Transaminases increased | 0 | 0 | 0 | 1 (0.6%) | 2 (1.2%) | 3 (0.9%) |
| HLGT: Metabolic, nutritional and blood gas investigations | 1 (1.3%) | 1 (1.2%) | 2 (1.3%) | 1 (0.6%) | 1 (0.6%) | 2 (0.6%) |
| HLT: Carbohydrate tolerance analyses (incl diabetes) | 1 (1.3%) | 1 (1.2%) | 2 (1.3%) | 1 (0.6%) | 1 (0.6%) | 2 (0.6%) |
| Blood glucose decreased | 1 (1.3%) | 1 (1.2%) | 2 (1.3%) | 1 (0.6%) | 1 (0.6%) | 2 (0.6%) |
| HLGT: Physical examination topics | 1 (1.3%) | 1 (1.2%) | 2 (1.3%) | 0 | 0 | 0 |
| HLT: Physical examination procedures | 1 (1.3%) | 1 (1.2%) | 2 (1.3%) | 0 | 0 | 0 |
| Weight decreased | 1 (1.3%) | 1 (1.2%) | 2 (1.3%) | 0 | 0 | 0 |
| INJURY, POISONING AND PROCEDURAL COMPLICATIONS | 9 (11.4%) | 9 (11.1%) | 18 (11.3%) | 18 (11.2%) | 19 (11.8%) | 37 (11.5%) |
| HLGT: Bone and joint injuries | 7 (8.9%) | 5 (6.2%) | 12 (7.5%) | 7 (4.3%) | 3 (1.9%) | 10 (3.1%) |
| HLT: Limb injuries NEC (incl traumatic amputation) | 3 (3.8%) | 3 (3.7%) | 6 (3.8%) | 5 (3.1%) | 2 (1.2%) | 7 (2.2%) |
| Joint sprain | 2 (2.5%) | 0 | 2 (1.3%) | 2 (1.2%) | 0 | 2 (0.6%) |
| Limb crushing injury | 1 (1.3%) | 1 (1.2%) | 2 (1.3%) | 0 | 0 | 0 |
| Limb injury | 0 | 1 (1.2%) | 1 (0.6%) | 2 (1.2%) | 2 (1.2%) | 4 (1.2%) |
| Meniscus lesion | 1 (1.3%) | 1 (1.2%) | 2 (1.3%) | 1 (0.6%) | 0 | 1 (0.3%) |
| HLT: Lower limb fractures and dislocations | 3 (3.8%) | 1 (1.2%) | 4 (2.5%) | 0 | 0 | 0 |
| Ankle fracture | 2 (2.5%) | 0 | 2 (1.3%) | 0 | 0 | 0 |
| HLGT: Injuries NEC | 3 (3.8%) | 4 (4.9%) | 7 (4.4%) | 12 (7.5%) | 17 (10.6%) | 29 (9.0%) |
| HLT: Chest and lung injuries NEC | 0 | 0 | 0 | 0 | 2 (1.2%) | 2 (0.6%) |
| Chest injury | 0 | 0 | 0 | 0 | 2 (1.2%) | 2 (0.6%) |
| HLT: Non-site specific injuries NEC | 3 (3.8%) | 4 (4.9%) | 7 (4.4%) | 11 (6.8%) | 11 (6.8%) | 22 (6.8%) |
| Arthropod bite | 1 (1.3%) | 1 (1.2%) | 2 (1.3%) | 1 (0.6%) | 0 | 1 (0.3%) |
| Fall | 1 (1.3%) | 4 (4.9%) | 5 (3.1%) | 6 (3.7%) | 7 (4.3%) | 13 (4.0%) |
| Injury | 0 | 0 | 0 | 0 | 2 (1.2%) | 2 (0.6%) |
| Road traffic accident | 0 | 0 | 0 | 2 (1.2%) | 1 (0.6%) | 3 (0.9%) |
| Skeletal injury | 0 | 0 | 0 | 0 | 2 (1.2%) | 2 (0.6%) |
| HLT: Skin injuries NEC | 0 | 2 (2.5%) | 2 (1.3%) | 6 (3.7%) | 11 (6.8%) | 17 (5.3%) |
| Contusion | 0 | 1 (1.2%) | 1 (0.6%) | 4 (2.5%) | 7 (4.3%) | 11 (3.4%) |
| Skin laceration | 0 | 1 (1.2%) | 1 (0.6%) | 2 (1.2%) | 3 (1.9%) | 5 (1.6%) |
| SURGICAL AND MEDICAL PROCEDURES | 2 (2.5%) | 1 (1.2%) | 3 (1.9%) | 2 (1.2%) | 4 (2.5%) | 6 (1.9%) |
| HLGT: Head and neck therapeutic procedures | 1 (1.3%) | 1 (1.2%) | 2 (1.3%) | 1 (0.6%) | 1 (0.6%) | 2 (0.6%) |

TABLE 28-continued

Number (%) of patients experiencing common TEAE(s) (PT ≥1% in the placebo combined or any lixisenatide individual group) presented by primary SOC, HLGT, HLT, and PT during the on-treatment period for the whole study - Safety population

| PRIMARY SYSTEM ORGAN CLASS | Placebo | | | Lixisenatide | | |
|---|---|---|---|---|---|---|
| HLGT: High Level Group Term<br>HLT: High Level Term<br>Preferred Term | Two-step Titration (N = 79) | One-step Titration (N = 81) | Combined (N = 160) | Two-step Titration (N = 161) | One-step Titration (N = 161) | Combined (N = 322) |
| HLT: Dental and gingival therapeutic procedures | 1 (1.3%) | 1 (1.2%) | 2 (1.3%) | 1 (0.6%) | 1 (0.6%) | 2 (0.6%) |
| Tooth extraction | 1 (1.3%) | 1 (1.2%) | 2 (1.3%) | 1 (0.6%) | 0 | 1 (0.3%) |

TEAE: Treatment Emergent Adverse Event,
SOC: System Organ Class,
HLGT: High Level Group Term,
HLT: High Level Term,
PT: Preferred Term.
MedDRA version: 13.1
n (%) = number and percentage of patients with at least one TEAE.
Note:
On-treatment period for the whole study = the time from the first dose of double-blind study medication up to 3 days after the last dose administration.
Table sorted by SOC internationally agreed order and HLGT, HLT, PT by alphabetic order.
Only SOC with at least one PT ≥1% in the placebo combined group or any lixisenatide one- or two-step titration group are presented.

Example 2

A randomized, double-blind, double-dummy, active-controlled, 2-arm parallel-group, multinational study assessing the efficacy and safety of lixisenatide in comparison to sitagliptin as an add-on treatment to metformin in obese type 2 diabetic patients younger than 50 and not adequately controlled with metformin.

The Example refers to a randomized, double-blind, double-dummy, active-controlled, 2-arm parallel-group, multinational study assessing the efficacy and safety of lixisenatide in comparison to sitagliptin as an add-on treatment to metformin in obese type 2 diabetic patients younger than 50 and not adequately controlled with metformin. The approximate study duration per patient was 27 weeks (up to 3 weeks screening+24 weeks double-blind treatment+3 days follow-up). The study was conducted in 92 centers in 13 countries. The primary objective of the study was to assess the efficacy of lixisenatide on a composite endpoint of glycemic control (glycosylated hemoglobin $A_{1c}$ [$HbA_{1c}$]) body weight in comparison to sitagliptin over a period of 24 weeks.

A total of 319 patients were randomized to one of the two treatment groups (158 in the lixisenatide group and 161 in the sitagliptin group). All randomized patients were exposed to the study treatment and were included in the modified intent-to-treat (mITT) population. Demographics and baseline characteristics were generally similar across the treatment groups with more female patients in the lixisenatide group. During the study treatment period, 27 (8.5%) patients prematurely discontinued the study treatment with a higher percentage in the lixisenatide group (10.1%) compared to the sitagliptin group (6.8%). In lixisenatide-treated patients, the main reason for treatment discontinuation was "other reasons" (7 patients: 4.4% versus 5 patients: 3.1% for sitagliptin) followed by "adverse events" (4 patients: 2.5% versus 5 patients: 3.1% for sitagliptin).

The percentage of patients with $HbA_{1c}$<7% at Week 24 and a weight loss of at least 5% of baseline body weight at Week 24 (primary efficacy endpoint) was higher for the lixisenatide group (12.0%) than for the sitagliptin group (7.5%). The treatment difference was not statistically significant (weighted average of response rate difference vs. sitagliptin=4.6%; p-value=0.1696 based on the primary analysis using Cochran-Mantel-Haenszel [CMH] method), due to the lower than the expected response rate for the lixisenatide group. A supportive analysis using a logistic regression model showed a consistent result (p-value=0.1160). A total of 61 patients (40.7%) in the lixisenatide group had $HbA_{1c}$<7% at Week 24 compared to 64 patients (40.0%) in the sitagliptin group, and 36 (24.0%) of lixisenatide-treated patients had $HbA_{1c}$≤6.5% compared to 42 (26.3%) of sitagliptin-treated patients. More lixisenatide-treated patients (28 [18.4%]) had ≥5% weight loss from baseline to Week 24 than sitagliptin-treated patients (19 [11.9%]).

Patients treated with lixisenatide had a significantly greater decrease in body weight than patients treated with sitagliptin (LS mean difference of −1.34 kg; 95% CI [−2.101; −0.575]). Mean changes from baseline to week 24 in $HbA_{1c}$ were similar in the lixisenatide and sitagliptin groups: LS mean of −0.66% and −0.72% respectively. Treatment with lixisenatide significantly improved postprandial glycemic control in comparison to sitagliptin as shown by the results for the 2-hour postprandial plasma glucose (PPG) assessment (LS mean difference of −1.91 mmol/L; 95% CI [−2.876; −0.941]) and for glucose excursion (LS mean difference of −2.13 mmol/L; 95% CI [−2.819; −1.434]). For change from baseline at Week 24 in $HbA_{1c}$, fasting plasma glucose (FPG), insulin resistance assessed by HOMA-IR and β-cell function assessed by HOMA-β, no significant difference was observed between lixisenatide and sitagliptin treatment groups. The percentages of patients requiring rescue therapy were 9.5% in the lixisenatide group and 6.8% in the sitagliptin group, with no significant difference between these two groups.

Lixisenatide was well tolerated. The incidence of treatment emergent adverse events (TEAEs) was slightly higher for lixisenatide-treated patients versus sitagliptin-treated patients (63.9% for lixisenatide versus 60.9% for sitagliptin). Six patients (3 [1.9%] in each group) had a serious TEAE. No death was reported in this study. The most commonly reported TEAE for lixisenatide-treated patients versus sitagliptin-treated patients was nausea (17.7% versus 6.8%, respectively) followed by headache (12.7% versus 9.3%, respectively). One (0.6%) lixisenatide-treated patient had 2 symptomatic hypoglycemia events as defined in the protocol dining the on-treatment period as compared to 3 (1.9%) patients with 3 events in the sitagliptin group. None of these symptomatic hypoglycemia events was severe according to the protocol definition. A total of 3 patients (2 [1.3%] in the lixisenatide group and 1 [0.6] in the sitagliptin group) reported 3 events adjudicated as allergic reactions by the Allergic Reaction Assessment Committee (ARAC), but only one event (anaphylactic reaction) from a lixisenatide-treated patient was adjudicated as possibly related to the investigational product. No case of pancreatitis was reported in the study.

Objectives

Primary Objective

The primary objective of this study was to assess the efficacy of lixisenatide on a composite endpoint of glycemic control ($HbA_{1c}$) and body weight in comparison to sitagliptin as an add-on treatment to metformin over a period of 24 weeks in obese type 2 diabetic patients younger than 50, and not adequately controlled with metformin alone.

Key Secondary Objecitve(s)

The secondary objectives of this study were:
To assess the effects of lixisenatide on:
Absolute changes in $HbA_{1c}$ values and body weight
Fasting plasma glucose (FPG)
Plasma glucose, insulin, C-peptide, glucagon, and proinsulin dining a 2-hour standardized meal test
Insulin resistance assessed by HOMA-IR.
Beta cell function assessed by HOMA-beta
To assess lixisenatide safety and tolerability
To assess anti-lixisenatide antibody development Trial Design This was a double-blind, double-dummy, randomized, active-controlled, 2-arm parallel-group, multicenter, multinational study planned in 150 lixisenatide treated patients and 150 sitagliptin treated patients. The study was double-blind with regard to treatment group. The study drug volume (ie, dose of active drug or matching placebo) was not blinded.

The patients were stratified by screening values of glycosylated hemoglobin $A_{1c}$ ($HbA_{1c}$) (<8%, ≥8%) and body mass index (BMI) (<35 kg/m$^2$, ≥35 kg/m$^2$). After a screening period, patients were centrally randomized via interactive voice response system (IVRS) in a 1:1 ratio to either lixisenatide or sitagliptin The study consisted of 3 periods: 1) an up to 3-week screening period, which included an up to 2-week screening phase and a 1-week single-blind placebo run-in phase; 2) a 24-week double-blind, double-dummy, active-controlled treatment period; 3) a post-treatment follow-up period of 3 days for all the patients after permanent treatment discontinuation (except for patients who prematurely discontinued the study treatment).

Per the protocol amendment 1 (dated on 30 Tune 2009), patients who prematurely discontinued the study treatment were continued in the study up to the final assessment at Week 24. They were followed up according to the study procedures as specified in the protocol (except meal challenge test and 3-day safety post-treatment follow-up).

Primary and Key Secondary Endpoints

Primary Endpoint

The primary efficacy variable was the percentage of patients with $HbA_{1c}$ <7% at Week 24 AND a weight loss of at least 5% of baseline body weight at Week 24.

If a patient discontinued the treatment prematurely during the 24-week double-blind treatment period or did not have $HbA_{1c}$ or body weight value at Week 24, the last post-baseline on-treatment $HbA_{1c}$ or body weight measurement during the 24-week period was used for the calculation of Week 24 (last observation carried forward [LOCF] procedure) for $HbA_{1c}$ or body weight respectively. If the last post-baseline on-treatment $HbA_{1c}$ and body weight values were measured more than 30 days apart from each other, the last post-baseline on-treatment values ($HbA_{1c}$ and body weight) that were no more than 30 days apart were used for the composite endpoint at Week 24. Patients who did not have post-baseline on-treatment values ($HbA_{1c}$ and body weight) that were no more than 30 days apart during the 24-week period were counted as non-responders for the composite primary endpoint. For all patients rescued during the 24-week period, the last post-baseline on $HbA_{1c}$ and bodyweight measurements before the rescue were used as the $HbA_{1c}$ and body weight at Week 24.

Key Secondary Endpoints

Efficacy Endpoints

For secondary efficacy variables, the same procedure for handling missing assessments/early discontinuation was applied as for the primary efficacy variable. That is, the LOCF procedure was used by taking the last available post-baseline on-treatment measurement (before the rescue medication in the event of rescue therapy) as the Week 24 value.

Continuous Variables

Absolute change in $HbA_{1c}$ (%) from baseline to Week 24
Absolute change in body weight (kg) from baseline to Week 24
Change in 2-hour postprandial plasma glucose (mmol/L) after a standardized meal test from baseline to Week 24
Change in FPG (mmol/L) from baseline to Week 24
Change in glucose excursion (2-hour postprandial plasma glucose-plasma glucose 30 minutes prior to the meal test before study drug administration) (mmol/L) during a standardized meal challenge test from baseline to Week 24
Change in the following variables under fasting (30 minutes prior to the meal test before study drug administration) and 2-hour postprandial conditions collected during a standardized meal test: insulin (pmol/L), C-peptide (nmol/L), glucagon (ng/L), proinsulin (pmol/L), and proinsulin-to-insulin ratio from baseline to Week 24
Change in insulin resistance assessed by HOMA-IR from baseline to Week 24
Change in beta-cell function assessed by HOMA-beta from baseline to Week 24

Categorical Variables

Percentage of patients with $HbA_{1c}$<7% at Week 24
Percentage of patients with $HbA_{1c}$≤6.5% at Week 24
Percentage of patients requiring rescue therapy during the double-blind treatment period
Percentage of patients with ≥5% weight loss (kg) from baseline to Week 24

Safety Endpoints

The safety analysis was based on the reported TEAEs and other safety information including symptomatic hypoglycemia and severe symptomatic hypoglycemia, local tolerability at injection site, allergic events (as adjudicated by ARAC), suspected pancreatitis, increased calcitonin, vital signs, 12-lead ECG and laboratory tests.

Major cardiovascular events were also collected and adjudicated by a Cardiovascular events Adjudication Committee (CAC). The adjudicated and confirmed events by CAC from this study (if any), and other lixisenatide phase 3 studies, will be pooled for analyses and summarized in a separate report based on the statistical analysis plan for the overall cardiovascular assessment of lixisenatide. The Key Results Memo (KRM)/Clinical Study Report (CSR) will not present the summary of the adjudicated and confirmed cardiovascular events from this study.

Sample Size Calculation Assumptions

The sample size calculation was based on the primary efficacy endpoint percentage of patients with $HbA_{1c}$ <7% at Week 24 AND a weight loss of at least 5% of baseline body Weight at Week 24. This calculation assumed the percentage of patients defined as responders on $HbA_{1c}$ (<7%) and weight (at least 5% loss) was 25% with lixisenatide and 10% with sitagliptin with a 2-sided test at the 5% significance level.

A sample size of 300 patients (150 patients per group) was considered sufficient to demonstrate the superiority of lixisenatide over sitagliptin in the percentage of patients defined as responders on $HbA_{1c}$ (<7%) and weight (at least 5% loss) at Week 24, with a power of 90%.

Statistical Methods
Analysis Populations

The modified intent-to-treat (mITT) population consisted of all randomized patients who received at least one dose of double-blind investigational product (IP). Patients were analyzed in the treatment group to which they were randomized.

The safety population was defined as all randomised patients who took at least one dose of the double-blind IP.

Primary Efficacy Analysis

The primary efficacy variable (percentage of patients with $HbA_{1c}$<7% at Week 24 AND a weight loss of at least 5% of baseline body weight at Week 24) was analyzed using Cochran Mantel-Haenszel (CMH) test stratified by randomization strata of screening $HbA_{1c}$ (<8%, ≥8%) and randomization stratified of screening BMI (<35 kg/m², ≥35 kg/m²). The p-value was based on CMH test from PROC FREQ. The point estimate of the treatment difference (lixisenatide compared to sitagliptin) in proportion as well as the associated 95% confidence interval (CI) were provided based on the weighted average of treatment differences from each strait using CMH weights.

In case of no event in a cell for a staata, continuity correction was made (ie, 0.5 was added to each cell of the 2×2 table) for that strata for variance calculation only. Note that no continuity adjustment was applied for estimating the weighted average of treatment difference. The continuity correction was applied to estimate variance for constructing 95% CI for the overall difference.

The primary analysis of the primary efficacy variable was performed based on the mITT population and the measurements obtained during the on-treatment period for efficacy variables. The on-treatment period for efficacy variables except those from the meal challenge test was defined as the time from the first dose of the double-blind IP (lixisenatide or sitagliptin) up to 3 days (except for PPG by central laboratory, which was up to 1 day) after the last dose of the double-blind IP, or up to the introduction of the rescue therapy, whichever was the earliest. The on-treatment period for efficacy variables from the meal challenge test including 2-hour postprandial plasma glucose, insulin, C-peptide, glucagon, proinsulin, glucose excursion, HOMA indexes, and proinsulin-to-insulin ratio was defined as the time from the first dose of the double-blind IP (lixisenatide or sitagliptin) up to the date of the last dose of the double-blind IP, or up to the introduction of the rescue therapy, whichever was the earliest.

The LOCF procedure was used by taking the last available post-baseline on-treatment values ($HbA_{1c}$ and body weight before the introduction of rescue therapy) that were no more than 30 days apart from each other as the composite endpoint at Week 24. Patients who did not have such values were counted as non-responders for the composite primary endpoint.

Key Secondary Efficacy Analysis

No multiplicity adjustment was made on any secondary efficacy variable.

All continuous secondary efficacy variables as described in Section 32.1 were analyzed by an analysis of covariance (ANCOVA) model with treatment groups (lixisenatide and sitagliptin), randomization strata of screening $HbA_{1c}$ (<8.0, ≥8.0%), randomization strata of screening BMI (<35 kg/m², ≥35 kg/m²), and country as fixed effects and using the corresponding baseline value as a covariate. The adjusted estimates of the treatment mean difference between lixisenatide and sitagliptin and two-sided 95% confidence intervals were provided.

For the following categorical secondary efficacy variables, the summary statistics were presented by treatment group:
  Percentage of patients with $HbA_{1c}$<7% at Week 24,
  Percentage of patients with $HbA_{1c}$≤6.5% at Week 24,
  Percentage of patients requiring rescue therapy during the 24-week treatment period,
  Percentage of patients with ≥5% weight loss (kg) from baseline at Week 24.

Safety Analysis

The safety analyses were primarily based on the on-treatment period. The on-treatment period was defined as the time from the first dose of double-blind IP (lixisenatide or sitagliptin) up to 3 days after the last dose of IP administration regardless of rescue status. The 3-day interval was chosen based on the half-life of the IP (approximately 5 times the half-life).

The summary of safety results (descriptive statistics or frequency tables) is presented by treatment groups.

Results
Study Patients
Patient Accountability

The study was conducted in 92 centers in 13 countries (Australia, Brazil, Canada, Chile, Germany, Guatemala, Mexico, Peru, Poland, Romania, Russian Federation, Ukraine and United States of America). A total of 620 patents were screened, out of which 319 were randomized to one of the two treatment groups. The most common reason for non-randomization was $HbA_{1c}$ valve out of range at the screening visit as defined per protocol (203 [323%] out of 620 screened patients).

All 319 randomized patients were exposed to the study treatment and were included in mITT population. Table 29 provides the number of patients included in each analysis population

TABLE 29

| Analysis populations - Randomized population | | | |
|---|---|---|---|
| | Lixisenatide | Sitagliptin | All |
| Randomized population | 158 (100%) | 161 (100%) | 319 (100%) |
| Efficacy population Modified Intent-to-Treat (mITT) | 158 (100%) | 161 (100%) | 319 (100%) |
| Safety population | 158 (100%) | 161 (100%) | 319 (100%) |

Note:
The safety population patients are tabulated according to treatment actually received (as treated).
For the efficacy population, patients are tabulated according to their randomized treatment (as randomized).

Study Disposition

Table 30 provides the summary of patient disposition for each treatment group. Of the 319 randomized patients, 27 (8.5%) patients prematurely discontinued the study treatment with a higher percentage in the lixisenatide group (16 patients: 10.1%) compared to the sitagliptin group (11 patients: 6.8%). For the lixisenatide group, the main reason for treatment discontinuation was "other reasons" (7 patients: 4.4% versus 5 patients: 3.1% for sitagliptin) followed by "adverse events" (4 patients: 2.5% versus 5 patients: 3.1% for sitagliptin). The time-to-onset of treatment discontinuation due to any reason is depicted in FIG. 11. A higher rate of treatment discontinuation was observed in the lixisenatide group throughout the study.

TABLE 30

Patient disposition - Randomized population

|  | Lixisenatide (N = 158) | Sitagliptin (N = 161) |
|---|---|---|
| Randomized and treated | 158 (100%) | 161 (100%) |
| Did not complete double-blind study treatment | 16 (10.1%) | 11 (6.8%) |
| Subject's request for treatment discontinuation | 14 (8.9%) | 8 (5.0%) |
| Reason for study treatment discontinuation | 16 (10.1%) | 11 (6.8%) |
| Adverse event | 4 (2.5%) | 5 (3.1%) |
| Lack of efficacy | 0 | 0 |
| Poor compliance to protocol | 3 (1.9%) | 0 |
| Lost to follow-up | 2 (1.3%) | 1 (0.6%) |
| Other reasons | 7 (4.4%) | 5 (3.1%) |
| Status at last study contact | 158 (100%) | 161 (100%) |
| Alive | 158 (100%) | 161 (100%) |
| Dead | 0 | 0 |
| Lost to follow-up | 0 | 0 |

Note:
Percentages are calculated using the number of randomized patients as denominator.

Demographics and Baseline Characteristics

The demographic and patient baseline characteristics were generally similar between the two treatment groups for the safety population (Table 31), with however more female patients in the lixisenatide group (103 [65.2%]) compared with the sitagliptin group (88 [54.7%]). The median age was 44.0 years. The study population was primarily Caucasian (81.2%).

TABLE 31

Demographics and patient characteristics at screening or baseline - Safety population

|  | Lixisenatide (N = 158) | Sitagliptin (N = 161) | All (N = 319) |
|---|---|---|---|
| Age (years) | | | |
| Number | 158 | 161 | 319 |
| Mean (SD) | 42.7 (5.2) | 43.4 (4.7) | 43.1 (4.9) |
| Median | 44.0 | 44.0 | 44.0 |
| Min:Max | 22:49 | 32:49 | 22:49 |
| Gender [n (%)] | | | |
| Number | 158 | 161 | 319 |
| Male | 55 (34.8%) | 73 (45.3%) | 128 (40.1%) |
| Female | 103 (65.2%) | 88 (54.7%) | 191 (59.9%) |
| Race [n (%)] | | | |
| Number | 158 | 161 | 319 |
| Caucasian/White | 132 (83.5%) | 127 (78.9%) | 259 (81.2%) |
| Black | 8 (5.1%) | 11 (6.8%) | 19 (6.0%) |
| Asian/Oriental | 1 (0.6%) | 1 (0.6%) | 2 (0.6%) |
| Other | 17 (10.8%) | 22 (13.7%) | 39 (12.2%) |

TABLE 31-continued

Demographics and patient characteristics at screening or baseline - Safety population

|  | Lixisenatide (N = 158) | Sitagliptin (N = 161) | All (N = 319) |
|---|---|---|---|
| Ethnicity [n (%)] | | | |
| Number | 158 | 161 | 319 |
| Hispanic | 73 (46.2%) | 72 (44.7%) | 145 (45.5%) |
| Non Hispanic | 85 (53.8%) | 89 (55.3%) | 174 (54.5%) |
| Screening HbA1c (%) | | | |
| Number | 158 | 161 | 319 |
| Mean (SD) | 8.28 (0.87) | 8.25 (0.83) | 8.27 (0.85) |
| Median | 8.10 | 8.20 | 8.20 |
| Min:Max | 7.0:10.1 | 7.0:10.0 | 7.0:10.1 |
| Randomization strata of screening HbA1c (%) [n (%)] | | | |
| Number | 158 | 161 | 319 |
| <8 | 65 (41.1%) | 66 (41.0%) | 131 (41.1%) |
| ≥8 | 93 (58.9%) | 95 (59.0%) | 188 (58.9%) |
| Screening BMI (kg/m$^2$) | | | |
| Number | 158 | 161 | 319 |
| Mean (SD) | 36.88 (7.25) | 36.83 (6.32) | 36.86 (6.78) |
| Median | 34.72 | 34.85 | 34.75 |
| Min:Max | 29.7:70.0 | 30.0:60.8 | 29.7:70.0 |
| Randomization strata of screening BMI (kg/m$^2$) [n (%)] | | | |
| Number | 158 | 161 | 319 |
| <35 | 80 (50.6%) | 82 (50.9%) | 162 (50.8%) |
| ≥35 | 78 (49.4%) | 79 (49.1%) | 157 (49.2%) |
| Baseline BMI (kg/m$^2$) | | | |
| Number | 158 | 161 | 319 |
| Mean (SD) | 36.76 (7.25) | 36.76 (6.34) | 36.76 (6.80) |
| Median | 34.33 | 34.88 | 34.68 |
| Min:Max | 28.8:69.4 | 29.7:59.0 | 28.8:69.4 |
| Baseline BMI Categories (kg/m$^2$) [n (%)] | | | |
| Number | 158 | 161 | 319 |
| <35 | 83 (52.5%) | 83 (51.6%) | 166 (52.0%) |
| ≥35 | 75 (47.5%) | 78 (48.4%) | 153 (48.0%) |

BMI = Body Mass Index.

Disease characteristics including diabetic history are described in Table 32. In the study population, the median duration of diabetes was 3.31 years, and the median age at onset of diabetes was 40 years, with similar numbers in both treatment groups. Numbers were slightly different for the following: higher median daily dose of metformin at baseline in the lixisenatide group (2000 mg versus 1700 mg for sitagliptin), more females with a history of gestational diabetes (12.6% versus 6.8% for sitagliptin) and more patients with macroalbuminuria at randomization (4.6% versus 1.9% for sitagliptin), but less patients with diabetic sensory or motor neuropathy in the lixisenatide group (12.2% versus 17.5% for sitagliptin) and less patients with microalbuminuria at randomization (17.8% versus 26.4% for sitagliptin).

TABLE 32

Disease characteristics at screening or baseline - Safety population

| | Lixisenatide (N = 158) | Sitagliptin (N = 161) | All (N = 319) |
|---|---|---|---|
| Duration of diabetes (years) | | | |
| Number | 158 | 161 | 319 |
| Mean (SD) | 4.40 (3.86) | 4.43 (3.56) | 4.42 (3.70) |
| Median | 3.19 | 3.38 | 3.31 |
| Min:Max | 1.0:29.6 | 1.0:19.6 | 1.0:29.6 |
| Age at onset of type 2 diabetes (years) | | | |
| Number | 158 | 161 | 319 |
| Mean (SD) | 38.4 (6.0) | 39.0 (5.6) | 38.7 (5.8) |
| Median | 40.0 | 40.0 | 40.0 |
| Min:Max | 19:48 | 22:48 | 19:48 |
| Duration of metformin treatment (years) | | | |
| Number | 158 | 161 | 319 |
| Mean (SD) | 3.04 (3.19) | 2.75 (2.39) | 2.89 (2.81) |
| Median | 2.10 | 1.82 | 2.05 |
| Min:Max | 0.3:20.0 | 0.3:12.0 | 0.3:20.0 |
| Daily dose of metformin at baseline (mg) | | | |
| Number | 158 | 161 | 319 |
| Mean (SD) | 1984.7 (413.5) | 1937.0 (405.0) | 1960.6 (409.3) |
| Median | 2000.0 | 1700.0 | 1700.0 |
| Min:Max | 1500:3000 | 1500:3000 | 1500:3000 |
| Categorized daily dose of metformin at baseline (mg) [n (%)] | | | |
| Number | 158 | 161 | 319 |
| <1500 | 0 | 0 | 0 |
| ≥1500-<2500 | 120 (75.9%) | 124 (77.0%) | 244 (76.5%) |
| ≥2500-<3000 | 30 (19.0%) | 33 (20.5%) | 63 (19.7%) |
| ≥3000 | 8 (5.1%) | 4 (2.5%) | 12 (3.8%) |
| History of gestational diabetes [n (%)] | | | |
| Number (Female) | 103 | 88 | 191 |
| Yes (Female) | 13 (12.6%) | 6 (6.8%) | 19 (9.9%) |
| No (Female) | 90 (87.4%) | 82 (93.2%) | 172 (90.1%) |
| Prior use of GLP-1 receptor agonist [n (%)] | | | |
| Number | 158 | 161 | 319 |
| Yes | 1 (0.6%) | 0 | 1 (0.3%) |
| No | 157 (99.4%) | 161 (100%) | 318 (99.7%) |
| Diabetic retinopathy [n (%)] | | | |
| Number | 156 | 160 | 316 |
| Yes | 4 (2.6%) | 6 (3.8%) | 10 (3.2%) |
| No | 142 (91.0%) | 145 (90.6%) | 287 (90.8%) |
| Unknown | 10 (6.4%) | 9 (5.6%) | 19 (6.0%) |
| Diabetic sensory or motor neuropathy [n (%)] | | | |
| Number | 156 | 160 | 316 |
| Yes | 19 (12.2%) | 28 (17.5%) | 47 (14.9%) |
| No | 134 (85.9%) | 131 (81.9%) | 265 (83.9%) |
| Unknown | 3 (1.9%) | 1 (0.6%) | 4 (1.3%) |
| Diabetic autonomic neuropathy [n (%)] | | | |
| Number | 156 | 160 | 316 |
| Yes | 1 (0.6%) | 1 (0.6%) | 2 (0.6%) |
| No | 150 (96.2%) | 157 (98.1%) | 307 (97.2%) |
| Unknown | 5 (3.2%) | 2 (1.3%) | 7 (2.2%) |
| Diabetic nephropathy [n (%)] | | | |
| Number | 156 | 160 | 316 |
| Yes | 4 (2.6%) | 5 (3.1%) | 9 (2.8%) |
| Microalbuminuria | 4 (2.6%) | 5 (3.1%) | 9 (2.8%) |
| Overt proteinuria | 0 | 0 | 0 |
| Impaired renal function | 0 | 0 | 0 |
| Dialysis or transplantation | 0 | 0 | 0 |
| No | 145 (92.9%) | 149 (93.1%) | 294 (93.0%) |
| Unknown | 7 (4.5%) | 6 (3.8%) | 13 (4.1%) |
| Categorized albumin/creatinine ratio at randomization [n (%)] | | | |
| Number | 152 | 159 | 311 |
| <30 μg/mg creatinine (normal) | 118 (77.6%) | 114 (71.7%) | 232 (74.6%) |
| ≥30-<300 μg/mg creatinine (microalbuminuria) | 27 (17.8%) | 42 (26.4%) | 69 (22.2%) |
| ≥300 μg/mg creatinine (macroalbuminuria) | 7 (4.6%) | 3 (1.9%) | 10 (3.2%) |
| Creatinine clearance (ml/min) at screening | | | |
| Number | 158 | 160 | 318 |
| Mean (SD) | 163.80 (51.85) | 163.66 (43.83) | 163.73 (47.91) |
| Median | 158.26 | 155.92 | 156.52 |
| Min:Max | 74.8:463.9 | 86.3:298.2 | 74.8:463.9 |
| Creatinine clearance categories at screening [n (%)] | | | |
| Number | 158 | 160 | 318 |
| <30 ml/min (severe renal impairment) | 0 | 0 | 0 |
| ≥30-<50 ml/min (moderate renal impairment) | 0 | 0 | 0 |
| ≥50-≤80 ml/min (mild renal impairment) | 2 (1.3%) | 0 | 2 (0.6%) |
| >80 ml/min (no renal impairment) | 156 (98.7%) | 160 (100%) | 316 (99.4%) |

GLP-1 = Glucagon like peptide-1.
Creatinine clearance value is derived using the equation of Cockcroft and Gault.
Albumin/creatinine ratio is presented in μg/mg creatinine, equivalent to mg/g creatinine, and the conversion factor to the standard international unit mg/mmol creatinine is 0.1130.

$HbA_{1c}$, 2-hour PPG, and FPG were comparable between the two treatment groups for the safety population (Table 33). The average $HbA_{1c}$ at baseline was 8.12%. A lower mean body weight at baseline was observed in the lixisenatide group (98.51 kg) compared with the sitagliptin group (100.56 kg), but mean baseline BMI was the same for the two treatment groups (36.76 kg/m$^2$) as shown in Table 31.

TABLE 33

Baseline efficacy variables - Safety population

|  | Lixisenatide (N = 158) | Sitagliptin (N = 161) | All (N = 319) |
|---|---|---|---|
| HbA1c (%) | | | |
| Number | 158 | 161 | 319 |
| Mean (SD) | 8.16 (0.89) | 8.09 (0.96) | 8.12 (0.93) |
| Median | 8.10 | 8.00 | 8.00 |
| Min:Max | 6.4:10.1 | 5.0:11.0 | 5.0:11.0 |
| Weight (kg) | | | |
| Number | 158 | 161 | 319 |
| Mean (SD) | 98.51 (23.48) | 100.56 (23.77) | 99.55 (23.61) |
| Median | 94.50 | 97.30 | 97.00 |
| Min:Max | 54.4:180.6 | 59.3:180.8 | 54.4:180.8 |
| FPG (mmol/L) | | | |
| Number | 158 | 161 | 319 |
| Mean (SD) | 9.09 (2.60) | 8.96 (2.59) | 9.03 (2.59) |
| Median | 8.71 | 8.82 | 8.72 |
| Min:Max | 4.7:19.1 | 4.6:17.7 | 4.6:19.1 |
| **2-hour postprandial plasma glucose* (mmol/L)** | | | |
| Number | 158 | 157 | 315 |
| Mean (SD) | 13.77 (3.78) | 13.92 (3.99) | 13.84 (3.88) |
| Median | 13.76 | 14.21 | 13.82 |
| Min:Max | 4.4:23.9 | 3.9:23.9 | 3.9:23.9 |
| **Glucose excursion* (mmol/L)** | | | |
| Number | 157 | 157 | 314 |
| Mean (SD) | 4.37 (2.64) | 4.48 (2.59) | 4.42 (2.61) |
| Median | 4.38 | 4.33 | 4.36 |
| Min:Max | −4.6:10.2 | −3.7:12.2 | −4.6:12.2 |
| HOMA-IR* | | | |
| Number | 148 | 154 | 302 |
| Mean (SD) | 6.30 (5.08) | 6.26 (5.32) | 6.28 (5.20) |
| Median | 5.35 | 4.95 | 5.21 |
| Min:Max | 0.4:34.1 | 0.4:29.4 | 0.4:34.1 |
| HOMA-β | | | |
| Number | 148 | 154 | 302 |
| Mean (SD) | 62.01 (59.78) | 60.74 (50.80) | 61.36 (55.29) |
| Median | 44.41 | 47.25 | 44.76 |
| Min:Max | 5.2:398.2 | 3.0:272.9 | 3.0:398.2 |

*From the meal challenge test
FPG = Fasting plasma glucose.
Glucose excursion = 2-hour postprandial plasma glucose − plasma glucose 30 minutes prior to the meal test before study drug administration.

Dosage and Duration

The average treatment exposure was slightly shorter for the lixisenatide group compared with the sitagliptin group: 160.2 days (22.9 weeks) exposure to lixisenatide for the lixisenatide group (Table 34) and 164.8 days (23.5 weeks) exposure to sitagliptin for the sitagliptin group (Table 35). The vast majority of patients in both treatment groups had at least 85 days of treatment (90.5% and 96.3% in the lixisenatide and sitagliptin groups respectively). Five patients (4 for lixisenatide and 1 for sitagliptin) did not record the last administration date on the CRF pages "End of treatment" and "Investigational product administration", hence their durations of exposure were set to missing following the SAP data handling convention.

At the end of double-blind treatment, the proportion of patients who reached the target lixisenatide daily dose (active drug or volume-matched placebo) of 20 μg was lower in lixisenatide group (94.9%) compared with the sitagliptin group (100%) (Table 36).

TABLE 34

Exposure to lixisenatide (or lixisenatide placebo) - Safety population

|  | Lixisenatide (N = 158) | Sitagliptin (N = 161) |
|---|---|---|
| Cumulative duration of lixisenatide (or lixisenatide placebo) exposure (patient years) | 67.5 | 72.2 |
| Duration of lixisenatide (or lixisenatide placebo) treatment (days) | | |
| Number | 154 | 160 |
| Mean (SD) | 160.2 (36.9) | 164.7 (23.9) |
| Median | 169.0 | 169.0 |
| Min:Max | 1:190 | 31:188 |
| Duration of lixisenatide (or lixisenatide placebo) treatment by category [n (%)] | | |
| Missing duration | 4 (2.5%) | 1 (0.6%) |
| 1-14 days | 4 (2.5%) | 0 |
| 15-28 days | 3 (1.9%) | 0 |
| 29-56 days | 2 (1.3%) | 3 (1.9%) |
| 57-84 days | 2 (1.3%) | 2 (1.2%) |
| 85-168 days | 32 (20.3%) | 40 (24.8%) |
| >168 days | 111 (70.3%) | 115 (71.4%) |
| Cumulative duration of lixisenatide (or lixisenatide placebo) treatment by category [n (%)] | | |
| Missing duration | 4 (2.5%) | 1 (0.6%) |
| ≥1 days | 154 (97.5%) | 160 (99.4%) |
| ≥15 days | 150 (94.9%) | 160 (99.4%) |
| ≥29 days | 147 (93.0%) | 160 (99.4%) |
| ≥57 days | 145 (91.8%) | 157 (97.5%) |
| ≥85 days | 143 (90.5%) | 155 (96.3%) |
| ≥169 days | 111 (70.3%) | 115 (71.4%) |

Duration of lixisenatide (or lixisenatide placebo) exposure = (date of the last double-blind lixisenatide injection − date of the first double-blind lixisenatide injection) + 1.

TABLE 35

Exposure to sitagliptin (or sitagliptin placebo) - Safety population

|  | Lixisenatide (N = 158) | Sitagliptin (N = 161) |
|---|---|---|
| Cumulative duration of sitagliptin (or sitagliptin placebo) exposure (patient years) | 67.6 | 72.2 |
| Duration of sitagliptin (or sitagliptin placebo) treatment (days) | | |
| Number | 154 | 160 |
| Mean (SD) | 160.3 (36.8) | 164.8 (23.6) |
| Median | 169.0 | 169.0 |
| Min:Max | 1:189 | 31:188 |
| Duration of sitagliptin (or sitagliptin placebo) treatment by category [n (%)] | | |
| Missing duration | 4 (2.5%) | 1 (0.6%) |
| 1-14 days | 4 (2.5%) | 0 |
| 15-28 days | 3 (1.9%) | 0 |
| 29-56 days | 2 (1.3%) | 3 (1.9%) |
| 57-84 days | 2 (1.3%) | 2 (1.2%) |
| 85-168 days | 33 (20.9%) | 39 (24.2%) |
| >168 days | 110 (69.6%) | 116 (72.0%) |

TABLE 35-continued

Exposure to sitagliptin (or sitagliptin placebo) - Safety population

|  | Lixisenatide (N = 158) | Sitagliptin (N = 161) |
|---|---|---|
| Cumulative duration of sitagliptin (or sitagliptin placebo) treatment by category [n (%)] | | |
| Missing duration | 4 (2.5%) | 1 (0.6%) |
| ≥1 days | 154 (97.5%) | 160 (99.4%) |
| ≥15 days | 150 (94.9%) | 160 (99.4%) |
| ≥29 days | 147 (93.0%) | 160 (99.4%) |
| ≥57 days | 145 (91.8%) | 157 (97.5%) |
| ≥85 days | 143 (90.5%) | 155 (96.3%) |
| ≥169 days | 110 (69.6%) | 116 (72.0%) |

Duration of sitagliptin (or sitagliptin placebo) exposure = (date of the last double-blind sitagliptin administration − date of the first double-blind sitagliptin administration) + 1.

TABLE 36

Number (%) of patients by final lixisenatide dose at the end of the double-blind treatment - Safety population

| Final Lixisenatide dose | Lixisenatide (N = 158) | Sitagliptin (N = 161) |
|---|---|---|
| 10 μg | 6 (3.8%) | 0 |
| 15 μg | 2 (1.3%) | 0 |
| 20 μg | 150 (94.9%) | 161 (100%) |

Dose = Dose of active drug or volume-matched placebo.
Note:
Percentages are calculated using the number of safety patients as the denominator.

Efficacy

Primary Efficacy Endpoint

Main Analysis

Table 37 summarizes the results of the primary efficacy variable, the percentage of patients with $HbA_{1c}$ <7% at Week 24 and a weight loss of at least 5% of baseline body weight at Week 24 using a CMH method.

The pre-specified primary analysis based on the CMH method did not show a statistically significant difference between the 2 treatment groups in the percentage of patients with $HbA_{1c}$ <7% at Week 24 and a weight loss of at least 5% of baseline body weight at Week 24 (weighted average of response rate difference vs. sitagliptin=4.6%; p-value=0.1696). The percentage of patients who met the criteria (response rate) was numerically higher in the lixisenatide group (12.0%) than the sitagliptin group (7.5%).

TABLE 37

Number (%) of patients with HbA1c <7% at Week 24 and weight loss of ≥5% of baseline body weight at Week 24 - mITT population

|  | Lixisenatide (N = 158) | Sitagliptin (N = 161) |
|---|---|---|
| Number | 158 | 161 |
| Response rate | 19 (12.0%) | 12 (7.5%) |
| Response rate difference (SE) vs. sitagliptin[a] | 4.6% (3.28%) | — |

TABLE 37-continued

Number (%) of patients with HbA1c <7% at Week 24 and weight loss of ≥5% of baseline body weight at Week 24 - mITT population

|  | Lixisenatide (N = 158) | Sitagliptin (N = 161) |
|---|---|---|
| 95% CI[a] | (−1.84% to 11.00%) | — |
| CMH p-value[b] | 0.1696 | — |

[a]Weighted average of response rate difference between treatment groups (lixisenatide and sitagliptin) from each strata (randomization strata of screening HbA1c [<8.0, ≥8.0%], randomization strata of screening BMI [<35 or ≥35 kg/m$^2$]) using Cochran-Mantel-Haenszel (CMH) weights.
[b]Based on CMH method stratified by randomization strata of screening HbA1c (<8.0 or ≥8.0%) and randomization strata of screening BMI (<35 or ≥35 kg/m$^2$).
Note:
The analysis excluded measurements obtained after the introduction of rescue medication and/or after the treatment cessation plus 3 days.
Patients who do not have post-baseline on-treatment values (HbA1c and body weight) that are no more than 30 days apart are counted as non-responders.

Supportive Analysis

A supportive analysis using a logistic regression model showed a consistent result with the finding from the primary analysis for the primary efficacy endpoint (p-value=0.1160) (Table 38).

TABLE 38

Number (%) of patients with HbA1c <7% at Week 24 and weight loss of ≥5% of baseline body weight at Week 24 - mITT population

|  | Lixisenatide (N = 158) | Sitagliptin (N = 161) |
|---|---|---|
| Number | 158 | 161 |
| Response rate | 19 (12.0%) | 12 (7.5%) |
| Odds ratio (95% CI) vs. sitagliptin[a] | 1.88 (0.86 to 4.12) | — |
| p-value | 0.1160 | — |

[a]Logistic regression model with treatment groups, randomization strata of screening HbA1c (<8, ≥8%), and randomization strata of screening BMI (<35 kg/m$^2$, ≥35 kg/m$^2$) as fixed effects and baseline HbA1c and baseline body weight values as covariates.
Note:
The analysis excluded measurements obtained after the introduction of rescue medication and/or after the treatment cessation plus 3 days.
Patients who do not have post-baseline on-treatment values (HbA1c and body weight) that are no more than 30 days apart are counted as non-responders.

Other Key Efficacy Endpoints

The ANCOVA analyses of $HbA_{1c}$, body weight, 2-hour PPG, FPG, glucose excursion, HOMA-IR and HOMA-β are presented in this section. FIG. 13, FIG. 15 and FIG. 16, illustrate the Mean (±SE) change from baseline in $HbA_{1c}$, body weight and FPG over time during the 24-week double-blind treatment period. FIG. 14 illustrates the $HbA_{1c}$ responders (≤6.5% or <7% respectively) at selected visits. The percentage of patients who were rescued during the double-blind treatment period is presented in Table 48.

For $HbA_{1c}$, the LS mean changes from baseline to Week 24 were −0.66% for the lixisenatide group and −0.72% for the sitagliptin group, with no significant difference between treatment groups (LS mean difference vs. sitagliptin=0.06%, 95% CI [−0.179; 0.308]) (Table 39).

$HbA_{1c}$ reached a plateau after week 12 for both treatment groups (FIG. 13). A total of 61 patients (40.7%) in the lixisenatide group had $HbA_{1c}$<7% at Week 24 compared to 64 patients (40.0%) in the sitagliptin group, and 36 (24.0%) of lixisenatide-treated patients had $HbA_{1c}$ ≤6.5% compared to 42 (26.3%) of sitagliptin-treated patients (Table 40).

Treatment with lixisenatide resulted in a significant decrease in body weight (LS mean difference versus sitagliptin=−1.34 kg, 95% CI [−2.101; −0.575]) (Table 41). Body weight reached a plateau after week 16 for the sitagliptin-treated patients while it continuously decreased for the lixisenatide-treated patients (FIG. 15). More lixisenatide-treated patients (28 [18.4%]) had ≥5% weight loss from baseline to Week 24 than sitagliptin-treated patients (19 [11.9%]) (Table 42).

The results of the 2-hour PPG assessment showed a significant improvement from baseline to Week 24 in the lixisenatide group compared with the sitagliptin group (LS mean difference versus sitagliptin=−1.91 mmol/L, 95% CI [−2.876; −0.941]) (Table 43).

The LS mean changes from baseline to Week 24 in FPG were −0.45 mmol/L for the lixisenatide group and −0.69 mmol/L for the sitagliptin group, with no significant difference between treatment groups (LS mean difference vs. sitagliptin=0.25 mmol/L, 95% CI [−0.254; 0.744]) (Table 44).

Treatment with lixisenatide significantly decreased glucose excursion from baseline to Week 24 compared with the sitagliptin group (LS mean difference vs. sitagliptin=−2.13 mmol/L, 95% CI [−2.819; −1.434]) (Table 45).

For insulin resistance assessed by HOMA-IR, the LS mean change from baseline to Week 24 was −0.52 in the lixisenatide group and −0.57 in the sitagliptin group, with no significant difference between treatment groups (LS mean difference versus sitagliptin=0.05, 95% CI [−0.823; 0.918]) (Table 46).

For β-cell function assessed by HOMA-β, the LS mean change from baseline to Week 24 was 17.66 in the lixisenatide group and 17.79 in the sitagliptin group, with no significant difference between treatment groups (LS mean difference versus sitagliptin=−0.13, 95% CI [−23.108; 22.842]) (Table 47).

The percentages of patients requiring rescue therapy were 9.5% in the lixisenatide group and 6.8% in the sitagliptin group, with no significant difference between these two groups. (Table 48).

TABLE 39

Mean change in HbA1c (%) from baseline to Week 24 - mITT population

| HbA1c (%) | Lixisenatide (N = 158) | Sitagliptin (N = 161) |
|---|---|---|
| Baseline | | |
| Number | 150 | 160 |
| Mean (SD) | 8.17 (0.89) | 8.08 (0.97) |
| Median | 8.10 | 8.00 |
| Min:Max | 6.4:10.1 | 5.0:11.0 |
| Week 24 (LOCF) | | |
| Number | 150 | 160 |
| Mean (SD) | 7.52 (1.26) | 7.38 (1.26) |
| Median | 7.40 | 7.30 |
| Min:Max | 4.8:12.9 | 5.3:11.9 |
| Change from baseline to week 24 (LOCF) | | |
| Number | 150 | 160 |
| Mean (SD) | −0.65 (1.15) | −0.70 (1.08) |
| Median | −0.70 | −0.70 |
| Min:Max | −4.0:4.4 | −3.6:3.7 |
| LS Mean (SE)[a] | −0.66 (0.094) | −0.72 (0.097) |

TABLE 39-continued

Mean change in HbA1c (%) from baseline to Week 24 - mITT population

| HbA1c (%) | Lixisenatide (N = 158) | Sitagliptin (N = 161) |
|---|---|---|
| LS Mean difference (SE) vs. Sitagliptin[a] | 0.06 (0.124) | — |
| 95% CI | (−0.179 to 0.308) | — |

LOCF = Last observation carried forward.
[a]Analysis of covariance (ANCOVA) model with treatment groups (lixisenatide and sitagliptin), randomization strata of screening HbA1c (<8.0, ≥8.0%), randomization strata of screening BMI (<35, ≥35 kg/m$^2$), and country as fixed effects and baseline HbA1c value as a covariate.
Note:
The analysis excluded measurements obtained after the introduction of rescue medication and/or after the treatment cessation plus 3 days.
Patients with both baseline and Week 24 (LOCF) measurements are included.

TABLE 40

Number (%) of patients with HbA1c value ≤6.5% or <7% respectively at Week 24 - mITT population

| HbA1c (%) | Lixisenatide (N = 158) | Sitagliptin (N = 161) |
|---|---|---|
| Number | 150 | 160 |
| ≤6.5% | 36 (24.0%) | 42 (26.3%) |
| Number | 150 | 160 |
| <7.0% | 61 (40.7%) | 64 (40.0%) |

Note:
The analysis excluded measurements obtained after the introduction of rescue medication and/or after the treatment cessation plus 3 days.

TABLE 41

Mean change in body weight (kg) from baseline to Week 24 - mITT population

| Body weight (kg) | Lixisenatide (N = 158) | Sitagliptin (N = 161) |
|---|---|---|
| Baseline | | |
| Number | 152 | 160 |
| Mean (SD) | 98.73 (23.89) | 100.33 (23.65) |
| Median | 94.65 | 97.15 |
| Min:Max | 54.4:180.6 | 59.3:180.8 |
| Week 24 (LOCF) | | |
| Number | 152 | 160 |
| Mean (SD) | 96.50 (23.61) | 99.43 (24.00) |
| Median | 92.25 | 97.35 |
| Min:Max | 53.4:174.3 | 57.8:183.0 |
| Change from baseline to week 24 (LOCF) | | |
| Number | 152 | 160 |
| Mean (SD) | −2.24 (3.46) | −0.89 (3.37) |
| Median | −1.60 | −0.50 |
| Min:Max | −17.0:5.6 | −11.0:8.5 |
| LS Mean (SE)[a] | −2.51 (0.294) | −1.17 (0.304) |
| LS Mean difference (SE) vs. Sitagliptin[a] | −1.34 (0.388) | — |
| 95% CI | (−2.101 to −0.575) | — |

LOCF = Last observation carried forward.
[a]Analysis of covariance (ANCOVA) model with treatment groups (lixisenatide and sitagliptin), randomization strata of screening HbA1c (<8.0, ≥8.0%), randomization strata of screening BMI (<35, ≥35 kg/m$^2$), and country as fixed effects and baseline body weight as a covariate.
Note:
The analysis excluded measurements obtained after the introduction of rescue medication and/or after the treatment cessation plus 3 days.
Patients with both baseline and Week 24 (LOCF) measurements are included.

TABLE 42

Number (%) of patients with >=5% weight loss from baseline to Week 24 - mITT population

| Weight loss | Lixisenatide (N = 158) | Sitagliptin (N = 161) |
|---|---|---|
| Number | 152 | 160 |
| ≥5% | 28 (18.4%) | 19 (11.9%) |
| <5% | 124 (81.6%) | 141 (88.1%) |

Note:
The analysis excluded measurements obtained after the introduction of rescue medication and/or after the treatment cessation plus 3 days.
Patients with both baseline and Week 24 (LOCF) measurements are included.

TABLE 43

Mean change in 2-hour postprandial plasma glucose (mmol/L) from baseline to Week 24 - mITT population

| 2-hour postprandial plasma glucose (mmol/L) | Lixisenatide (N = 158) | Sitagliptin (N = 161) |
|---|---|---|
| Baseline | | |
| Number | 129 | 139 |
| Mean (SD) | 13.68 (3.85) | 13.82 (3.93) |
| Median | 13.71 | 14.10 |
| Min:Max | 4.4:23.9 | 3.9:23.9 |
| Week 24 (LOCF) | | |
| Number | 129 | 139 |
| Mean (SD) | 10.27 (4.48) | 12.15 (3.88) |
| Median | 9.71 | 11.88 |
| Min:Max | 3.4:22.4 | 3.7:23.2 |
| Change from baseline to week 24 (LOCF) | | |
| Number | 129 | 139 |
| Mean (SD) | −3.41 (5.31) | −1.66 (4.12) |
| Median | −3.22 | −1.88 |
| Min:Max | −17.3:11.2 | −12.2:9.1 |
| LS Mean (SE)[a] | −3.35 (0.377) | −1.44 (0.384) |
| LS Mean difference (SE) vs. Sitagliptin[a] | −1.91 (0.491) | — |
| 95% CI | (−2.876 to −0.941) | — |

LOCF = Last observation carried forward.
[a]Analysis of covariance (ANCOVA) model with treatment groups (lixisenatide and sitagliptin), randomization strata of screening HbA1c (<8.0, ≥8.0%), randomization strata of screening BMI (<35, ≥35 kg/m²), and country as fixed effects and baseline 2-hour postprandial plasma glucose value as a covariate.
Note:
The analysis excluded measurements obtained after the introduction of rescue medication and/or after the treatment cessation.
Patients with both baseline and Week 24 (LOCF) measurements are included.

TABLE 44

Mean change in fasting plasma glucose (mmol/L) from baseline to Week 24 - mITT population

| Fasting plasma glucose (mmol/L) | Lixisenatide (N = 158) | Sitagliptin (N = 161) |
|---|---|---|
| Baseline | | |
| Number | 153 | 161 |
| Mean (SD) | 9.10 (2.61) | 8.96 (2.59) |
| Median | 8.71 | 8.82 |
| Min:Max | 4.7:19.1 | 4.6:17.7 |
| Week 24 (LOCF) | | |
| Number | 153 | 161 |
| Mean (SD) | 8.68 (2.72) | 8.33 (2.64) |
| Median | 8.22 | 7.83 |
| Min:Max | 3.8:18.6 | 4.3:20.2 |
| Change from baseline to week 24 (LOCF) | | |
| Number | 153 | 161 |
| Mean (SD) | −0.42 (2.53) | −0.63 (2.37) |
| Median | −0.44 | −0.50 |
| Min:Max | −10.3:10.5 | −8.0:6.1 |
| LS Mean (SE)[a] | −0.45 (0.193) | −0.69 (0.198) |
| LS Mean difference (SE) vs. Sitagliptin[a] | 0.25 (0.254) | — |
| 95% CI | (−0.254 to 0.744) | — |

LOCF = Last observation carried forward.
[a]Analysis of covariance (ANCOVA) model with treatment groups (lixisenatide and sitagliptin), randomization strata of screening HbA1c (<8.0, ≥8.0%), randomization strata of screening BMI (<35, ≥35 kg/m²), and country as fixed effects and baseline fasting plasma glucose value as a covariate.
Note:
The analysis excluded measurements obtained after the introduction of rescue medication and/or after the treatment cessation plus 1 day.
Patients with both baseline and Week 24 (LOCF) measurements are included.

TABLE 45

Mean change in glucose excursion (mmol/L) from baseline to Week 24 - mITT population

| Glucose excursion (mmol/L) | Lixisenatide (N = 158) | Sitagliptin (N = 161) |
|---|---|---|
| Baseline | | |
| Number | 127 | 139 |
| Mean (SD) | 4.46 (2.65) | 4.47 (2.59) |
| Median | 4.50 | 4.33 |
| Min:Max | −4.6:10.2 | −3.7:12.2 |
| Week 24 (LOCF) | | |
| Number | 127 | 139 |
| Mean (SD) | 1.80 (3.31) | 3.87 (2.44) |
| Median | 1.83 | 3.89 |
| Min:Max | −5.8:10.5 | −3.3:10.7 |
| Change from baseline to week 24 (LOCF) | | |
| Number | 127 | 139 |
| Mean (SD) | −2.66 (4.11) | −0.60 (2.90) |
| Median | −2.28 | −0.83 |
| Min:Max | −15.2:6.7 | −7.0:10.1 |
| LS Mean (SE)[a] | −2.55 (0.272) | −0.42 (0.275) |
| LS Mean difference (SE) vs. Sitagliptin[a] | −2.13 (0.352) | — |
| 95% CI | (−2.819 to −1.434) | — |

LOCF = Last observation carried forward. Glucose excursion = 2-hour postprandial plasma glucose − plasma glucose 30 minutes prior to the meal test before study drug administration.
[a]Analysis of covariance (ANCOVA) model with treatment groups (lixisenatide and sitagliptin), randomization strata of screening HbA1c (<8.0, ≥8.0%), randomization strata of screening BMI (<35, ≥35 kg/m²), and country as fixed effects and baseline glucose excursion value as a covariate.
Note:
The analysis excluded measurements obtained after the introduction of rescue medication and/or after the treatment cessation.
Patients with both baseline and Week 24 (LOCF) measurements are included.

TABLE 46

Mean change in HOMA-IR from baseline to Week 24 - mITT population

| HOMA-IR | Lixisenatide (N = 158) | Sitagliptin (N = 161) |
|---|---|---|
| Baseline | | |
| Number | 118 | 133 |
| Mean (SD) | 6.24 (5.25) | 6.12 (5.08) |
| Median | 5.32 | 4.90 |
| Min:Max | 0.4:34.1 | 0.4:26.2 |
| Week 24 (LOCF) | | |
| Number | 118 | 133 |
| Mean (SD) | 5.52 (4.67) | 5.36 (4.31) |
| Median | 4.25 | 4.22 |
| Min:Max | 0.5:27.0 | 0.5:25.2 |
| Change from baseline to week 24 (LOCF) | | |
| Number | 118 | 133 |
| Mean (SD) | −0.72 (3.98) | −0.75 (4.13) |
| Median | −0.77 | −0.52 |
| Min:Max | −11.6:18.7 | −19.9:13.3 |
| LS Mean (SE)$^a$ | −0.52 (0.366) | −0.57 (0.378) |
| LS Mean difference (SE) vs. Sitagliptin$^a$ | 0.05 (0.442) | — |
| 95% CI | (−0.823 to 0.918) | — |

LOCF = Last observation carried forward.
$^a$Analysis of covariance (ANCOVA) model with treatment groups (lixisenatide and sitagliptin), randomization strata of screening HbA1c (<8.0, ≥8.0%), randomization strata of screening BMI (<35, ≥35 kg/m$^2$), and country as fixed effects and baseline HOMA-IR value as a covariate.
Note:
The analysis excluded measurements obtained after the introduction of rescue medication and/or after the treatment cessation.
Patients with both baseline and Week 24 (LOCF) measurements are included.

TABLE 47

Mean change in HOMA-beta from baseline to Week 24 - mITT population

| HOMA-β | Lixisenatide (N = 158) | Sitagliptin (N = 161) |
|---|---|---|
| Baseline | | |
| Number | 118 | 133 |
| Mean (SD) | 65.62 (64.28) | 60.33 (48.79) |
| Median | 48.81 | 47.65 |
| Min:Max | 5.2:398.2 | 3.0:272.9 |
| Week 24 (LOCF) | | |
| Number | 118 | 133 |
| Mean (SD) | 83.48 (123.35) | 79.24 (71.77) |
| Median | 52.82 | 58.37 |
| Min:Max | 2.6:953.9 | 6.0:412.7 |
| Change from baseline to week 24 (LOCF) | | |
| Number | 118 | 133 |
| Mean (SD) | 17.86 (116.39) | 18.91 (59.19) |
| Median | 3.15 | 8.32 |
| Min:Max | −164.8:897.1 | −122.1:341.9 |
| LS Mean (SE)$^a$ | 17.66 (9.652) | 17.79 (9.958) |
| LS Mean difference (SE) vs. Sitagliptin$^a$ | −0.13 (11.662) | — |
| 95% CI | (−23.108 to 22.842) | — |

LOCF = Last observation carried forward.
$^a$Analysis of covariance (ANCOVA) model with treatment groups (lixisenatide and sitagliptin), randomization strata of screening HbA1c (<8.0, ≥8.0%), randomization strata of screening BMI (<35, ≥35 kg/m$^2$), and country as fixed effects and baseline HOMA-β value as a covariate.
Note:
The analysis excluded measurements obtained after the introduction of rescue medication and/or after the treatment cessation.
Patients with both baseline and Week 24 (LOCF) measurements are included.

TABLE 48

Number (%) of patients requiring rescue therapy during the double-blind treatment period - mITT population

| Requiring rescue therapy | Lixisenatide (N = 158) | Sitagliptin (N = 161) |
|---|---|---|
| Number | 158 | 161 |
| Yes | 15 (9.5%) | 11 (6.8%) |

Safety

An overview of the adverse events observed during the on-treatment period is provided in Table 49. The proportion of patients who experienced TEAEs was slightly higher for the lixisenatide group versus the sitagliptin group (63.9% for lixisenatide versus 60.9% for sitagliptin). Six patients (3 [1.9%] in each group) had a serious TEAE. No death was reported in this study. The percentage of patients with TEAEs leading to treatment discontinuation was similar in each group (2.5% for lixisenatide and 3.1% for sitagliptin). Table 50 and Table 51 summarize serious TEAEs and TEAEs leading to treatment discontinuation by primary SOC, BLOT, HLT and PT, respectively.

Table 62 in the appendix presents the incidences of TEAEs occurring in at least 1% of patients in any treatment group. Nausea was the most frequently reported TEAE in the lixisenatide group (28 [17.7%] patients) versus 11 (6.8%) sitagliptin-treated patients. The second most frequently reported TEAE in the lixisenatide group was headache (20 [12.7%] patients for lixisenatide versus 15 [9.3%] patients for sitagliptin) followed by diarrhea (14 [8.9%] patients for lixisenatide versus 12 [7.5%] patients for sitagliptin).

TABLE 49

Overview of adverse event profile: treatment emergent adverse events - Safety population

| | Lixisenatide (N = 158) | Sitagliptin (N = 161) |
|---|---|---|
| Patients with any TEAE | 101 (63.9%) | 98 (60.9%) |
| Patients with any serious TEAE | 3 (1.9%) | 3 (1.9%) |
| Patients with any TEAE leading to death | 0 | 0 |
| Patients with any TEAE leading to permanent treatment discontinuation | 4 (2.5%) | 5 (3.1%) |

TEAE: Treatment Emergent Adverse Event
n (%) = number and percentage of patients with at least one adverse event

TABLE 50

Number (%) of patients experiencing serious TEAE(s) presented by primary SOC, HLGT, HLT, and PT - Safety population PRIMARY SYSTEM ORGAN CLASS
HLGT: High Level Group Term
HLT: High Level Term
Preferred Term

| | Lixisenatide (N = 158) | Sitagliptin (N = 161) |
|---|---|---|
| Any class | 3 (1.9%) | 3 (1.9%) |
| INFECTIONS AND INFESTATIONS | 0 | 1 (0.6%) |
| HLGT: Infections - pathogen unspecified | 0 | 1 (0.6%) |
| HLT: Infections NEC | 0 | 1 (0.6%) |
| Abscess limb | 0 | 1 (0.6%) |
| IMMUNE SYSTEM DISORDERS | 1 (0.6%) | 0 |
| HLGT: Allergic conditions | 1 (0.6%) | 0 |
| HLT: Anaphylactic responses | 1 (0.6%) | 0 |
| Anaphylactic reaction | 1 (0.6%) | 0 |
| VASCULAR DISORDERS | 1 (0.6%) | 0 |

TABLE 50-continued

Number (%) of patients experiencing serious TEAE(s) presented by primary SOC, HLGT, HLT, and PT - Safety population PRIMARY SYSTEM ORGAN CLASS
HLGT: High Level Group Term
HLT: High Level Term
Preferred Term

| | Lixisenatide (N = 158) | Sitagliptin (N = 161) |
|---|---|---|
| HLGT: Vascular disorders NEC | 1 (0.6%) | 0 |
| HLT: Vascular malformations and acquired anomalies | 1 (0.6%) | 0 |
| Arteriovenous fistula | 1 (0.6%) | 0 |
| HEPATOBILIARY DISORDERS | 0 | 1 (0.6%) |
| HLGT: Bile duct disorders | 0 | 1 (0.6%) |
| HLT: Obstructive bile duct disorders (excl neoplasms) | 0 | 1 (0.6%) |
| Bile duct stone | 0 | 1 (0.6%) |
| RENAL AND URINARY DISORDERS | 1 (0.6%) | 1 (0.6%) |
| HLGT: Renal disorders (excl nephropathies) | 0 | 1 (0.6%) |
| HLT: Renal failure and impairment | 0 | 1 (0.6%) |
| Renal failure | 0 | 1 (0.6%) |
| HLGT: Urolithiases | 1 (0.6%) | 0 |
| HLT: Renal lithiasis | 1 (0.6%) | 0 |
| Nephrolithiasis | 1 (0.6%) | 0 |

TEAE: Treatment Emergent Adverse Event,
SOC: System Organ Class,
HLGT: High Level Group Term,
HLT: High Level Term,
PT: Preferred Term.
MedDRA version: 13.1.
n (%) = number and percentage of patients with at least one serious TEAE.
Note:
On-treatment period = the time from the first dose of double-blind study medication up to 3 days after the last dose administration.
Table sorted by SOC internationally agreed order and HLGT, HLT, PT alphabetic order.

TABLE 51

Number (%) of patients experiencing TEAE(s) leading to permanent treatment discontinuation by primary SOC, HLGT, HLT, and PT - Safety population PRIMARY SYSTEM ORGAN CLASS
HLGT: High Level Group Term
HLT: High Level Term
Preferred Term

| | Lixisenatide (N = 158) | Sitagliptin (N = 161) |
|---|---|---|
| Any class | 4 (2.5%) | 5 (3.1%) |
| INFECTIONS AND INFESTATIONS | 0 | 1 (0.6%) |
| HLGT: Infections - pathogen unspecified | 0 | 1 (0.6%) |
| HLT: Infections NEC | 0 | 1 (0.6%) |
| Abscess limb | 0 | 1 (0.6%) |
| IMMUNE SYSTEM DISORDERS | 1 (0.6%) | 0 |
| HLGT: Allergic conditions | 1 (0.6%) | 0 |
| HLT: Anaphylactic responses | 1 (0.6%) | 0 |
| Anaphylactic reaction | 1 (0.6%) | 0 |
| NERVOUS SYSTEM DISORDERS | 0 | 1 (0.6%) |
| HLGT: Neurological disorders NEC | 0 | 1 (0.6%) |
| HLT: Disturbances in consciousness NEC | 0 | 1 (0.6%) |
| Somnolence | 0 | 1 (0.6%) |
| GASTROINTESTINAL DISORDERS | 1 (0.6%) | 0 |
| HLGT: Gastrointestinal motility and defaecation conditions | 1 (0.6%) | 0 |
| HLT: Diarrhoea (excl infective) | 1 (0.6%) | 0 |
| Diarrhoea | 1 (0.6%) | 0 |
| HLGT: Gastrointestinal signs and symptoms | 1 (0.6%) | 0 |
| HLT: Gastrointestinal and abdominal pains (excl oral and throat) | 1 (0.6%) | 0 |
| Abdominal pain upper | 1 (0.6%) | 0 |
| HLT: Nausea and vomiting symptoms | 1 (0.6%) | 0 |
| Nausea | 1 (0.6%) | 0 |
| Vomiting | 1 (0.6%) | 0 |
| HEPATOBILIARY DISORDERS | 0 | 1 (0.6%) |
| HLGT: Bile duct disorders | 0 | 1 (0.6%) |
| HLT: Obstructive bile duct disorders (excl neoplasms) | 0 | 1 (0.6%) |
| Bile duct stone | 0 | 1 (0.6%) |
| RENAL AND URINARY DISORDERS | 0 | 1 (0.6%) |

TABLE 51-continued

Number (%) of patients experiencing TEAE(s) leading to permanent treatment discontinuation by primary SOC, HLGT, HLT, and PT - Safety population PRIMARY SYSTEM ORGAN CLASS
HLGT: High Level Group Term
HLT: High Level Term
Preferred Term

| | Lixisenatide (N = 158) | Sitagliptin (N = 161) |
|---|---|---|
| HLGT: Renal disorders (excl nephropathies) | 0 | 1 (0.6%) |
| HLT: Renal failure and impairment | 0 | 1 (0.6%) |
| Renal failure | 0 | 1 (0.6%) |
| INVESTIGATIONS | 2 (1.3%) | 1 (0.6%) |
| HLGT: Gastrointestinal investigations | 1 (0.6%) | 0 |
| HLT: Digestive enzymes | 1 (0.6%) | 0 |
| Lipase increased | 1 (0.6%) | 0 |
| HLGT: Haematology investigations (incl blood groups) | 0 | 1 (0.6%) |
| HLT: Platelet analyses | 0 | 1 (0.6%) |
| Platelet count decreased | 0 | 1 (0.6%) |
| HLGT: Hepatobiliary investigations | 1 (0.6%) | 0 |
| HLT: Liver function analyses | 1 (0.6%) | 0 |
| Alanine aminotransferase increased | 1 (0.6%) | 0 |

TEAE: Treatment Emergent Adverse Event,
SOC: System Organ Class,
HLGT: High Level Group Term,
HLT: High Level Term,
PT: Preferred Term.
MedDRA version: 13.1.
n (%) = number and percentage of patients with at least one TEAE leading to permanent treatment discontinuation.
Note:
On-treatment period = the time from the first dose of double-blind study medication up to 3 days after the last dose administration.
Table sorted by SOC internationally agreed order and HLGT, HLT, PT alphabetic order.

During the on-treatment period, 1 (0.6%) lixisenatide-treated patient reported 2 symptomatic hypoglycemia events as defined in the protocol. During the same period, 3 (1.9%) sitagliptin-treated patients experienced a symptomatic hypoglycemia event (Table 52). None of these symptomatic hypoglycemia events was severe according to the protocol definition. Three additional patients (1 for lixisenatide and 2 for sitagliptin) reported hypoglycemia (Table 62), which did not meet the protocol definition (the associated glucose values were ≥60 mg/dL).

TABLE 52

Summary of symptomatic hypoglycemia during the on-treatment period - Safety population

| Type | Lixisenatide (N = 158) | Sitagliptin (N = 161) |
|---|---|---|
| Total patient years | 69.5 | 73.6 |
| Any symptomatic hypoglycemia | | |
| Number of patients with events, n (%) | 1 (0.6%) | 3 (1.9%) |
| Number of patients with events per 100 patient years[a] | 1.4 | 4.1 |
| Blood glucose <60 mg/dL | | |
| Number of patients with events, n (%) | 1 (0.6%) | 1 (0.6%) |
| Number of patients with events per 100 patient years[a] | 1.4 | 1.4 |
| No blood glucose reported | | |
| Number of patients with events, n (%) | 0 | 2 (1.2%) |
| Number of patients with events per 100 patient years[a] | 0.0 | 2.7 |

[a]Calculated as (number of patients with events * 100 divided by total exposure + 3 days in patient years).
Symptomatic hypoglycemia = Symptomatic hypoglycemia as defined per protocol.
Note:
On-treatment period = the time from the first dose of double-blind study medication up to 3 days after the last dose administration.

Eleven patients (9 [5.7%] lixisenatide-treated patients and 2 [1.2%] sitagliptin-treated patients) experienced injection site reaction AEs (Table 53). The injection site reaction AEs were identified by searching for the term "injection site" in either the PTs coded from the investigator reported terms or the PTs from the ARAC diagnosis after the allergic reaction adjudication. None of the reactions was serious or severe in intensity.

TABLE 53

Number (%) of patients experiencing injection site reactions during the on-treatment period - Safety population

| Event source Preferred Term | Lixisenatide (N = 158) | Sitagliptin (N = 161) |
|---|---|---|
| Any injection site reactions | 9 (5.7%) | 2 (1.2%) |
| Investigator reported PTs | 9 (5.7%) | 2 (1.2%) |
| Injection site haematoma | 3 (1.9%) | 2 (1.2%) |
| Injection site erythema | 2 (1.3%) | 0 |
| Injection site pruritus | 2 (1.3%) | 0 |
| Injection site haemorrhage | 1 (0.6%) | 0 |
| Injection site infection | 1 (0.6%) | 0 |
| Injection site pain | 1 (0.6%) | 1 (0.6%) |
| Injection site papule | 1 (0.6%) | 0 |
| Injection site rash | 1 (0.6%) | 0 |
| PTs by ARAC diagnosis | 0 | 0 |

ARAC = Allergic Reaction Assessment Committee.
Note:
On-treatment period = the time from the first dose of double-blind study medication up to 3 days after the last dose administration.

A total of 5 events were reported as possible allergic events by investigators during the on-treatment period and sent to ARAC for adjudication. Of these, 3 events from 3 patients (2 [1.3%] lixisenatide-treated patients and 1 [0.6%] sitagliptin-treated patient) were adjudicated as allergic reactions by the ARAC, but only one event (anaphylactic reaction) from one lixisenatide-treated patient (#320001015) was adjudicated as possibly related to IP (Table 54).

Patient #320001015, a 48-year old a 48-year old postmenopausal woman, with a history of hypertension and obesity, experienced on the second day of treatment, 10 minutes after IP administration an allergic reaction of moderate intensity (she developed generalized pruritus, swelling of her eyes, face, hands and feet, associated with chest tightness. At examination, she was noted to have also flushing, hives, and swelling at the injection site. She received dexamethasone and chlorphenamine. After 30 minutes without improvement, she was taken to emergency room to receive IV dexamethasone, SC epinephrine, and nasal route oxygen. The reaction resolved 90 minutes after this treatment, and 1 hour later the patient was discharged home without complications. IP was permanently discontinued the day of the allergic reaction. Per investigator this AE was associated with lixisenatide (or its placebo), while per sponsor, relationship was not excluded. ARAC adjudicated this AE as "allergic reaction (anaphylactic reaction)". At a follow-up visit 5 days later, the patient had no more reaction and felt well.

TABLE 54

Number (%) of patients with events adjudicated as allergic reaction by ARAC during the on-treatment period - Safety population

| Relationship to study treatment (by ARAC) | MedDRA coded term (PT) for ARAC diagnosis | ARAC diagnosis | Lixisenatide (N = 158) | Sitagliptin (N = 161) |
|---|---|---|---|---|
| All | Events adjudicated as an allergic reaction by ARAC | | 2 (1.3%) | 1 (0.6%) |
| | Anaphylactic reaction | ANAPHYLACTIC REACTION | 1 (0.6%) | 0 |
| | Conjunctivitis allergic | ALLERGIC CONJUNCTIVITIS | 1 (0.6%) | 0 |
| | Dermatitis contact | ALLERGIC CONTACT DERMATITIS | 0 | 1 (0.6%) |
| Possibly Related to IP | Events adjudicated as an allergic reaction by ARAC | | 1 (0.6%) | 0 |
| | Anaphylactic reaction | ANAPHYLACTIC REACTION | 1 (0.6%) | 0 |
| Not related to IP | Events adjudicated as an allergic reaction by ARAC | | 1 (0.6%) | 1 (0.6%) |
| | Conjunctivitis allergic | ALLERGIC CONJUNCTIVITIS | 1 (0.6%) | 0 |
| | Dermatitis contact | ALLERGIC CONTACT DERMATITIS | 0 | 1 (0.6%) |

ARAC = Allergic Reaction Assessment Committee.
IP = Investigational Product.
Note:
On-treatment period = the time from the first dose of double-blind study medication up to 3 days after the last dose administration.

Per protocol, any increase in amylase and/or lipase above twice the upper limit of normal range (ULN) that had been confirmed by a repeat measurement was to be monitored and documented on a pre-specified AE form for "suspected pancreatitis". During the on-treatment period, this form was completed for 6 (3.8%) lixisenatide-treated patients and 2 (1.2%) sitagliptin-treated patients (Table 55). Among these 8 patients, the PT was blood amylase increased for one sitagliptin-treated patient and lipase increased for 6 lixisenatide-treated patients and one sitagliptin-treated patient. No case of pancreatitis was reported during the study.

TABLE 55

Number (%) of patients with a specific adverse event form for suspected pancreatitis completed during the on-treatment period - Safety population

| Preferred Term | Lixisenatide (N = 158) | Sitagliptin (N = 161) |
| --- | --- | --- |
| Any | 6 (3.8%) | 2 (1.2%) |
| Blood amylase increased | 0 | 1 (0.6%) |
| Lipase increased | 6 (3.8%) | 1 (0.6%) | n (%) = number and percentage of patients with any cases reported on the AE form for suspected pancreatitis along with complementary form.
Note:
On-treatment period = the time from the first dose of double-blind study medication up to 3 days after the last dose administration.

Patients who had at least one value of lipase or amylase ≥3 ULN during the on-treatment period are summarized in Table 56. A total of 5 patients (2 [1.3%] patients in the lixisenatide group and 3 [1.9%] in the sitagliptin group) with elevated lipase 3ULN) was observed. No one had elevated amylase 3ULN) during the on-treatment period.

TABLE 56

Pancreatic enzymes: Number (%) of patients with at least one post-baseline PCSA during the on-treatment period according to baseline status - Safety population

| Laboratory parameter Baseline By PCSA criteria n/N1 (%) | Lixisenatide (N = 158) | Sitagliptin (N = 161) |
| --- | --- | --- |
| Lipase (IU/L) Total* | | |
| ≥3 ULN Normal/Missing | 2/153 (1.3%) | 3/161 (1.9%) |
| ≥3 ULN Amylase (IU/L) Total* | 2/152 (1.3%) | 3/161 (1.9%) |
| ≥3 ULN Normal/Missing | 0/153 | 0/161 |
| ≥3 ULN | 0/153 | 0/161 |

PCSA: Potentially Clinically Significant Abnormalities,
ULN = Upper limit of normal.
*Regardless of baseline.
Note:
On-treatment period = the time from the first dose of double-blind study medication up to 3 days after the last dose administration.
The number (n) represents the subset of the total number of patients who met the criterion in question at least once. The denominator (/N1) for each parameter within a treatment group is the number of patients for the treatment group who had that parameter assessed post-baseline by baseline PCSA status.
Only the worsening of the worst case for each patient is presented by baseline status.

Per protocol, any calcitonin value ≥20 pg/mL confirmed by a repeat measurement was to be monitored and reported on the pre-specified AE form for "increased calcitonin ≥20 pg/mL". During the on-treatment period, this form was completed for 1 (0.6%) sitagliptin-treated patient (57). The PT was blood calcitonin increased. The corresponding calcitonin value was 22 ng/L.

TABLE 57

Number (%) of patients with a specific adverse event form for increased calcitonin ≥20 pg/mL completed during the on-treatment period - Safety population

| Preferred Term | Lixisenatide (N = 158) | Sitagliptin (N = 161) |
| --- | --- | --- |
| Any | 0 | 1 (0.6%) |
| Blood calcitonin increased | 0 | 1 (0.6%) | n (%) = number and percentage of patients with any cases reported on the AE form for increased calcitonin ≥20 pg/mL.
Note:
On-treatment period = the time from the first dose of double-blind study medication up to 3 days after the last dose administration.

Patients with at least one serum calcitonin measurement during the on-treatment period are summarized in Table 58 according to the 4 pre-defined categories of calcitonin level at baseline. One (0.7%) patient with baseline calcitonin value "≥20 ng/L-<50 ng/L" in the lixisenatide group and 1 (0.6%) patient with baseline calcitonin value ">ULN-<20 ng/L" in the sitagliptin group had at least one value of calcitonin "≥20 ng/L-<50 ng/L" during the on-treatment period. Of the two patients, the sitagliptin-treated patient reported a TEAE with the pre-specified AE form (Table 57) while the lixisenatide-treated patient did not because of an unconfirmed elevation with a subsequent calcitonin value <20 ng/L.

TABLE 58

Serum calcitonin - Number (%) of patients by pre-defined categories during the on-treatment period according to baseline category - Safety population

| Laboratory criteria Baseline status Post-baseline | Lixisenatide (N = 158) | Sitagliptin (N = 161) |
| --- | --- | --- |
| Calcitonin (ng/L) Total* | | |
| ≤ULN | 140/145 (96.6%) | 141/154 (91.6%) |
| >ULN-<20 ng/L | 4/145 (2.8%) | 12/154 (7.8%) |
| ≥20 ng/L-<50 ng/L | 1/145 (0.7%) | 1/154 (0.6%) |
| ≥50 ng/L | 0/145 | 0/154 |
| Missing | | |
| ≤ULN | 0/0 | 1/1 (100%) |
| >ULN-<20 ng/L | 0/0 | 0/1 |
| ≥20 ng/L-<50 ng/L | 0/0 | 0/1 |
| ≥50 ng/L | 0/0 | 0/1 |
| ≤ULN | | |
| ≤ULN | 138/140 (98.6%) | 139/144 (96.5%) |
| >ULN-<20 ng/L | 2/140 (1.4%) | 5/144 (3.5%) |
| ≥20 ng/L-<50 ng/L | 0/140 | 0/144 |
| ≥50 ng/L | 0/140 | 0/144 |
| >ULN-<20 ng/L | | |
| ≤ULN | 2/4 (50.0%) | 1/9 (11.1%) |
| >ULN-<20 ng/L | 2/4 (50.0%) | 7/9 (77.8%) |
| ≥20 ng/L-<50 ng/L | 0/4 | 1/9 (11.1%) |
| ≥50 ng/L | 0/4 | 0/9 |
| ≥20 ng/L-<50 ng/L | | |
| ≤ULN | 0/1 | 0/0 |
| >ULN-<20 ng/L | 0/1 | 0/0 |
| ≥20 ng/L-<50 ng/L | 1/1 (100%) | 0/0 |
| ≥50 ng/L | 0/1 | 0/0 |
| ≥50 ng/L | | |
| ≤ULN | 0/0 | 0/0 |
| >ULN-<20 ng/L | 0/0 | 0/0 |

TABLE 58-continued

Serum calcitonin - Number (%) of patients by pre-defined categories during the on-treatment period according to baseline category - Safety population

| Laboratory criteria Baseline status Post-baseline | Lixisenatide (N = 158) | Sitagliptin (N = 161) |
|---|---|---|
| ≥20 ng/L-<50 ng/L | 0/0 | 0/0 |
| ≥50 ng/L | 0/0 | 0/0 |

ULN = Upper limit of normal
*Regardless of baseline.
Note:
On-treatment period = the time from the first dose of double-blind study medication up to 3 days after the last dose administration.
The numerator represents the number of patients who were in the pre-specified categories at post-baseline in each baseline category.
The denominator for each parameter within a treatment group is the number of patients for the treatment group who had that parameter assessed post-baseline by baseline status.
A patient is counted only in the worst category.

APPENDIX

TABLE 59

Number (%) of responders (patients with HbA1c <7% and weight loss of ≥5% of baseline body weight) by visit - mITT population

| Visit | Responder | Lixisenatide (N = 158) | Sitagliptin (N = 161) |
|---|---|---|---|
| Week 4 | Number | 145 | 157 |
|  | Yes | 1 (0.7%) | 0 |
|  | No | 144 (99.3%) | 157 (100%) |
| Week 8 | Number | 140 | 153 |
|  | Yes | 3 (2.1%) | 3 (2.0%) |
|  | No | 137 (97.9%) | 150 (98.0%) |
| Week 12 | Number | 140 | 150 |
|  | Yes | 4 (2.9%) | 6 (4.0%) |
|  | No | 136 (97.1%) | 144 (96.0%) |
| Week 16 | Number | 138 | 146 |
|  | Yes | 12 (8.7%) | 5 (3.4%) |
|  | No | 126 (91.3%) | 141 (96.6%) |
| Week 24 | Number | 125 | 136 |
|  | Yes | 18 (14.4%) | 12 (8.8%) |
|  | No | 107 (85.6%) | 124 (91.2%) |
| Week 24 (LOCF) | Number | 158 | 161 |
|  | Yes | 19 (12.0%) | 12 (7.5%) |
|  | No | 139 (88.0%) | 149 (92.5%) |

LOCF = Last observation carried forward.
Note:
The analysis excluded measurements obtained after the introduction of rescue medication and/or after the treatment cessation plus 3 days.
For week 24 (LOCF), patients who do not have post-baseline on-treatment values (HbA1c and body weight) that are no more than 30 days apart are counted as non-responders.

TABLE 60

Mean change in HbA1c (%) from baseline by visit - mITT population

| Treatment Time point | Observed data | | | | | | | Change from baseline | | | | | | |
|---|---|---|---|---|---|---|---|---|---|---|---|---|---|---|
|  | N | Mean | SD | SE | Median | Min | Max | N | Mean | SD | SE | Median | Min | Max |
| Lixisenatide (N = 158) | | | | | | | | | | | | | | |
| Screening | 158 | 8.28 | 0.87 | 0.069 | 8.10 | 7.0 | 10.1 | | | | | | | |
| Baseline | 158 | 8.16 | 0.89 | 0.071 | 8.10 | 6.4 | 10.1 | | | | | | | |
| Week 4 | 145 | 7.75 | 0.94 | 0.078 | 7.60 | 5.8 | 10.2 | 145 | −0.42 | 0.48 | 0.040 | −0.40 | −2.0 | 1.0 |
| Week 8 | 140 | 7.52 | 1.00 | 0.084 | 7.40 | 5.7 | 10.5 | 140 | −0.64 | 0.75 | 0.064 | −0.70 | −2.3 | 1.5 |
| Week 12 | 140 | 7.34 | 1.04 | 0.088 | 7.10 | 5.4 | 10.8 | 140 | −0.79 | 0.85 | 0.072 | −0.80 | −2.9 | 1.2 |
| Week 16 | 138 | 7.38 | 1.10 | 0.094 | 7.10 | 5.5 | 11.1 | 138 | −0.74 | 0.94 | 0.080 | −0.75 | −3.0 | 2.2 |
| Week 24 | 125 | 7.27 | 1.14 | 0.102 | 7.10 | 4.8 | 12.9 | 125 | −0.76 | 1.17 | 0.105 | −0.90 | −4.0 | 4.4 |
| Week 24 (LOCF) | 150 | 7.52 | 1.26 | 0.103 | 7.40 | 4.8 | 12.9 | 150 | −0.65 | 1.15 | 0.094 | −0.70 | −4.0 | 4.4 |
| Sitagliptin (N = 161) | | | | | | | | | | | | | | |
| Screening | 161 | 8.25 | 0.83 | 0.065 | 8.20 | 7.0 | 10.0 | | | | | | | |
| Baseline | 161 | 8.09 | 0.96 | 0.076 | 8.00 | 5.0 | 11.0 | | | | | | | |
| Week 4 | 157 | 7.64 | 1.01 | 0.081 | 7.50 | 5.3 | 10.8 | 157 | −0.46 | 0.54 | 0.043 | −0.40 | −2.1 | 1.5 |
| Week 8 | 153 | 7.41 | 1.01 | 0.082 | 7.30 | 5.4 | 10.9 | 153 | −0.68 | 0.76 | 0.062 | −0.60 | −2.6 | 2.4 |
| Week 12 | 150 | 7.26 | 1.04 | 0.085 | 7.20 | 5.3 | 11.4 | 150 | −0.81 | 0.88 | 0.072 | −0.80 | −3.4 | 2.3 |
| Week 16 | 146 | 7.26 | 1.04 | 0.086 | 7.15 | 5.1 | 10.6 | 146 | −0.79 | 0.93 | 0.077 | −0.70 | −3.7 | 1.6 |
| Week 24 | 137 | 7.21 | 1.04 | 0.089 | 7.20 | 5.3 | 11.0 | 137 | −0.81 | 1.00 | 0.085 | −0.80 | −3.6 | 1.7 |
| Week 24 (LOCF) | 160 | 7.38 | 1.26 | 0.099 | 7.30 | 5.3 | 11.9 | 160 | −0.70 | 1.08 | 0.086 | −0.70 | −3.6 | 3.7 |

LOCF = Last observation carried forward.
Note:
The analysis excluded measurements obtained after the introduction of rescue medication and/or after the trreatment cessation plus 3 days.

TABLE 61

Mean change in body weight (kg) from baseline by visit - mITT population

| Treatment | Observed data | | | | | | | Change from baseline | | | | | |
|---|---|---|---|---|---|---|---|---|---|---|---|---|---|
| Time point | N | Mean | SD | SE | Median | Min | Max | N | Mean | SD | SE | Median | Min | Max |
| Lixisenatide (N = 158) | | | | | | | | | | | | | | |
| Screening | 158 | 98.83 | 23.47 | 1.867 | 95.20 | 54.8 | 180.7 | | | | | | | |
| Baseline | 158 | 98.51 | 23.48 | 1.868 | 94.50 | 54.4 | 180.6 | | | | | | | |
| Week 4 | 150 | 98.09 | 23.98 | 1.958 | 94.90 | 54.7 | 179.2 | 150 | −0.93 | 1.66 | 0.136 | −1.00 | −5.5 | 5.0 |
| Week 8 | 146 | 98.10 | 23.90 | 1.978 | 93.90 | 55.0 | 182.2 | 146 | −1.43 | 2.17 | 0.180 | −1.45 | −12.0 | 3.6 |
| Week 12 | 143 | 97.27 | 23.80 | 1.990 | 93.30 | 56.0 | 175.6 | 143 | −1.93 | 2.35 | 0.197 | −1.90 | −11.2 | 3.5 |
| Week 16 | 140 | 97.11 | 23.78 | 2.010 | 92.70 | 54.0 | 176.7 | 140 | −2.05 | 2.80 | 0.236 | −2.15 | −12.1 | 5.7 |
| Week 24 | 127 | 95.70 | 23.80 | 2.112 | 92.00 | 53.4 | 174.3 | 127 | −2.53 | 3.57 | 0.317 | −1.80 | −17.0 | 5.6 |
| Week 24 (LOCF) | 152 | 96.50 | 23.61 | 1.915 | 92.25 | 53.4 | 174.3 | 152 | −2.24 | 3.46 | 0.281 | −1.60 | −17.0 | 5.6 |
| Sitagliptin (N = 161) | | | | | | | | | | | | | | |
| Screening | 161 | 100.73 | 23.57 | 1.857 | 97.20 | 59.3 | 177.5 | | | | | | | |
| Baseline | 161 | 100.56 | 23.77 | 1.873 | 97.30 | 59.3 | 180.8 | | | | | | | |
| Week 4 | 160 | 99.80 | 23.64 | 1.869 | 97.30 | 58.9 | 180.2 | 160 | −0.53 | 1.58 | 0.125 | −0.30 | −6.0 | 4.5 |
| Week 8 | 155 | 99.17 | 23.51 | 1.889 | 97.20 | 58.5 | 179.5 | 155 | −0.75 | 1.99 | 0.160 | −0.70 | −6.0 | 5.0 |
| Week 12 | 152 | 98.32 | 23.10 | 1.873 | 96.55 | 59.7 | 182.5 | 152 | −0.92 | 2.50 | 0.203 | −0.55 | −7.6 | 6.0 |
| Week 16 | 148 | 98.16 | 23.25 | 1.911 | 96.15 | 58.0 | 180.5 | 148 | −0.99 | 2.81 | 0.231 | −0.80 | −8.0 | 6.0 |
| Week 24 | 139 | 97.91 | 22.71 | 1.926 | 97.00 | 57.8 | 183.0 | 139 | −0.97 | 3.45 | 0.293 | −0.50 | −11.0 | 8.5 |
| Week 24 (LOCF) | 160 | 99.43 | 24.00 | 1.897 | 97.35 | 57.8 | 183.0 | 160 | −0.89 | 3.37 | 0.266 | −0.50 | −11.0 | 8.5 |

LOCF = Last observation carried forward.
Note:
The analysis excluded measurements obtained after the introduction of rescue medication and/or after the treatment cessation plus 3 days.

TABLE 62

Number (%) of patients experiencing common TEAE(s) (PT ≥1% in any treatment group) presented by primary SOC, HLGT, HLT and PT - Safety population

| PRIMARY SYSTEM ORGAN CLASS HLGT: High Level Group Term HLT: High Level Term Preferred Term | Lixisenatide (N = 158) | Sitagliptin (N = 161) |
|---|---|---|
| Any class | 101 (63.9%) | 98 (60.9%) |
| INFECTIONS AND INFESTATIONS | 46 (29.1%) | 51 (31.7%) |
| HLGT: Bacterial infectious disorders | 0 | 2 (1.2%) |
| HLT: Bacterial infections NEC | 0 | 2 (1.2%) |
| Cellulitis | 0 | 2 (1.2%) |
| HLGT: Infections - pathogen unspecified | 34 (21.5%) | 39 (24.2%) |
| HLT: Abdominal and gastrointestinal infections | 1 (0.6%) | 7 (4.3%) |
| Gastroenteritis | 1 (0.6%) | 7 (4.3%) |
| HLT: Dental and oral soft tissue infections | 2 (1.3%) | 0 |
| Tooth infection | 2 (1.3%) | 0 |
| HLT: Ear infections | 3 (1.9%) | 2 (1.2%) |
| Ear infection | 3 (1.9%) | 1 (0.6%) |
| HLT: Infections NEC | 2 (1.3%) | 4 (2.5%) |
| Respiratory tract infection | 1 (0.6%) | 2 (1.2%) |
| HLT: Lower respiratory tract and lung infections | 4 (2.5%) | 4 (2.5%) |
| Bronchitis | 4 (2.5%) | 4 (2.5%) |
| HLT: Upper respiratory tract infections | 19 (12.0%) | 23 (14.3%) |
| Nasopharyngitis | 10 (6.3%) | 12 (7.5%) |
| Pharyngitis | 1 (0.6%) | 3 (1.9%) |
| Pharyngotonsillitis | 2 (1.3%) | 0 |
| Sinusitis | 2 (1.3%) | 1 (0.6%) |
| Upper respiratory tract infection | 3 (1.9%) | 6 (3.7%) |
| HLT: Urinary tract infections | 4 (2.5%) | 2 (1.2%) |
| Urinary tract infection | 3 (1.9%) | 2 (1.2%) |
| HLGT: Viral infectious disorders | 11 (7.0%) | 11 (6.8%) |
| HLT: Influenza viral infections | 8 (5.1%) | 5 (3.1%) |
| Influenza | 8 (5.1%) | 5 (3.1%) |
| HLT: Viral infections NEC | 2 (1.3%) | 6 (3.7%) |
| Gastroenteritis viral | 0 | 3 (1.9%) |
| BLOOD AND LYMPHATIC SYSTEM DISORDERS | 2 (1.3%) | 2 (1.2%) |
| HLGT: Anaemias nonhaemolytic and marrow depression | 0 | 2 (1.2%) |
| HLT: Anaemias NEC | 0 | 2 (1.2%) |
| Anaemia | 0 | 2 (1.2%) |
| METABOLISM AND NUTRITION DISORDERS | 15 (9.5%) | 15 (9.3%) |
| HLGT: Appetite and general nutritional disorders | 3 (1.9%) | 0 |
| HLT: Appetite disorders | 3 (1.9%) | 0 |
| Decreased appetite | 2 (1.3%) | 0 |
| HLGT: Glucose metabolism disorders (incl diabetes mellitus) | 4 (2.5%) | 7 (4.3%) |
| HLT: Hyperglycaemic conditions NEC | 2 (1.3%) | 2 (1.2%) |
| Hyperglycaemia | 2 (1.3%) | 2 (1.2%) |
| HLT: Hypoglycaemic conditions NEC | 2 (1.3%) | 5 (3.1%) |
| Hypoglycaemia | 2 (1.3%) | 5 (3.1%) |
| HLGT: Lipid metabolism disorders | 6 (3.8%) | 3 (1.9%) |
| HLT: Elevated triglycerides | 2 (1.3%) | 1 (0.6%) |
| Hypertriglyceridaemia | 2 (1.3%) | 1 (0.6%) |
| HLT: Lipid metabolism and deposit disorders NEC | 4 (2.5%) | 2 (1.2%) |
| Dyslipidaemia | 4 (2.5%) | 2 (1.2%) |
| HLGT: Purine and pyrimidine metabolism disorders | 2 (1.3%) | 3 (1.9%) |
| HLT: Purine metabolism disorders NEC | 2 (1.3%) | 3 (1.9%) |
| Gout | 1 (0.6%) | 2 (1.2%) |
| PSYCHIATRIC DISORDERS | 17 (10.8%) | 7 (4.3%) |
| HLGT: Anxiety disorders and symptoms | 9 (5.7%) | 3 (1.9%) |
| HLT: Anxiety symptoms | 8 (5.1%) | 3 (1.9%) |
| Anxiety | 5 (3.2%) | 3 (1.9%) |

TABLE 62-continued

Number (%) of patients experiencing common TEAE(s) (PT ≥1% in any treatment group) presented by primary SOC, HLGT, HLT and PT - Safety population

| PRIMARY SYSTEM ORGAN CLASS<br>HLGT: High Level Group Term<br>HLT: High Level Term<br>Preferred Term | Lixisenatide (N = 158) | Sitagliptin (N = 161) |
|---|---|---|
| Stress | 2 (1.3%) | 0 |
| HLGT: Depressed mood disorders and disturbances | 2 (1.3%) | 0 |
| HLT: Depressive disorders | 2 (1.3%) | 0 |
| Depression | 2 (1.3%) | 0 |
| HLGT: Sexual dysfunctions, disturbances and gender identity disorders | 2 (1.3%) | 1 (0.6%) |
| HLT: Sexual desire disorders | 2 (1.3%) | 1 (0.6%) |
| Libido decreased | 2 (1.3%) | 1 (0.6%) |
| HLGT: Sleep disorders and disturbances | 3 (1.9%) | 3 (1.9%) |
| HLT: Disturbances in initiating and maintaining sleep | 2 (1.3%) | 2 (1.2%) |
| Insomnia | 2 (1.3%) | 2 (1.2%) |
| NERVOUS SYSTEM DISORDERS | 29 (18.4%) | 20 (12.4%) |
| HLGT: Headaches | 20 (12.7%) | 15 (9.3%) |
| HLT: Headaches NEC | 20 (12.7%) | 15 (9.3%) |
| Headache | 20 (12.7%) | 15 (9.3%) |
| HLGT: Neurological disorders NEC | 12 (7.6%) | 7 (4.3%) |
| HLT: Disturbances in consciousness NEC | 3 (1.9%) | 1 (0.6%) |
| Somnolence | 3 (1.9%) | 1 (0.6%) |
| HLT: Neurological signs and symptoms NEC | 8 (5.1%) | 5 (3.1%) |
| Dizziness | 8 (5.1%) | 5 (3.1%) |
| EYE DISORDERS | 5 (3.2%) | 0 |
| HLGT: Vision disorders | 2 (1.3%) | 0 |
| HLT: Visual disorders NEC | 2 (1.3%) | 0 |
| Vision blurred | 2 (1.3%) | 0 |
| CARDIAC DISORDERS | 2 (1.3%) | 5 (3.1%) |
| HLGT: Cardiac arrhythmias | 1 (0.6%) | 3 (1.9%) |
| HLT: Rate and rhythm disorders NEC | 1 (0.6%) | 2 (1.2%) |
| Tachycardia | 1 (0.6%) | 2 (1.2%) |
| HLGT: Cardiac disorder signs and symptoms | 1 (0.6%) | 2 (1.2%) |
| HLT: Cardiac signs and symptoms NEC | 1 (0.6%) | 2 (1.2%) |
| Palpitations | 1 (0.6%) | 2 (1.2%) |
| VASCULAR DISORDERS | 2 (1.3%) | 5 (3.1%) |
| HLGT: Vascular hypertensive disorders | 1 (0.6%) | 4 (2.5%) |
| HLT: Vascular hypertensive disorders NEC | 1 (0.6%) | 4 (2.5%) |
| Hypertension | 1 (0.6%) | 4 (2.5%) |
| RESPIRATORY, THORACIC AND MEDIASTINAL DISORDERS | 6 (3.8%) | 8 (5.0%) |
| HLGT: Respiratory disorders NEC | 6 (3.8%) | 6 (3.7%) |
| HLT: Coughing and associated symptoms | 5 (3.2%) | 2 (1.2%) |
| Cough | 4 (2.5%) | 2 (1.2%) |
| HLT: Upper respiratory tract signs and symptoms | 2 (1.3%) | 3 (1.9%) |
| Oropharyngeal pain | 1 (0.6%) | 2 (1.2%) |
| GASTROINTESTINAL DISORDERS | 48 (30.4%) | 34 (21.1%) |
| HLGT: Gastrointestinal inflammatory conditions | 5 (3.2%) | 3 (1.9%) |
| HLT: Gastritis (excl infective) | 4 (2.5%) | 1 (0.6%) |
| Gastritis | 4 (2.5%) | 1 (0.6%) |
| HLGT: Gastrointestinal motility and defaecation conditions | 17 (10.8%) | 15 (9.3%) |
| HLT: Diarrhoea (excl infective) | 14 (8.9%) | 12 (7.5%) |
| Diarrhoea | 14 (8.9%) | 12 (7.5%) |
| HLT: Gastrointestinal atonic and hypomotility disorders NEC | 2 (1.3%) | 3 (1.9%) |
| Constipation | 2 (1.3%) | 1 (0.6%) |
| HLGT: Gastrointestinal signs and symptoms | 37 (23.4%) | 23 (14.3%) |
| HLT: Dyspeptic signs and symptoms | 3 (1.9%) | 3 (1.9%) |
| Dyspepsia | 3 (1.9%) | 3 (1.9%) |
| HLT: Flatulence, bloating and distension | 4 (2.5%) | 5 (3.1%) |
| Abdominal distension | 2 (1.3%) | 1 (0.6%) |
| Flatulence | 2 (1.3%) | 4 (2.5%) |
| HLT: Gastrointestinal and abdominal pains (excl oral and throat) | 10 (6.3%) | 10 (6.2%) |
| Abdominal pain | 5 (3.2%) | 4 (2.5%) |
| Abdominal pain upper | 4 (2.5%) | 6 (3.7%) |
| HLT: Nausea and vomiting symptoms | 30 (19.0%) | 11 (6.8%) |
| Nausea | 28 (17.7%) | 11 (6.8%) |
| Vomiting | 7 (4.4%) | 0 |
| HEPATOBILIARY DISORDERS | 3 (1.9%) | 1 (0.6%) |
| HLGT: Hepatic and hepatobiliary disorders | 2 (1.3%) | 0 |
| HLT: Hepatocellular damage and hepatitis NEC | 2 (1.3%) | 0 |
| Hepatic steatosis | 2 (1.3%) | 0 |
| SKIN AND SUBCUTANEOUS TISSUE DISORDERS | 6 (3.8%) | 4 (2.5%) |
| HLGT: Epidermal and dermal conditions | 6 (3.8%) | 3 (1.9%) |
| HLT: Dermatitis and eczema | 0 | 2 (1.2%) |
| Dermatitis | 0 | 2 (1.2%) |
| HLT: Pruritus NEC | 3 (1.9%) | 0 |
| Pruritus | 2 (1.3%) | 0 |
| MUSCULOSKELETAL AND CONNECTIVE TISSUE DISORDERS | 16 (10.1%) | 11 (6.8%) |
| HLGT: Joint disorders | 4 (2.5%) | 3 (1.9%) |
| HLT: Joint related signs and symptoms | 1 (0.6%) | 3 (1.9%) |
| Arthralgia | 1 (0.6%) | 3 (1.9%) |
| HLT: Osteoarthropathies | 3 (1.9%) | 0 |
| Osteoarthritis | 2 (1.3%) | 0 |
| HLGT: Musculoskeletal and connective tissue disorders NEC | 10 (6.3%) | 7 (4.3%) |
| HLT: Musculoskeletal and connective tissue pain and discomfort | 10 (6.3%) | 7 (4.3%) |
| Back pain | 5 (3.2%) | 4 (2.5%) |
| Musculoskeletal chest pain | 3 (1.9%) | 0 |
| Pain in extremity | 2 (1.3%) | 2 (1.2%) |
| RENAL AND URINARY DISORDERS | 8 (5.1%) | 7 (4.3%) |
| HLGT: Urinary tract signs and symptoms | 5 (3.2%) | 4 (2.5%) |
| HLT: Urinary abnormalities | 4 (2.5%) | 3 (1.9%) |
| Microalbuminuria | 3 (1.9%) | 2 (1.2%) |
| HLGT: Urolithiases | 2 (1.3%) | 1 (0.6%) |
| HLT: Renal lithiasis | 2 (1.3%) | 1 (0.6%) |
| Nephrolithiasis | 2 (1.3%) | 1 (0.6%) |
| REPRODUCTIVE SYSTEM AND BREAST DISORDERS | 5 (3.2%) | 2 (1.2%) |
| HLGT: Menstrual cycle and uterine bleeding disorders | 3 (1.9%) | 0 |
| HLT: Menstruation and uterine bleeding NEC | 3 (1.9%) | 0 |
| Dysmenorrhoea | 2 (1.3%) | 0 |
| HLGT: Sexual function and fertility disorders | 0 | 2 (1.2%) |
| HLT: Erection and ejaculation conditions and disorders | 0 | 2 (1.2%) |
| Erectile dysfunction | 0 | 2 (1.2%) |
| GENERAL DISORDERS AND ADMINISTRATION SITE CONDITIONS | 14 (8.9%) | 11 (6.8%) |
| HLGT: Administration site reactions | 8 (5.1%) | 3 (1.9%) |
| HLT: Injection site reactions | 8 (5.1%) | 2 (1.2%) |
| Injection site erythema | 2 (1.3%) | 0 |
| Injection site haematoma | 3 (1.9%) | 2 (1.2%) |
| Injection site pruritus | 2 (1.3%) | 0 |
| HLGT: General system disorders NEC | 7 (4.4%) | 9 (5.6%) |
| HLT: Asthenic conditions | 5 (3.2%) | 4 (2.5%) |
| Asthenia | 2 (1.3%) | 1 (0.6%) |
| Fatigue | 3 (1.9%) | 2 (1.2%) |
| Malaise | 0 | 2 (1.2%) |
| HLT: General signs and symptoms NEC | 4 (2.5%) | 0 |
| Influenza like illness | 4 (2.5%) | 0 |
| HLT: Oedema NEC | 1 (0.6%) | 4 (2.5%) |
| Oedema peripheral | 1 (0.6%) | 4 (2.5%) |
| INVESTIGATIONS | 12 (7.6%) | 9 (5.6%) |
| HLGT: Gastrointestinal investigations | 7 (4.4%) | 2 (1.2%) |
| HLT: Digestive enzymes | 7 (4.4%) | 2 (1.2%) |
| Lipase increased | 7 (4.4%) | 1 (0.6%) |
| HLGT: Hepatobiliary investigations | 2 (1.3%) | 2 (1.2%) |

TABLE 62-continued

Number (%) of patients experiencing common TEAE(s) (PT ≥1% in any treatment group) presented by primary SOC, HLGT, HLT and PT - Safety population

| PRIMARY SYSTEM ORGAN CLASS<br>HLGT: High Level Group Term<br>HLT: High Level Term<br>Preferred Term | Lixisenatide<br>(N = 158) | Sitagliptin<br>(N = 161) |
|---|---|---|
| HLT: Liver function analyses | 2 (1.3%) | 2 (1.2%) |
| Alanine aminotransferase increased | 2 (1.3%) | 2 (1.2%) |
| INJURY, POISONING AND PROCEDURAL COMPLICATIONS | 6 (3.8%) | 9 (5.6%) |
| HLGT: Bone and joint injuries | 2 (1.3%) | 6 (3.7%) |
| HLT: Limb injuries NEC (incl traumatic amputation) | 2 (1.3%) | 4 (2.5%) |
| Joint injury | 2 (1.3%) | 2 (1.2%) |
| Limb injury | 0 | 2 (1.2%) |
| HLGT: Injuries NEC | 3 (1.9%) | 2 (1.2%) |
| HLT: Skin injuries NEC | 3 (1.9%) | 0 |
| Contusion | 3 (1.9%) | 0 |
| HLGT: Procedural related injuries and complications NEC | 2 (1.3%) | 0 |
| HLT: Non-site specific procedural complications | 2 (1.3%) | 0 |
| Procedural pain | 2 (1.3%) | 0 |

TEAE: Treatment Emergent Adverse Event,
SOC: System Organ Class,
HLGT: High Level Group Term,
HLT: High Level Term,
PT: Preferred Term.
MedDRA version: 13.1.
n (%) = number and percentage of patients with at least one TEAE.
Note:
Table sorted by SOC internationally agreed order and HLGT, HLT, PT by alphabetic order.
Only SOC with at least one PT ≥1% in at least one group are presented.

The invention claimed is:

1. A method for improving glucose tolerance in a diabetes type 2 patient in need thereof, comprising administering to said patient a therapeutically effective amount of the pharmaceutical combination comprising (a) desPro$^{36}$Exendin-4(1-39)-Lys$_6$-NH$_2$ or/and a pharmaceutically acceptable salt thereof, and (b) metformin or/and a pharmaceutically acceptable salt thereof to a subject in need thereof, wherein the patient to be treated is younger than 50 years and has a 2 hour postprandial plasma glucose concentration of at least 14 mmol/L.

2. The method of claim 1, wherein said patient is obese.

3. The method of claim 1, wherein said patient has a body mass index of at least 30 kg/m$^2$.

4. The method of claim 1, wherein said patient is an adult subject.

5. The method of claim 1, wherein said patient does not receive an antidiabetic treatment.

6. The method of claim 1, wherein diabetes mellitus type 2 has been diagnosed in said patient at least 1 year or at least 2 years before onset of therapy.

7. The method of claim 1, wherein said patient has a HbA$_{1c}$ value of about 7 to about 10%.

8. The method of claim 1, wherein said patient has a fasting plasma glucose concentration of at least 8 mmol/L.

9. The method of claim 1, wherein said patient has a glucose excursion of at least 2 mmol/L, at least 3 mmol/L, at least 4 mmol/L or at least 5 mmol/L, wherein the glucose excursion is the difference of the 2 hour postprandial plasma glucose concentration and plasma glucose concentration 30 minutes prior to a meal test.

* * * * *